US 008269014B2

(12) United States Patent
Chan Chun Kong et al.

(10) Patent No.: US 8,269,014 B2
(45) Date of Patent: Sep. 18, 2012

(54) THIOPHENE ANALOGUES FOR THE TREATMENT OR PREVENTION OF FLAVIVIRUS INFECTIONS

(75) Inventors: Laval Chan Chun Kong, Kirkland (CA); Sanjoy Kumar Das, Pierrefonds (CA); Carl Poisson, Montreal (CA); Constantin G. Yannopoulos, Ile-Perrot (CA); Guy Falardeau, Laval (CA); Louis Vaillancourt, Mascouche (CA); Real Denis, Montreal (CA)

(73) Assignee: Vertex Pharmaceuticals (Canada) Incorporated (CA)

( * ) Notice: Subject to any disclaimer, the term of this patent is extended or adjusted under 35 U.S.C. 154(b) by 0 days.

(21) Appl. No.: 13/172,477

(22) Filed: Jun. 29, 2011

(65) Prior Publication Data

US 2012/0059170 A1 Mar. 8, 2012

Related U.S. Application Data

(63) Continuation of application No. 11/984,330, filed on Nov. 15, 2007, now Pat. No. 8,003,685.

(60) Provisional application No. 60/858,939, filed on Nov. 15, 2006.

(51) Int. Cl.
*C07D 409/12* (2006.01)

(52) U.S. Cl. ........................................ 546/213

(58) Field of Classification Search ............... 546/213
See application file for complete search history.

(56) References Cited

U.S. PATENT DOCUMENTS

| | | | |
|---|---|---|---|
| 3,076,817 A | 2/1963 | Fiesselmann et al. |
| 3,470,151 A | 9/1969 | Doyel et al. |
| 4,180,662 A | 12/1979 | Pfister et al. |
| 4,710,506 A | 12/1987 | Davies et al. |
| 4,877,793 A | 10/1989 | Davies et al. |
| 5,276,009 A | 1/1994 | Muenster et al. |
| 5,679,678 A | 10/1997 | Binder et al. |
| 5,783,705 A | 7/1998 | Blok et al. |
| 5,807,854 A | 9/1998 | Bartroli et al. |
| 5,888,941 A | 3/1999 | Bartroli et al. |
| 5,933,303 A | 8/1999 | Hahn |
| 6,140,351 A | 10/2000 | Arnaiz et al. |
| 6,187,799 B1 | 2/2001 | Wood et al. |
| 6,248,767 B1 | 6/2001 | Blok et al. |
| 6,271,225 B1 | 8/2001 | Seio et al. |
| 6,294,276 B1 | 9/2001 | Ogino |
| 6,344,476 B1 | 2/2002 | Ranges et al. |
| 6,380,214 B1 | 4/2002 | Gant et al. |
| 6,410,586 B1 | 6/2002 | Moller |
| 6,414,013 B1 | 7/2002 | Fancelli et al. |
| 6,432,994 B1 | 8/2002 | Wu et al. |
| 6,448,290 B1 | 9/2002 | Ohuchida et al. |
| 6,458,805 B2 | 10/2002 | Blok et al. |
| 6,476,023 B1 | 11/2002 | Cirillo et al. |
| 6,515,002 B2 | 2/2003 | Illig et al. |
| 6,534,501 B2 | 3/2003 | Abraham et al. |
| 6,562,840 B1 | 5/2003 | Illig et al. |
| 6,602,874 B2 | 8/2003 | Howard et al. |
| 6,620,767 B1 | 9/2003 | Ducray et al. |
| 6,660,728 B2 | 12/2003 | Scheunemann et al. |
| 6,660,732 B2 | 12/2003 | Betageri et al. |
| 6,683,103 B2 | 1/2004 | Wu et al. |
| 6,689,854 B2 | 2/2004 | Fan et al. |
| 6,734,207 B2 | 5/2004 | Uckun et al. |
| 6,747,057 B2 | 6/2004 | Ruzafa et al. |
| 6,835,745 B2 | 12/2004 | Coghlan et al. |
| 6,858,223 B2 | 2/2005 | Hafner |
| 6,867,217 B1 | 3/2005 | South et al. |
| 6,881,741 B2 | 4/2005 | Chan Chun Kong et al. |
| 6,887,877 B2 | 5/2005 | Chan Chun Kong et al. |
| 6,892,279 B2 | 5/2005 | Mekhiel |
| 6,924,276 B2 | 8/2005 | Sorenson et al. |
| 6,960,594 B2 | 11/2005 | Labrecque et al. |
| 6,982,279 B2 | 1/2006 | Peukert et al. |
| 6,984,737 B2 | 1/2006 | Hartmann et al. |
| 7,015,223 B1 | 3/2006 | South et al. |
| 7,019,027 B2 | 3/2006 | Linden et al. |
| 7,084,170 B2 | 8/2006 | Grossman et al. |
| 7,084,171 B2 | 8/2006 | Grainger et al. |
| 7,098,240 B2 | 8/2006 | Griffiths et al. |
| 7,098,241 B2 | 8/2006 | Grossman et al. |
| 7,101,878 B1 | 9/2006 | Anderson et al. |
| 7,105,565 B2 | 9/2006 | Walter |
| 7,125,896 B2 | 10/2006 | Faull et al. |
| 7,135,550 B2 | 11/2006 | Come et al. |
| 7,138,530 B2 | 11/2006 | Subasinghe et al. |
| 7,157,585 B2 | 1/2007 | Lively et al. |

(Continued)

FOREIGN PATENT DOCUMENTS

AU 2003204708 7/2003

(Continued)

OTHER PUBLICATIONS

Office Action issued Aug. 24, 2006 in U.S. Appl. No. 10/730,272.
Office Action (EP) issued Aug. 19, 2010 in EP 07845534.2.
Office Action issued Mar. 14, 2007 in U.S. Appl. No. 10/730,272.
Office Action issued Mar. 29, 2006 in U.S. Appl. No. 10/730,272.
Office action issued May 2, 2008 in U.S. Appl. No. 11/433,749.
Office Action issued Sep. 8, 2008 in U.S. Appl. No. 11/433,749.
Office Action issued Sep. 18, 2007 in U.S. Appl. No. 11/042,442.
Poisson, Carl "Discovery and Structure-Activity Relationship of Trisubstituted Thiophene Derivatives as Potent Inhibitors of Hepatitis C Virus Replication", 15th Quebec-Ontario Minisymposium in Synthetic and Bioorganic Chemistry (QOMSBOC), Ottawa, ON, Nov. 5 7, 2004.

(Continued)

*Primary Examiner* — Taofiq A Solola
(74) *Attorney, Agent, or Firm* — Honigman Miller Schwartz and Cohn; Kathryn D. Soulier; Jonathan P. O'Brien

(57) ABSTRACT

Compounds represented by formula I:

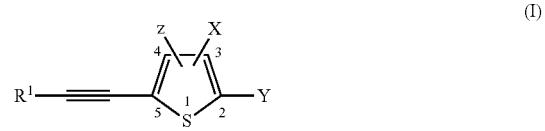

or pharmaceutically acceptable salts and solvates thereof, wherein $R_1$, X, Y, and Z are as defined herein, are useful for treating flaviviridae viral infections.

11 Claims, No Drawings

U.S. PATENT DOCUMENTS

| | | |
|---|---|---|
| 7,166,639 B2 | 1/2007 | Wan et al. |
| 7,179,836 B2 | 2/2007 | Adams et al. |
| 7,220,777 B2 | 5/2007 | Armstrong et al. |
| 7,285,557 B2 | 10/2007 | Carpenter et al. |
| 7,329,670 B1 | 2/2008 | Dumas et al. |
| 7,338,978 B2 | 3/2008 | Lahm et al. |
| 7,358,376 B2 | 4/2008 | Baxter et al. |
| 7,402,608 B2 | 7/2008 | Chan Chun Kong et al. |
| 7,470,701 B2 | 12/2008 | Jefferson et al. |
| 7,560,564 B2 | 7/2009 | Annis et al. |
| 7,569,600 B2 | 8/2009 | Denis et al. |
| 2004/0023961 A1 | 2/2004 | Dumas et al. |
| 2004/0087577 A1 | 5/2004 | Pratt et al. |
| 2004/0097492 A1 | 5/2004 | Pratt et al. |
| 2004/0162285 A1 | 8/2004 | Pratt et al. |
| 2004/0167123 A1 | 8/2004 | Pratt et al. |
| 2004/0198742 A1 | 10/2004 | Schoenafinger et al. |
| 2005/0009804 A1 | 1/2005 | Chan Chun Kong et al. |
| 2005/0075331 A1 | 4/2005 | Pratt et al. |
| 2005/0119332 A1 | 6/2005 | Jeppesen et al. |
| 2005/0256121 A1 | 11/2005 | Jefferson et al. |
| 2006/0142347 A1 | 6/2006 | Chan Chun Kong |
| 2006/0205748 A1 | 9/2006 | Annis et al. |
| 2006/0287329 A1 | 12/2006 | Kawaguchi et al. |
| 2007/0099929 A1 | 5/2007 | Thede et al. |
| 2008/0269481 A1 | 10/2008 | Chan Chun Kong |
| 2010/0160255 A1 | 6/2010 | Kamata et al. |

FOREIGN PATENT DOCUMENTS

| | | |
|---|---|---|
| CA | 2137976 | 6/1995 |
| CA | 2496680 | 11/1998 |
| CA | 2385972 | 4/2001 |
| CN | 1401732 | 3/2003 |
| DE | 1 055 007 | 4/1959 |
| DE | 146952 | 3/1981 |
| DE | 263055 | 12/1988 |
| DE | 199 20 247 | 11/2000 |
| DE | 199 03 398 | 8/2001 |
| EP | 0 269 295 | 6/1988 |
| FR | 2689129 | 10/1993 |
| JP | 57116077 | 7/1982 |
| JP | 63-141984 | 6/1988 |
| JP | 05117263 | 5/1993 |
| JP | 06025221 | 2/1994 |
| JP | 7-48360 | 2/1995 |
| JP | 2001-10957 | 1/2001 |
| JP | 2001-354658 | 12/2001 |
| JP | 2003-073357 | 3/2003 |
| JP | 2004-513163 | 4/2004 |
| WO | WO 97 05130 | 2/1997 |
| WO | WO 97 05310 | 6/1997 |
| WO | WO 98 49162 | 11/1998 |
| WO | WO 98 52558 | 11/1998 |
| WO | WO 98 52559 | 11/1998 |
| WO | WO 99 11647 | 3/1999 |
| WO | WO 99 32106 | 7/1999 |
| WO | WO 99 32110 | 7/1999 |
| WO | WO 99 32111 | 7/1999 |
| WO | WO 99 32455 | 7/1999 |
| WO | WO 99 32477 | 7/1999 |
| WO | WO 99 40088 | 8/1999 |
| WO | WO 99 46237 | 9/1999 |
| WO | WO 99 46244 | 9/1999 |
| WO | WO 99 52896 | 10/1999 |
| WO | WO 00 20358 | 4/2000 |
| WO | WO 00 47194 | 8/2000 |
| WO | WO 00 47578 | 8/2000 |
| WO | WO 00 55152 | 9/2000 |
| WO | WO 00 66094 | 9/2000 |
| WO | WO 01 44226 | 6/2001 |
| WO | WO 01 49289 | 7/2001 |
| WO | WO 01 58890 | 8/2001 |
| WO | WO 01 81345 | 11/2001 |
| WO | WO 02 28353 | 4/2002 |
| WO | WO 02 38542 | 5/2002 |
| WO | WO 02 100851 | 12/2002 |
| WO | WO 03 028731 | 4/2003 |
| WO | WO 03 037886 | 5/2003 |
| WO | WO 03 093290 | 11/2003 |
| WO | WO 2004 041818 | 5/2004 |
| WO | WO 2004 052879 | 6/2004 |
| WO | WO 2004 110357 | 12/2004 |
| WO | WO 2005 023761 | 3/2005 |
| WO | WO 2005 023819 | 3/2005 |
| WO | WO 2005 044008 | 5/2005 |
| WO | WO 2005 060711 | 7/2005 |
| WO | WO 2005 063734 | 7/2005 |
| WO | WO 2005 095386 | 12/2005 |
| WO | WO 2006 018544 | 2/2006 |
| WO | WO 2006 047503 | 5/2006 |
| WO | WO 2006 072347 | 7/2006 |
| WO | WO 2006 072348 | 7/2006 |
| WO | WO 2006 091862 | 8/2006 |
| WO | WO 2006 093518 | 9/2006 |
| WO | WO 2006 119646 | 11/2006 |
| WO | WO 2007 058990 | 5/2007 |
| WO | WO 2007 146712 | 12/2007 |
| WO | WO 2008 017688 | 2/2008 |
| WO | WO 2008 043791 | 4/2008 |

OTHER PUBLICATIONS

Rarey, M., et al., "Similarity searching in large combinatorial chemistry spaces", Journal of Computer-Aided Molecular Design (2001), 15(6), pp. 497-520.

Redman, A.M., et al., "P38 Kinase Inhibitors for the Treatment of Arthritis and Osteoporosis: Thienyl, Furyl, and Pyrrolyl Ureas"; Bioorg. Med. Chem. Lett., vol. 11, 2001, pp. 9-12.

Rudolph, M.J., et al., "Design and Synthesis of 4,5-Disubstituted-thiophene-2-amidines as Potent Urokinase Inhibitors", Bioorganic & Medicinal Chemistry Letters (2002), 12(3), pp. 491-495.

Saito, K., et al., "A One-Step Synthesis of Thiophene Derivatives", Synthesis (1982), (12), pp. 1056-1059.

Schatz, J., "Product Class 10: Thiophenes, Thiophene 1,1-Dioxindes, and Thiophene 1-Oxides", Science of Synthesis (2002), 9, pp. 287-422.

Smith, R.A., et al., "Discovery of Heterocyclic Ureas as a New Class of Raf Kinase Inhibitors: Identification of a Second Generation Lead by a Combinatorial Chemistry Approach"; Bioorg. Med. Chem. Lett. vol. 11, No. 20, 2001, pp. 2775-2778.

Sostegni, R., "Sequential Versus Concomitant Administration of Ribavirin and Interferon Alfa-n3 . . . ", Hepatology, 28 (2), (1998), pp. 341-346.

Sugiyama, M., et al., "Condensed Thienopyrimidines. I. Synthesis and Gastric Antisecretory Activity of 2,3-Dihydro-5H-oxazolothienopyrimidin-5-one Derivatives"; Chem. Pharm. Bull., vol. 37, No. 8, 1989, pp. 2091-2102.

Translation of "Notice of Grounds for Rejection" dated Oct. 7, 2008, Japanese Patent Application No. 2003 503618.

Tronchet, J.M.J., et al., "C-glycosylic derivatives XXVI New Routes to isoxazolic and thiophenic C-nucleosides"; Helvetica Chimica Acta. 1975 58(6), pp. 1735-1738.

Tronchet, J.M.J., et al., "C-glycosylic derivatives XXVI New Routes to isoxazolic and thiophenic C-nucleosides (abstract)"; Helvetica Chimica Acta. 1975 58(6), pp. 1735-1738.

Vega, S., et al., "Thiophene isosteres: synthesis and pharmacological study of 3-(azol-l-yl)thieno isothiazole-1, 1-dioxides"; Eur. J. Med. Chem., vol. 23, No. 4, 1988, pp. 329-334.

Vicari, A., "Safety, pharmacokinetics and immune effects in normal volunteers of CPG 10101 . . . ", Antiviral Therapy, 12 (5), (2007), pp. 741-751.

Written Opinion and Int'l Search Report for Int'l Application No. PCT/CA2006/00078 dated Nov. 13, 2007.

Wu, C., et al., "Selective Alkylation/Acylation of DI- or Trianions: Expeditious Derivatization of Endothelin Antagonists", Synthetic Communications (2002), 32 (10), pp. 1615-1624.

Yannopoulos, C., et al., "HCV NS5B polymerase-bound conformation of a soluble sulfonamide inhibitor by 2D transferred NOESY", Bioorganic & Medicinal Chemistry Letters 14 (2004) pp. 5333-5337.

Bartroli, J., et al., "New Azole Antifungals. 2. Synthesis and Antifungal Activity of Heterocyclecarboxamide Derivatives of 3-Amino-2-aryl-1-azolyl-2-butanol", Journal of Medicinal Chemistry (1998), 41(11), pp. 1855-1868.

Chan, L. et al., "Discovery of thiophene-2-carboxylic acids as potent inhibitors of HCV NS5B polymerase and HCV subgenomic RNA replication. Part 1: Sulfonamides", Bioorganic & Medicinal Chemistry Letters 14 (2004) pp. 793-796.

Chan, L., et al., "Discovery of a novel class of HCV NS5B RNA dependent polymerase inhibitors: SAR studies and activity in the replicon cell line", Poster submitted at 16th ICAR-Savannah, Apr. 2003 (14 pages).

Chan, L., et al., "Discovery of thiophene-2-carboxylic acids as potent inhibitors of HCV NS5B polymerase and HCV subgenomic RNA replication. Part 2: Tertiary amides", Bioorganic & Medicinal Chemistry Letters 14 (2004) pp. 797-800.

Chan, L., et al., "Identification of N,N-Disubstituted Phenylalanines as a Novel Class of Inhibitors of Hepatitis C NS5B Polymerase", J. Med. Chem. (2003), 46, pp. 1283-1285.

Compound Registration Forms from Maybridge plc., Registration date Dec. 12, 2000, BCH No. BCH-19467 (1 page).

Compound Registration Forms from Maybridge plc., Registration date Feb. 8, 2001, BCH Nos. BCH-18910, BCH-19779, BCH-19781, BCH-19782, BCH-19783, BCH-19784, BCH-19787, BCH-19789, BCH-19790, BCH-19791, BCH-19792, BCH-19793, BCH-19794, BCH-19795, BCH-19796, BCH-19797, BCH-19799, BCH-19800 (18 pages).

Compound Registration Forms from Maybridge plc., Registration date Feb. 13, 2001, BCH Nos. BCH-19209, BCH-19903, BCH-19904 (3 pages).

Compound Registration Forms from Maybridge plc., Registration date May 24, 2002, BCH Nos. BCH-24851, BCH-24852, BCH-24853, BCH-24861, BCH-24862, BCH-24867 (2 pages).

Compound Registration Forms from Maybridge plc., Registration date Jul. 4, 2002, BCH Nos. BCH-25359, BCH-25365, BCH-25367 (3 pages).

Desai, J.R. et al., "Thieno[3,2-d]pyrimidines—Part—II: Preparation and antimicrobial activity of 2-methyl-3-N-arylsulphonamido-6-phenylthieno[3,2-d]pyrimidin-4(3H)-ones", J. Inst. Chemists (India), vol. 67, 1995 pp. 136-137.

De Stevens, G., et al., "Heterocylcic Disulphonamides and Their Diuretic Properties", Journal of Medicinal & Pharmaceutical Chemistry (1959), 1, pp. 565 76.

Doat, E.G., et al., "3,5-Dilithiated Tertiary Thiophene 2-Carboxamide, Regoiselective Entries into Diversely Substituted Thiophenes", Tetrahedron Letters (1985), 26(9), pp. 1149 1152.

European Search Report (Extended) dated Feb. 9, 2010 in EP Appl. No. 06741500.0 (PCT/CA2006/000786).

Fabrichnyi, B.P., et al., "Synthesis of Aliphatic amino acids from thiophene derivatives (English translation)", Zhurnal Organicheskoi Khimii (1970), 6(5), pp. 1091-1100.

Fabrichnyi, B.P., et al., "Synthesis of Aliphatic Amino Acids from Thiophene Derivatives", May 1970, pp. 1093-1102.

Fabrichnyi, B.P., et al., "The Beckmann Rearrangement of Oximes of Thiophenocycloalkanones", Zhurnal Obshchei Khimii (1961), 31, pp. 1244 53.

Fan, et al., Abstract of "Zhongguo Yiyao Gongye Zazhi Synthesis of Iornoxicam" 2003:267476 HCAPLUS (2002).

Fan, et al., "Zhongguo Yiyao Gongye Zazhi", Chinese Journal of Pharmaceuticals (2002), 33(8), pp. 365-366.

Fedorova, I.N., et al., "Synthesis and Antiflammatory Activity of Derivatives of 2-Aminothiophene-5-Acetic Acids", Translated from Khimiko-Farmatsevticheskii Zhurnal (1986), 20(1), pp. 39-45.

Gol'Dfarb, Y.L., et al., "Reductive Acetylation of Netrocarboxylic Acids of the Thiophene and Furan Series or their Esters", Translated from Khimiya Geterotsiklisheskikh Soedinenii (1983), (12), pp. 1626-1629.

Gol'Dfarb, Y.L., et al., "Synthesis of Aliphatic Amino Acids from Thiophene Derivatives, XV, Preparation of e-Aminodicarboxylic Acids", Translated from Zhurnal Organicheskoi Khimii (1975), 11(11), pp. 2400-2407.

Gol'Dfarb, et al., Zhurnal Obshchei Khimii, vol. 29, 1959, pp. 3636-3644.

Gol'Dfarb, YA. L., et al., "Action of alkali metals in liquid ammonia on substituted thiophenes—Communication 9. Preparation of 5-Mercapto-4-Ketoalkanoic acids by reductive cleavage of 4-acetylamino- and 4-nitrothiophene-2-carboxylic acids", Izv. Akad. Nauk SSSR, Ser. Khim. (1984), (10), pp. 2136-2139.

Goya, P. et al., "Synthesis of 4-Oxo-3,4-dihydro-1H-thieno[3,4-c] and thieno [3,2-c][1,2,6]thiadiazine 2,2-Dioxides", Synthesis Apr. 1989, pp. 280-282.

Hadziyannis, S., "Emerging treatments in chronic hepatitis B", Expert Opinion Emerg. Drugs, 9 (2), (2004), pp. 207-221.

Iino, M., et al., "Rational Design and Evaluation of New Lead Compound Structures for Selective βARK1 Inhibitors", Journal of Medicinal Chemistry (2002), 45(11), pp. 2150-2159.

Int'l Search Report for Int'l Application No. PCT/CA02/00876 mailed Nov. 26, 2002.

Int'l Search Report for Int'l Application No. PCT/CA2007/002064 mailed May 19, 2009.

Int'l Search Report issued Jun. 4, 2004 for Int'l Application No. PCT/CA03/01912.

Jones, D.H., et al., "Amidines and Guanidines Related to Congocidin . . . ", Journal of the Chemical Society [Section] C: Organic (1968), (5), pp. 550-554.

Kantlehner, J.W., et al., "Orthoamide. IL. Umsetzungen von Orthoamid-Derivaten mitSchwefel und Selen, Synthesen von 1,3-Thiazol- und 1,3-Selenazolderivaten"; ISR ref. XP002220245 Prakt. Chem., vol. 338, 1996, pp. 403-413.

Kim, B.S., et al., "Reactions of Thioaroylketene S,N-Acetals with 1,3-Dicarbonyl Compounds in the Presence of Mercury(II) Acetate: A general Route to 2-Acyl- and 2-Aroyl-3-(alkylamino)-5-arylthiophenes and 2-(Ethoxycarbonyl)-3-(methylamino)-5-arylt hiophenes"; ISR ref. XP001118697, J. Org. Chem. vol. 63, No. 18, 1998, pp. 6086-6087.

Kim, B.S., K. Kim, "A Facile and Convenient Synthesis of 3-Alkylamino-5-arylthiophenes with a Variety of Substituents at C-2 and Studies of Reaction Mechanisms"; ISR ref XP001118698, J. Org. Chem. vol. 65, No. 12, 2000, pp. 3690-3699.

Kim, K., et al., "Thioaroylketene S,N-Acetals: Versatile Intermediates for the Synthesis of 3-Alkylamino-5-Arylthiophenes with a Variety of Functional Group at C-2", Phosphorus, Sulfur and Silicon and the Related Elements (1999), pp. 153-154, 393-394.

Kohara, T., et al., "Synthesis of Thieno[2,3,b][1,5]benzoxazepine Derivatives", Journal of Heterocyclic Chemistry (2002), 39(1), pp. 163-171.

Lancelot, J.C., et al., "A Facile Synthesis of new Beta.-Lactams"; ISR ref. XP002220247, J. Heterocycl. Chem., vol. 33, No. 2, 1996, pp. 427-430.

Lee, D.G., et al., "Novel Synthesis of 5,6-Dihydro-4H-thieno[2,3,b]pyrrol-5-ones via the Rhodium(II)-Mediated Wolff Rearrangement of . . . ", Organic Letters (2002), 4(6), pp. 873-876.

Lee, J.S., "Reactions of thiobenzoylketene S,N-acetals with silyl enol ethers of cyclic ketones in the presence of desilylating reagents: . . . ", Journal of the Chemical Society, Perkin Transactions 1 (2001), (21), 2774-2780.

Litvinov, "Hetaryladamantanes. 2. 3-(1-Adamantyl)-3-chloropropenal: its structure and synthesis of adamantly-substituted nitrogen-containing heterocycles from it", Translated from Izvestiya Akademii Nauk SSSR, Seriya Khimicheskaya (1985), (8), pp. 1858-1863.

Liu, P., et al., "Synthesis and mesogenic properties of a novel family of oligothiophene derivatives", Liquid Crystals, 2001, vol. 28, No. 4, pp. 581 589.

Marchand, E., et al., "Alpha.-Thioxothioamides. Réactions de cycloaddition [4+] avec l'acétylènedicarboxylate de diméthyle et le propiolate de méthyle"; Bull. Soc. Chim. FR., vol. 133, No. 9, 1996, pp. 903-912.

McKinnon, D. M., et al., "The conversions of isothiazolium salts into thiophenecarboxylic ester derivatives"; ISR ref. XP002220248, Can. J. Chem. 1984, vol. 62, No. 8, pp. 1580-1584.

Migianu, E., et al., "Synthesis of new Thieno[b]azepinediones from a-Methylene Ketones", Synthesis (2002), (8), pp. 1096-1100.

Migianu, International Electronic Conferences on Synthetic Organic Chemistry, 5th, 6th, Sep. 1-30, 2001 and 2002 [and] 7th, 8th, Nov. 1-30, 2003 and 2004, pp. 1302-1307.

Nguyen-Ba, N., et al., "Discovery and SAR Studies of a Novel Class of HCV NS5B RNA-dependent RNA Polymerase Inhibitors", The 16th International Conference on Antiviral Research (ICAR) convened on Apr. 27 May 1, 2003.

Notice of Allowance issued Jun. 16, 2008 in U.S. Appl. No. 11/042,442.

Notice of Allowance issued Mar. 17, 2008 in U.S. Appl. No. 11/042,442.

Notice of Allowance issued Sep. 28, 2007 in U.S. Appl. No. 10/730,272.

Office Action issued Apr. 2, 2007 in U.S. Appl. No. 11/042,442.

SEQUENCE LISTING

```
<160> NUMBER OF SEQ ID NOS: 8

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
```
gctagcgcta gctcaatgtc ctacacatgg                                    30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctcgagctcg agcgtccatc ggttggggag                                    30

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atacatatgg ctagcatgtc aatgtcctac acatgg                             36

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggatccggat cccgttcatc ggttggggag                                    30

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 5

His His His His His His
1               5

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcagcctggt gctcctctat ctat                                          24

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aagcccttat ggtaggacaa aatattt                                       27

```
<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
tccagggccc acacctctgc ct                                              22
```

THIOPHENE ANALOGUES FOR THE TREATMENT OR PREVENTION OF FLAVIVIRUS INFECTIONS

CROSS-REFERENCE TO RELATED APPLICATION

This application is a continuation of U.S. Ser. No. 11/984,330, filed Nov. 15, 2007 now U.S. Pat. No. 8,003,685, which claims the priority of U.S. Application Ser. No. 60/858,939, filed Nov. 15, 2006. Both of these applications are incorporated herein in their entirety.

SEQUENCE LISTING

This application incorporates by reference in its entirety the Sequence Listing named "VIRO0029.txt" created on Jul. 1, 2008, that is 2,306 bytes, and filed electronically herewith on Oct. 8, 2011.

TECHNICAL FIELD OF THE INVENTION

The present invention relates to novel compounds and a method for the treatment or prevention of Flavivirus infections using novel compounds.

BACKGROUND OF THE INVENTION

Hepatitis is a disease occurring throughout the world. It is generally of viral nature, although there are other causes known. Viral hepatitis is by far the most common form of hepatitis. Nearly 750,000 Americans are affected by hepatitis each year, and out of those, more than 150,000 are infected with the hepatitis C virus ("HCV").

HCV is a positive-stranded RNA virus belonging to the Flaviviridae family and has closest relationship to the pestiviruses that include hog cholera virus and bovine viral diarrhea virus (BVDV). HCV is believed to replicate through the production of a complementary negative-strand RNA template. Due to the lack of efficient culture replication system for the virus, HCV particles were isolated from pooled human plasma and shown, by electron microscopy, to have a diameter of about 50-60 nm. The HCV genome is a single-stranded, positive-sense RNA of about 9,600 by coding for a polyprotein of 3009-3030 amino-acids, which is cleaved co and post-translationally into mature viral proteins (core, E1, E2, p7, NS2, NS3, NS4A, NS4B, NS5A, NS5B). It is believed that the structural glycoproteins, E1 and E2, are embedded into a viral lipid envelope and form stable heterodimers. It is also believed that the structural core protein interacts with the viral RNA genome to form the nucleocapsid. The nonstructural proteins designated NS2 to NS5 include proteins with enzymatic functions involved in virus replication and protein processing including a polymerase, protease and helicase.

The main source of contamination with HCV is blood. The magnitude of the HCV infection as a health problem is illustrated by the prevalence among high-risk groups. For example, 60% to 90% of hemophiliacs and more than 80% of intravenous drug abusers in western countries are chronically infected with HCV. For intravenous drug abusers, the prevalence varies from about 28% to 70% depending on the population studied. The proportion of new HCV infections associated with post-transfusion has been markedly reduced lately due to advances in diagnostic tools used to screen blood donors.

Combination of pegylated interferon plus ribavirin is the treatment of choice for chronic HCV infection. This treatment does not provide sustained viral response (SVR) in a majority of patients infected with the most prevalent genotype (1a and 1b). Furthermore, significant side effects prevent compliance to the current regimen and may require dose reduction or discontinuation in some patients.

There is therefore a great need for the development of anti-viral agents for use in treating or preventing Flavivirus infections.

SUMMARY OF THE INVENTION

In one aspect, the present invention provides a compound of formula I:

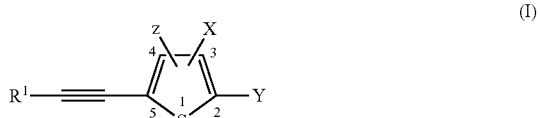

or pharmaceutically acceptable salts thereof;
wherein,
$R^1$ is $C_{1-6}$ alkyl, $C_{3-6}$ cycloalkyl, or $C_{6-14}$ aryl which is substituted one or more times by —NH($C_{1-4}$ alkyl), —N($C_{1-4}$ alkyl)$_2$, hydroxyl, NH$_2$, 3-12 member heterocycle, or NHSO$_2$C$_{6-18}$ aryl;
Z is H, halogen, $C_{1-6}$ alkyl which is unsubstituted or substituted one or more times by $R^{10}$, $C_{2-6}$ alkenyl which is unsubstituted or substituted one or more times by $R^{10}$, or $C_{2-6}$ alkynyl which is unsubstituted or substituted one or more times by $R^{10}$;
X is

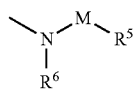

M is

$R^5$ is cyclohexyl which is unsubstituted or substituted one or more times by $R^{13}$;
$R^6$ is

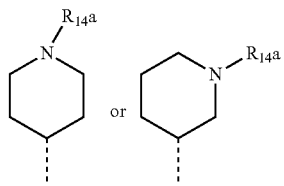

or cyclohexyl which is substituted one or more times by $R^{14}$;
Y is COOR$^7$, COCOOR$^7$, P(O)OR$^a$OR$^b$, S(O)OR$^7$, S(O)$_2$OR$^7$, tetrazole, CON(R$^7$)CH(R$^7$)COOR$^7$, CONR$^8$R$^9$, CON(R$^7$)—SO$_2$—R$^7$, CONR$^7$OH and halogen;

$R^7$, $R^8$ and $R^9$ are each independently H, $C_{1-12}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 member heteroaryl which is unsubstituted or substituted one or more times by $R^{11}$, 6-18 member heteroaralkyl which is unsubstituted or substituted one or more times by $R^{11}$, 3-12 member heterocycle which is unsubstituted or substituted one or more times by $R^{12}$, or 4-18 member heterocycle-alkyl which is unsubstituted or substituted one or more times by $R^{12}$, or $R^8$ and $R^9$ are taken together with the nitrogen atom to form a 3 to 10 member heterocycle which is unsubstituted or substituted one or more times by $R^{12}$ or a 5-12 member heteroaryl which is unsubstituted or substituted one or more times by $R^{11}$; and $R_a$ and $R_b$ are each independently chosen from H, $C_{1-12}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 member heteroaryl which is unsubstituted or substituted one or more times by $R^{11}$, 6-18 member heteroaralkyl which is unsubstituted or substituted one or more times by $R^{11}$, 3-12 member heterocycle which is unsubstituted or substituted one or more times by $R^{12}$, or 4-18 member heterocycle-alkyl which is unsubstituted or substituted one or more times by $R^{12}$, or $R^a$ and $R^b$ are taken together with the oxygen atoms to form a 5 to 10 member heterocycle which is unsubstituted or substituted one or more times by $R^{10}$ or a 5-12 member heteroaryl which is unsubstituted or substituted one or more times by $R^{11}$;

$R^{10}$ is halogen, oxo, —$NH_2$, —$NH(C_{1-4}$ alkyl), —$N(C_{1-4}$ alkyl)$_2$, —$CONH_2$, —$CONH(C_{1-4}$ alkyl), —$CON(C_{1-4}$ alkyl)$_2$, —NHCOH, —$N(C_{1-4}$ alkyl)COH, —$N(C_{1-4}$ alkyl)$COC_{1-4}$ alkyl, —$NHCOC_{1-4}$ alkyl, —C(O)H, —$C(O)C_{1-4}$ alkyl, carboxy, —$C(O)OC_{1-4}$ alkyl, hydroxyl, $C_{1-4}$ alkoxy, nitro, nitroso, azido, cyano, —$S(O)_{0-2}H$, —$S(O)_{0-2}C_{1-4}$ alkyl, —$SO_2NH_2$, —$SO_2NH(C_{1-4}$ alkyl), —$SO_2N(C_{1-4}$ alkyl)$_2$, —$NHSO_2H$, —$N(C_{1-4}$ alkyl)$SO_2H$, —$N(C_{1-4}$ alkyl)$SO_2C_{1-4}$ alkyl, or —$NHSO_2C_{1-4}$ alkyl;

$R^{11}$ is halogen, $C_{1-6}$ alkyl, halogenated $C_{1-6}$ alkyl, $C_{2-6}$ alkenyl, $C_{2-6}$ alkynyl, $C_{1-6}$ alkoxy, —$NH_2$, —$NH(C_{1-4}$ alkyl), —$N(C_{1-4}$ alkyl)$_2$, —$CONH_2$, —$CONH(C_{1-4}$ alkyl), —$CON(C_{1-4}$ alkyl)$_2$, —NHCOH, alkyl)COH, alkyl)$COC_{1-4}$ alkyl, —$NHCOC_{1-4}$ alkyl, —C(O)H, —$C(O)C_{1-4}$ alkyl, carboxy, —$C(O)OC_{1-4}$ alkyl, hydroxyl, $C_{1-6}$ alkoxy, nitro, nitroso, azido, cyano, —$S(O)_{0-2}H$, —$S(O)_{0-2}C_{1-4}$ alkyl, —$SO_2NH_2$, —$SO_2NH(C_{1-4}$ alkyl), —$SO_2N(C_{1-4}$ alkyl)$_2$, —$NHSO_2H$, alkyl)$SO_2H$, alkyl)$SO_2C_{1-4}$ alkyl, or —$NHSO_2C_{1-4}$ alkyl;

$R^{12}$ is halogen, oxo, $C_{1-6}$ alkyl, halogenated $C_{1-6}$ alkyl, $C_{2-6}$ alkenyl, $C_{2-6}$ alkynyl, —$NH_2$, —$NH(C_{1-4}$ alkyl), —$N(C_{1-4}$ alkyl)$_2$, —$CONH_2$, —$CONH(C_{1-4}$ alkyl), —$CON(C_{1-4}$ alkyl)$_2$, —NHCOH, alkyl)COH, alkyl)$COC_{1-4}$ alkyl, —$NHCOC_{1-4}$ alkyl, —C(O)H, —$C(O)C_{1-4}$ alkyl, carboxy, —$C(O)OC_{1-4}$ alkyl, hydroxyl, $C_{1-6}$ alkoxy, nitro, nitroso, azido, cyano, —$S(O)_{0-2}H$, —$S(O)_{0-2}C_{1-4}$ alkyl, —$SO_2NH_2$, —$SO_2NH(C_{1-4}$ alkyl), —$SO_2N(C_{1-4}$ alkyl)$_2$, —$NHSO_2H$, alkyl)$SO_2H$, alkyl)$SO_2C_{1-4}$ alkyl, or —$NHSO_2C_{1-4}$ alkyl;

$R^{13}$ is OH, halogen, $C_{1-6}$-alkyl, halogenated $C_{1-6}$-alkyl, $C_{1-6}$-alkoxy, halogenated $C_{1-6}$-alkoxy, cyano, nitro, —$NH_2$, —$NH(C_{1-4}$ alkyl), —$N(C_{1-4}$ alkyl)$_2$, —$CONH_2$, —CONH $(C_{1-4}$ alkyl), —$CON(C_{1-4}$ alkyl)$_2$, —NHCOH, alkyl)COH, alkyl)$COC_{1-4}$ alkyl, —$NHCOC_{1-4}$ alkyl, —C(O)H, —$C(O)C_{1-4}$ alkyl, carboxy, —$C(O)OC_{1-4}$ alkyl, —$S(O)_{0-2}C_{1-4}$ alkyl, —$SO_2NH_2$, —$SO_2NH(C_{1-4}$ alkyl), —$SO_2N(C_{1-4}$ alkyl)$_2$, —N(C alkyl)$SO_2H$, —N(C alkyl)$SO_2C_{1-4}$ alkyl, —$NHSO_2C_{1-4}$ alkyl, $C_{6-14}$-aryl, $C_{6-14}$-aryloxy, or $C_{6-14}$-aryloxy-$C_{1-6}$-alkyl;

$R^{14}$ is OH, halogen, $C_{1-6}$-alkoxy, $C_{1-6}$-alkyl, $C_{1-6}$-alkyl-CO—N($C_{1-6}$-alkyl)-, or 5 to 10 member heteroaryl; and $R^{14a}$ is $C_{1-6}$-alkyl, $C_{3-7}$-cycloalkyl, halogenated $C_{1-6}$-alkyl, $C_{1-6}$-alkyl-CO—, —$S(O)_{0-2}C_{1-4}$ alkyl, 5 to 10 member heteroaryl or $C_{6-14}$-aryl.

The compounds of the present invention are HCV polymerase inhibitors. Surprisingly, it has been found that the compounds according to the present invention and having a specific substitution pattern, exhibit improved properties relative to other thiophene HCV polymerase inhibitors. It is therefore believed that the compounds of the present invention have excellent potential for the treatment and prevention of hepatitis C infections.

In another aspect, there is provided a method for treating or preventing a Flaviviridae viral infection in a patient comprising administering to the patient a therapeutically effective amount of a compound, composition or combination of the invention.

In another aspect, there is provided a pharmaceutical composition comprising at least one compound of the invention and at least one pharmaceutically acceptable carrier or excipient.

In another aspect, there is provided a combination comprising a compound of the invention and one or more additional agents chosen from viral serine protease inhibitors, viral polymerase inhibitors, viral helicase inhibitors, immunomudulating agents, antioxidant agents, antibacterial agents, therapeutic vaccines, hepatoprotectant agents, antisense agent, inhibitors of HCV NS2/3 protease and inhibitors of internal ribosome entry site (IRES).

In a further aspect, there is provided the use of a compound, composition or combination of the invention for treating or preventing a Flaviviridae viral infection in a patient.

In still another aspect, there is provided the use of a compound, composition or combination of the invention for inhibiting or reducing the activity of viral polymerase in a patient.

In still another aspect, there is provided the use of a compound, composition or combination of the invention for the manufacture of a medicament for treating or preventing a viral Flaviviridae infection in a patient.

DETAILED DESCRIPTION OF THE INVENTION

In one embodiment, compounds of the present invention comprise those wherein the following embodiments are present, either independently or in combination.

In accordance with a preferred compound or method aspect, the compounds of the present invention are represented by formula IA:

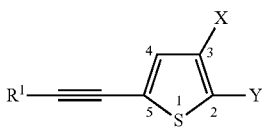

(IA)

or pharmaceutically acceptable salts thereof;
wherein, each of X, Y and $R^1$ are as defined above.

In accordance with a further preferred compound or method aspect, the compounds of the present invention are represented by formula IB:

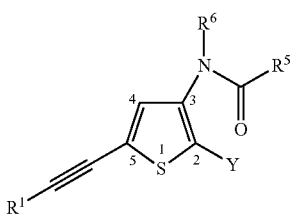

(IB)

or pharmaceutically acceptable salts thereof;
wherein each of X, Y, $R^1$, $R^5$, and $R^6$ are as defined above.

According to a further embodiment, $R^1$ in formulas I, IA, and IB is $C_{1-6}$ alkyl or $C_{3-6}$ cycloalkyl which are unsubstituted or substituted one or more times by —$NH_2$, $NHCH_3$, $N(CH_3)_2$, or hydroxyl.

According to a further embodiment, $R^1$ in formulas I, IA, and IB is $C_{1-6}$ alkyl which is unsubstituted or substituted one or more times by —$NH_2$ $NHCH_3$, $N(CH_3)_2$, or hydroxyl.

According to a further embodiment, $R^1$ in formulas I, IA, and IB is $C_{1-6}$ alkyl.

According to a further embodiment, $R^1$ in formulas I, IA, and IB is $R^1$ is methyl, ethyl, propyl, isopropyl, butyl, sec.-butyl, or tert.-butyl.

According to a further embodiment, $R^1$ in formulas I, IA, and IB is cyclopropyl, cyclobutyl, cyclopentyl, or cyclohexyl.

According to a further embodiment, $R^1$ in formulas I, IA, and IB is phenyl

According to a further embodiment, Z in formula I is H, halogen, or $C_{1-6}$ alkyl which is unsubstituted or substituted one or more times by $R^{10}$.

According to a further embodiment, Z in formula I is H, halogen, or $C_{1-4}$ alkyl which is unsubstituted or substituted one or more times by $R^{10}$.

According to a further embodiment, Z in formula I is H or $C_{1-4}$ alkyl.

According to a further embodiment, Z in formula I is H or methyl.

According to a further embodiment, Y in formulas I, IA, and IB, is $COOR^7$, and $R^7$ is H, $C_{1-12}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, or $C_{6-14}$ aryl which is unsubstituted or substituted one or more times by $R^{11}$.

According to a further embodiment, Y in formulas I, IA, and IB, is $COOR^7$, and $R^7$ is H, $C_{1-6}$ alkyl which is unsubstituted or substituted one or more times by $R^{10}$, or $C_{6-14}$ aryl which is unsubstituted or substituted one or more times by $R^{11}$.

According to a further embodiment, Y in formulas I, IA, and IB, is $COOR^7$, and $R^7$ is H, $C_{1-4}$ alkyl which is unsubstituted or substituted one or more times by $R^{10}$, or phenyl which is unsubstituted or substituted one or more times by $R^{11}$.

According to a further embodiment, Y in formulas I, IA, and IB, is $COOR^7$ and $R^7$ is H, $C_{1-4}$ alkyl or phenyl.

According to a further embodiment, Y in formulas I, IA, and IB, is $COOR^7$ and $R^7$ is H, methyl, or ethyl.

According to a further embodiment, Y in formulas I, IA, and IB, is $COOR^7$ and $R^7$ is H.

According to further embodiment, $R^5$ in formulas I, IA, and IB is cyclohexyl which is unsubstituted or substituted one or more times by OH, halogen, $C_{1-6}$-alkyl, halogenated $C_{1-6}$-alkyl, $C_{1-6}$-alkoxy, halogenated $C_{1-6}$-alkoxy, cyano, nitro, —$NH_2$, —$NH(C_{1-4}$ alkyl), or —$N(C_{1-4}$ alkyl$)_2$.

According to further embodiment, $R^5$ in formulas I, IA, and IB is cyclohexyl which is substituted in the 4-position.

According to further embodiment, in formulas I, IA, and IB, X is —$NR^6$—CO—$R^5$ and $R^5$ is cyclohexyl which is substituted in the 4-position and the 4-position substituent is in the trans position relative to the carbonyl.

According to further embodiment, $R^5$ in formulas I, IA, and IB is cyclohexyl which is unsubstituted or substituted in the 4-position by OH, halogen, $C_{1-6}$-alkyl, halogenated $C_{1-6}$-alkyl, $C_{1-6}$-alkoxy, halogenated $C_{1-6}$-alkoxy, cyano, nitro, —$NH_2$, —$NH(C_{1-4}$ alkyl), or —$N(C_{1-4}$ alkyl$)_2$.

According to further embodiment, in formulas I, IA, and IB, X is —$NR^6$—CO—$R^5$ and $R^5$ is cyclohexyl which is unsubstituted or substituted in the 4-position by OH, halogen, $C_{1-6}$-alkyl, halogenated $C_{1-6}$-alkyl, $C_{1-6}$-alkoxy, halogenated $C_{1-6}$-alkoxy, cyano, nitro, —$NH_2$, —$NH(C_{1-4}$ alkyl), or —$N(C_{1-4}$ alkyl$)_2$, wherein the 4-position substituent is in the trans position relative to the carbonyl group.

According to further embodiment, $R^6$ in formulas I, IA, and IB is $R^6$ is cyclohexyl which is substituted one or more times by OH, halogen, $C_{1-6}$-alkyl, or $C_{1-6}$-alkoxy.

According to further embodiment, $R^6$ in formulas I, IA, and IB is cyclohexyl which is substituted in the 4-position.

According to further embodiment, $R^6$ in formulas I, IA, and IB is cyclohexyl which is substituted in the 4-position and the 4-position substituent is in the trans position relative to the amino group.

According to further embodiment, $R^6$ in formulas I, IA, and IB is cyclohexyl which is substituted in the 4-position by OH or $C_{1-6}$-alkoxy.

According to further embodiment, $R^6$ in formulas I, IA, and IB is

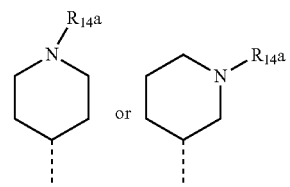

and $R^{14a}$ is $C_{1-6}$-alkyl, halogenated $C_{1-6}$-alkyl, $C_{1-6}$-alkyl-CO—, —$S(O)_{0-2}C_{1-4}$ alkyl, heteroaryl or $C_{6-14}$-aryl.

According to further embodiment, $R^6$ in formulas I, IA, and IB is

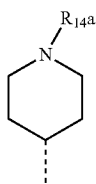

and $R^{14a}$ is $C_{1-6}$-alkyl, halogenated $C_{1-6}$-alkyl, $C_{1-6}$-alkyl-CO—, —S(O)$_{0-2}$C$_{1-4}$ alkyl, heteroaryl or $C_{6-14}$-aryl.

According to further embodiment, $R^6$ in formulas I, IA, and IB is

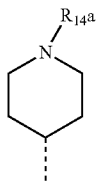

and $R^{14a}$ is methyl, ethyl, propyl or isopropyl.

According to further embodiment, in formulas I, or IB, $R^6$ is cyclohexyl which is substituted in the 4-position by OH, $C_{1-6}$-alkyl, or $C_{1-6}$-alkoxy wherein the 4-position substituent is in the trans position relative to the amino group.

According to further embodiment, in formulas I, or IB, $R^6$ is cyclohexyl which is substituted in the 4-position by OH, $C_{1-6}$-alkyl, or $C_{1-6}$-alkoxy wherein the 4-position substituent is in the trans position relative to the amino group, and $R^5$ is cyclohexyl which is unsubstituted or substituted in the 4-position by OH, halogen, $C_{1-6}$-alkyl, halogenated $C_{1-6}$-alkyl, $C_{1-6}$-alkoxy, halogenated $C_{1-6}$-alkoxy, cyano, nitro, —NH$_2$, —NH(C$_{1-4}$ alkyl), or —N(C$_{1-4}$ alkyl)$_2$, wherein the 4-position substituent is in the trans position relative to the carbonyl group.

In accordance with a preferred embodiment of the invention, the compounds of the present invention are selected from the compounds of formula (IB) and pharmaceutically acceptable salts thereof, wherein:
$R^1$ is $C_{1-6}$ alkyl or $C_{3-6}$ cycloalkyl which in each case is unsubstituted or substituted one or more times by —NH$_2$, NHCH$_3$, N(CH$_3$)$_2$, or hydroxyl;
$R^5$ is cyclohexyl which is unsubstituted or substituted one or more times by OH, $C_{1-4}$-alkyl, and/or $C_{1-4}$-alkoxy;
$R^6$ is cyclohexyl which is substituted one or more times by OH, Hal (e.g., F), $C_{1-4}$-alkoxy, $C_{1-4}$-alkyl, $C_{1-4}$-alkyl-CO—NH—, $C_{1-4}$-alkyl-CO—N(C$_{1-4}$-alkyl)-, or triazolyl;
Y is COOR$^7$; and
$R^7$ is H, $C_{1-12}$ alkyl or $C_{6-14}$ aryl.

In accordance with a preferred embodiment of the invention, the compounds of the present invention are selected from the compounds of formula (IB) and pharmaceutically acceptable salts thereof, wherein:
$R^1$ is $C_{1-6}$ alkyl or $C_{3-6}$ cycloalkyl;
$R^5$ is cyclohexyl which is unsubstituted or substituted one or more times by OH, $C_{1-4}$-alkyl, and/or $C_{1-4}$-alkoxy;
$R^6$ is cyclohexyl which is substituted one or more times by OH, Hal (e.g., F), $C_{1-4}$-alkoxy, $C_{1-4}$-alkyl, $C_{1-4}$-alkyl-CO—NH—, $C_{1-4}$-alkyl-CO—N(C$_{1-4}$-alkyl)-, or triazolyl;
Y is COOR$^7$; and
$R^7$ is H, $C_{1-12}$ alkyl or $C_{6-14}$ aryl.

In accordance with another preferred embodiment of the invention, the compounds of the present invention are selected from the compounds of formula (IB) and pharmaceutically acceptable salts thereof, wherein:
$R^1$ is $C_{1-6}$ alkyl which is unsubstituted or substituted one or more times by —NH$_2$, NHCH$_3$, N(CH$_3$)$_2$, or hydroxyl;
$R^5$ is cyclohexyl which is unsubstituted or substituted in the 4-position by OH, $C_{1-4}$-alkyl, and/or $C_{1-4}$-alkoxy;
$R^6$ is cyclohexyl which is substituted in the 4-position by OH, Hal (e.g., F), $C_{1-4}$-alkoxy, $C_{1-4}$-alkyl, $C_{1-4}$-alkyl-CO—NH—, $C_{1-4}$-alkyl-CO—N(C$_{1-4}$-alkyl)-, or triazolyl;
Y is COOR$^7$; and
$R^7$ is H, $C_{1-12}$ alkyl or $C_{6-14}$ aryl.

In accordance with another preferred embodiment of the invention, the compounds of the present invention are selected from the compounds of formula (IB) and pharmaceutically acceptable salts thereof, wherein:
$R^1$ is $C_{1-6}$ alkyl which is unsubstituted or substituted one or more times by —NH$_2$, NHCH$_3$, N(CH$_3$)$_2$, or hydroxyl;
$R^5$ is cyclohexyl which is unsubstituted or substituted in the 4-position by OH, $C_{1-4}$-alkyl, and/or $C_{1-4}$-alkoxy;
$R^6$ is cyclohexyl which is substituted in the 4-position by OH, Hal (e.g., F), $C_{1-4}$-alkoxy, $C_{1-4}$-alkyl, $C_{1-4}$-alkyl-CO—NH—, $C_{1-4}$-alkyl-CO—N(C$_{1-4}$-alkyl)-, or triazolyl;
Y is COOR$^7$; and
$R^7$ is H, $C_{1-12}$ alkyl or $C_{6-14}$ aryl.

In accordance with another preferred embodiment of the invention, the compounds of the present invention are selected from the compounds of formula (IB) and pharmaceutically acceptable salts thereof, wherein:
$R^1$ is $C_{1-6}$ alkyl which is unsubstituted or substituted one or more times by —NH$_2$, NHCH$_3$, N(CH$_3$)$_2$, or hydroxyl;
$R^5$ is cyclohexyl which is unsubstituted or substituted one or more times by OH, $C_{1-4}$-alkyl, or $C_{1-4}$-alkoxy;
$R^6$ is cyclohexyl which is substituted one or more times by OH, F, $C_{1-4}$-alkoxy, $C_{1-4}$-alkyl, or halogenated $C_{1-4}$-alkyl;
Y is COOR$^7$; and
$R^7$ is H or $C_{1-4}$ alkyl.

In accordance with another preferred embodiment of the invention, the compounds of the present invention are selected from the compounds of formula (IB) and pharmaceutically acceptable salts thereof, wherein:
$R^1$ is $C_{1-6}$ alkyl;
$R^5$ is cyclohexyl which is unsubstituted or substituted one or more times by OH, $C_{1-4}$-alkyl, or $C_{1-4}$-alkoxy;
$R^6$ is cyclohexyl which is substituted one or more times by OH, F, $C_{1-4}$-alkoxy, or $C_{1-4}$-alkyl;
Y is COOR$^7$; and
$R^7$ is H or $C_{1-4}$ alkyl.

In accordance with another preferred embodiment of the invention, the compounds of the present invention are selected from the compounds of formula (IB) and pharmaceutically acceptable salts thereof, wherein:
$R^1$ is $C_{1-6}$ alkyl or $C_{3-6}$ cycloalkyl which in each case is unsubstituted or substituted one or more times by —NH$_2$, NHCH$_3$, N(CH$_3$)$_2$, or hydroxyl;
$R^5$ is cyclohexyl which is unsubstituted or substituted one or more times by OH, $C_{1-4}$-alkyl, or $C_{1-4}$-alkoxy;
$R^6$ is cyclohexyl which is substituted one or more times by OH, F, $C_{1-4}$-alkoxy, or $C_{1-4}$-alkyl;
Y is COOR$^7$; and
$R^7$ is H or $C_{1-4}$ alkyl.

In accordance with another preferred embodiment of the invention, the compounds of the present invention are selected from the compounds of formula (IB) and pharmaceutically acceptable salts thereof, wherein:
$R^1$ is $C_{1-6}$ alkyl or $C_{3-6}$ cycloalkyl;
$R^5$ is cyclohexyl which is unsubstituted or substituted one or more times by OH, $C_{1-4}$-alkyl, or $C_{1-4}$-alkoxy;

$R^6$ is cyclohexyl which is substituted one or more times by OH, F, $C_{1-4}$-alkoxy, or $C_{1-4}$-alkyl;
Y is $COOR^7$; and
$R^7$ is H or $C_{1-4}$ alkyl.

In accordance with another preferred embodiment of the invention, the compounds of the present invention are selected from the compounds of formula (IB) and pharmaceutically acceptable salts thereof, wherein:
$R^1$ is methyl, ethyl, propyl, isopropyl, butyl, sec.-butyl, tert.-butyl, cyclopropyl, cyclobutyl, cyclopentyl, or cyclohexyl which in each case is unsubstituted or substituted one or more times by —$NH_2$, $NHCH_3$, $N(CH_3)_2$, or hydroxyl;
$R^5$ is cyclohexyl which is unsubstituted or substituted one or more times by OH, $C_{1-4}$-alkyl, or $C_{1-4}$-alkoxy;
$R^6$ is cyclohexyl which is substituted one or more times by OH, F, $C_{1-4}$-alkoxy, $C_{1-4}$-alkyl, or halogenated $C_{1-4}$-alkyl;
Y is $COOR^7$; and
$R^7$ is H or $C_{1-4}$ alkyl.

In accordance with another preferred embodiment of the invention, the compounds of the present invention are selected from the compounds of formula (IB) and pharmaceutically acceptable salts thereof, wherein:
$R^1$ is methyl, ethyl, propyl, isopropyl, butyl, sec.-butyl, tert.-butyl, cyclopropyl, cyclobutyl, cyclopentyl, or cyclohexyl;
$R^5$ is cyclohexyl which is unsubstituted or substituted one or more times by OH, $C_{1-4}$-alkyl, or $C_{1-4}$-alkoxy;
$R^6$ is cyclohexyl which is substituted one or more times by OH, F, $C_{1-4}$-alkoxy, $C_{1-4}$-alkyl, or halogenated $C_{1-4}$-alkyl;
Y is $COOR^7$; and
$R^7$ is H or $C_{1-4}$ alkyl.

In accordance with another preferred embodiment of the invention, the compounds of the present invention are selected from the compounds of formula (IB) and pharmaceutically acceptable salts thereof, wherein:
$R^1$ is methyl, ethyl, propyl, isopropyl, butyl, sec.-butyl, tert.-butyl, cyclopropyl, cyclobutyl, cyclopentyl, or cyclohexyl which in each case is unsubstituted or substituted one or more times by —$NH_2$, $NHCH_3$, $N(CH_3)_2$, or hydroxyl —$NH_2$, $NHCH_3$, $N(CH_3)_2$, or hydroxyl;
$R^5$ is cyclohexyl which is unsubstituted or substituted one or more times by OH, $C_{1-4}$-alkyl, or $C_{1-4}$-alkoxy;
$R^6$ is cyclohexyl which is substituted one or more times by OH, F, $C_{1-4}$-alkoxy, $C_{1-4}$-alkyl, or halogenated $C_{1-4}$-alkyl;
Y is COOH.

In accordance with another preferred embodiment of the invention, the compounds of the present invention are selected from the compounds of formula (IB) and pharmaceutically acceptable salts thereof, wherein:
$R^1$ is methyl, ethyl, propyl, isopropyl, butyl, sec.-butyl, tert.-butyl, cyclopropyl, cyclobutyl, cyclopentyl, or cyclohexyl;
$R^5$ is cyclohexyl which is unsubstituted or substituted one or more times by OH, $C_{1-4}$-alkyl, or $C_{1-4}$-alkoxy;
$R^6$ is cyclohexyl which is substituted one or more times by OH, F, $C_{1-4}$-alkoxy, $C_{1-4}$-alkyl, or halogenated $C_{1-4}$-alkyl;
Y is COOH.

In accordance with another preferred embodiment of the invention, the compounds of the present invention are selected from the compounds of formula (IB) and pharmaceutically acceptable salts thereof, wherein:
$R^1$ is $C_{1-6}$ alkyl or $C_{3-6}$ cycloalkyl which in each case is unsubstituted or substituted one or more times by —$NH_2$, $NHCH_3$, $N(CH_3)_2$, or hydroxyl;
$R^5$ is cyclohexyl which is unsubstituted or substituted one or more times by OH, $C_{1-4}$-alkyl, and/or $C_{1-4}$-alkoxy;
$R^6$ is

[structure: piperidine with $R_{14a}$ on N, or piperidine with $R_{14a}$ on N];

$R^{14a}$ is $C_{1-6}$-alkyl, halogenated $C_{1-6}$-alkyl, $C_{1-6}$-alkyl-CO—, —$S(O)_{0-2}C_{1-4}$ alkyl, heteroaryl or $C_{6-14}$-aryl;
Y is $COOR^7$; and
$R^7$ is H, $C_{1-12}$ alkyl or $C_{6-14}$ aryl.

In accordance with another preferred embodiment of the invention, the compounds of the present invention are selected from the compounds of formula (IB) and pharmaceutically acceptable salts thereof, wherein:
$R^1$ is $C_{1-6}$ alkyl or $C_{3-6}$ cycloalkyl;
$R^5$ is cyclohexyl which is unsubstituted or substituted one or more times by OH, $C_{1-4}$-alkyl, and/or $C_{1-4}$-alkoxy;
$R^6$ is

[structure: piperidine with $R_{14a}$ on N, or piperidine with $R_{14a}$ on N];

$R^{14a}$ is $C_{1-6}$-alkyl, halogenated $C_{1-6}$-alkyl, $C_{1-6}$-alkyl-CO—, —$S(O)_{0-2}C_{1-4}$ alkyl, heteroaryl or $C_{6-14}$-aryl;
Y is $COOR^7$; and
$R^7$ is H, $C_{1-12}$ alkyl or $C_{6-14}$ aryl.

In accordance with another preferred embodiment of the invention, the compounds of the present invention are selected from the compounds of formula (IB) and pharmaceutically acceptable salts thereof, wherein:
$R^1$ is $C_{1-6}$ alkyl or $C_{3-6}$ cycloalkyl which in each case is unsubstituted or substituted one or more times by —$NH_2$, $NHCH_3$, $N(CH_3)_2$, or hydroxyl;
$R^5$ is cyclohexyl which is unsubstituted or substituted one or more times by OH, $C_{1-4}$-alkyl, and/or $C_{1-4}$-alkoxy;
$R^6$ is

[structure: piperidine with $R_{14a}$ on N, or piperidine with $R_{14a}$ on N];

$R^{14a}$ is $C_{1-6}$-alkyl or halogenated $C_{1-6}$-alkyl;
Y is $COOR^7$; and
$R^7$ is H, $C_{1-12}$ alkyl or $C_{6-14}$ aryl.

In accordance with another preferred embodiment of the invention, the compounds of the present invention are selected from the compounds of formula (IB) and pharmaceutically acceptable salts thereof, wherein:
$R^1$ is $C_{1-6}$ alkyl or $C_{3-6}$ cycloalkyl;
$R^5$ is cyclohexyl which is unsubstituted or substituted one or more times by OH, $C_{1-4}$-alkyl, and/or $C_{1-4}$-alkoxy;

R⁶ is

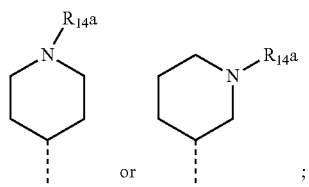

R$^{14a}$ is C$_{1-6}$-alkyl or halogenated C$_{1-6}$-alkyl;
Y is COOR$^7$; and
R$^7$ is H, C$_{1-12}$ alkyl or C$_{6-14}$ aryl.

In accordance with another preferred embodiment of the invention, the compounds of the present invention are selected from the compounds of formula (IB) and pharmaceutically acceptable salts thereof, wherein:
R$^1$ is C$_{1-6}$ alkyl or C$_{3-6}$ cycloalkyl which in each case is unsubstituted or substituted one or more times by —NH$_2$, NHCH$_3$, N(CH$_3$)$_2$, or hydroxyl;
R$^5$ is cyclohexyl which is unsubstituted or substituted one or more times by OH, C$_{1-4}$-alkyl, and/or C$_{1-4}$-alkoxy;
R$^6$ is

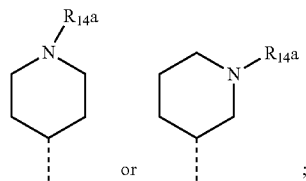

R$^{14a}$ is C$_{1-6}$-alkyl;
Y is COOR$^7$; and
R$^7$ is H, C$_{1-12}$ alkyl or C$_{6-14}$ aryl.

In accordance with another preferred embodiment of the invention, the compounds of the present invention are selected from the compounds of formula (IB) and pharmaceutically acceptable salts thereof, wherein:
R$^1$ is C$_{1-6}$ alkyl or C$_{3-6}$ cycloalkyl;
R$^5$ is cyclohexyl which is unsubstituted or substituted one or more times by OH, C$_{1-4}$-alkyl, and/or C$_{1-4}$-alkoxy;
R$^6$ is

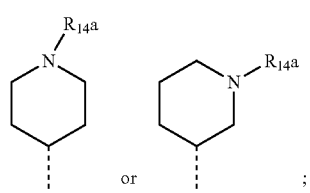

R$^{14a}$ is C$_{1-6}$-alkyl;
Y is COOR$^7$; and
R$^7$ is H, C$_{1-12}$ alkyl or C$_{6-14}$ aryl.

In accordance with another preferred embodiment of the invention, the compounds of the present invention are selected from the compounds of formula (IB) and pharmaceutically acceptable salts thereof, wherein:
R$^1$ is C$_{1-6}$ alkyl or C$_{3-6}$ cycloalkyl which in each case is unsubstituted or substituted one or more times by —NH$_2$, NHCH$_3$, N(CH$_3$)$_2$, or hydroxyl;
R$^5$ is cyclohexyl which is unsubstituted or substituted one or more times by OH, C$_{1-4}$-alkyl, and/or C$_{1-4}$-alkoxy;
R$^6$ is

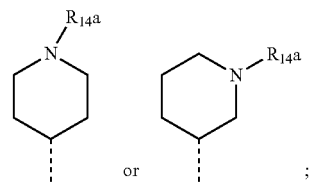

R$^{14a}$ is methyl, ethyl, propyl, isopropyl, butyl, sec.-butyl, or tert.-butyl;
Y is COOR$^7$; and
R$^7$ is H, C$_{1-12}$ alkyl or C$_{6-14}$ aryl.

In accordance with another preferred embodiment of the invention, the compounds of the present invention are selected from the compounds of formula (IB) and pharmaceutically acceptable salts thereof, wherein:
R$^1$ is C$_{1-6}$ alkyl or C$_{3-6}$ cycloalkyl;
R$^5$ is cyclohexyl which is unsubstituted or substituted one or more times by OH, C$_{1-4}$-alkyl, and/or C$_{1-4}$-alkoxy;
R$^6$ is

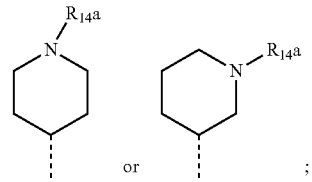

R$^{14a}$ is methyl, ethyl, propyl, isopropyl, butyl, sec.-butyl, or tert.-butyl;
Y is COOR$^7$; and
R$^7$ is H, C$_{1-12}$ alkyl or C$_{6-14}$ aryl.

According to an aspect of the invention, the compounds of the invention are selected from:
5-(3,3-DIMETHYL-BUT-1-YNYL)-3-[(TRANS-4-HYDROXY-CYCLOHEXYL)-(TRANS-4-METHYL-CYCLOHEXANECARBONYL)-AMINO]-THIOPHENE-2-CARBOXYLIC ACID;
5-(3,3-DIMETHYL-BUT-1-YNYL)-3-[(TRANS-4-METHOXY-CYCLOHEXYL)-(TRANS-4-METHYL-CYCLOHEXANECARBONYL)-AMINO]-THIOPHENE-2-CARBOXYLIC ACID;
5-(3,3-DIMETHYL-BUT-1-YNYL)-3-[(TRANS-4-METHYL-CYCLOHEXANECARBONYL)-(CIS-4-[1,2,4]TRIAZOL-1-YL-CYCLOHEXYL)-AMINO]-THIOPHENE-2-CARBOXYLIC ACID;
5-(3,3-DIMETHYL-BUT-1-YNYL)-3-[(TRANS-4-METHYL-CYCLOHEXANECARBONYL)-(TRANS-4-[1,2,4]TRIAZOL-1-YL-CYCLOHEXYL)-AMINO]-THIOPHENE-2-CARBOXYLIC ACID;
5-(3,3-DIMETHYL-BUT-1-YNYL)-3-[CIS-4-HYDROXY-CYCLOHEXYL)-(TRANS-4-METHYL-CYCLOHEXANECARBONYL)-AMINO]-THIOPHENE-2-CARBOXYLIC ACID;
5-(3,3-DIMETHYL-BUT-1-YNYL)-3-[(TRANS-4-METHYL-CYCLOHEXANECARBONYL)-(1-METHYL-PIPERIDIN-4-YL)-AMINO]-THIOPHENE-2-CARBOXYLIC ACID; HYDROCHLORIDE;

5-(3,3-DIMETHYL-BUT-1-YNYL)-3-[(TRANS-4-ME-
THYL-CYCLOHEXANECARBONYL)-(4-CIS-[1,2,3]
TRIAZOL-1-YL-CYCLOHEXYL)-AMINO]-
THIOPHENE-2-CARBOXYLIC ACID
5-(3,3-DIMETHYL-BUT-1-YNYL)-3-[(TRANS-4-ME-
THYL-CYCLOHEXANECARBONYL)-(TRANS-4-[1,
2,3]TRIAZOL-1-YL-CYCLOHEXYL)-AMINO]-
THIOPHENE-2-CARBOXYLIC ACID; and
5-(3,3-DIMETHYL-BUT-1-YNYL)-3-[(TRANS-4-
FLUORO-CYCLOHEXYL)-(TRANS-4-METHYL-CY-
CLOHEXANECARBONYL)-AMINO]-THIOPHENE-
2-CARBOXYLIC ACID.

In one embodiment, the present invention provides a pharmaceutical composition comprising at least one compound according to the invention described herein and at least one pharmaceutically acceptable carrier or excipient.

In one embodiment, the present invention provides a pharmaceutical composition comprising at least one compound according to the invention described herein and at least one compound according to the invention described herein, and further comprising administering at least one additional agent chosen from viral serine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES).

In another embodiment, there is provided a combination comprising a least one compound according to the invention described herein and one or more additional agents chosen from viral serine protease inhibitors, viral polymerase inhibitors, viral helicase inhibitors, immunomudulating agents, antioxidant agents, antibacterial agents, therapeutic vaccines, hepatoprotectant agents, antisense agent, inhibitors of HCV NS2/3 protease and inhibitors of internal ribosome entry site (IRES).

In one combination embodiment, the compound and additional agent are administered sequentially.

In another combination embodiment, the compound and additional agent are administered simultaneously.

The combinations referred to above may conveniently be presented for use in the form of a pharmaceutical formulation and thus pharmaceutical formulations comprising a combination as defined above together with a pharmaceutically acceptable carrier therefore comprise a further aspect of the invention.

The additional agents for the compositions and combinations include, for example, ribavirin, amantadine, merimepodib, Levovirin, Viramidine, and maxamine.

The term "viral serine protease inhibitor" as used herein means an agent that is effective to inhibit the function of the viral serine protease including HCV serine protease in a mammal. Inhibitors of HCV serine protease include, for example, those compounds described in WO 99/07733 (Boehringer Ingelheim), WO 99/07734 (Boehringer Ingelheim), WO 00/09558 (Boehringer Ingelheim), WO 00/09543 (Boehringer Ingelheim), WO 00/59929 (Boehringer Ingelheim), WO 02/060926 (BMS), WO 2006039488 (Vertex), WO 2005077969 (Vertex), WO 2005035525 (Vertex), WO 2005028502 (Vertex) WO 2005007681 (Vertex), WO 2004092162 (Vertex), WO 2004092161 (Vertex), WO 2003035060 (Vertex), of WO 03/087092 (Vertex), WO 02/18369 (Vertex), or WO98/17679 (Vertex).

The term "viral polymerase inhibitors" as used herein means an agent that is effective to inhibit the function of a viral polymerase including an HCV polymerase in a mammal. Inhibitors of HCV polymerase include non-nucleosides, for example, those compounds described in: WO 03/010140 (Boehringer Ingelheim), WO 03/026587 (Bristol Myers Squibb); WO 02/100846 A1, WO 02/100851 A2, WO 01/85172 A1 (GSK), WO 02/098424 A1 (GSK), WO 00/06529 (Merck), WO 02/06246 A1 (Merck), WO 01/47883 (Japan Tobacco), WO 03/000254 (Japan Tobacco) and EP 1 256 628 A2 (Agouron).

Furthermore other inhibitors of HCV polymerase also include nucleoside analogs, for example, those compounds described in: WO 01/90121 A2 (Idenix), WO 02/069903 A2 (Biocryst Pharmaceuticals Inc.), and WO 02/057287 A2(Merck/Isis) and WO 02/057425 A2 (Merck/Isis).

Specific examples of nucleoside inhibitors of an HCV polymerase, include R1626/R1479 (Roche), R7128(Roche), MK-0608 (Merck), R1656, (Roche-Pharmasset) and Valopicitabine (Idenix).

Specific examples of inhibitors of an HCV polymerase, include JTK-002/003 and JTK-109 (Japan Tobacco), HCV-796 (Viropharma), GS-9190(Gilead), and PF-868,554 (Pfizer).

The term "viral helicase inhibitors" as used herein means an agent that is effective to inhibit the function of a viral helicase including a Flaviviridae helicase in a mammal.

"Immunomodulatory agent" as used herein means those agents that are effective to enhance or potentiate the immune system response in a mammal. Immunomodulatory agents include, for example, class I interferons (such as α-, β-, δ- and Ω-interferons, Σ-interferons, consensus interferons and asialo-interferons), class II interferons (such as γ-interferons) and pegylated interferons.

The term "class I interferon" as used herein means an interferon selected from a group of interferons that all bind to receptor type 1. This includes both naturally and synthetically produced class I interferons. Examples of class I interferons include α-, β-, δ- and Ω-interferons, τ-interferons, consensus interferons and asialo-interferons. The term "class II interferon" as used herein means an interferon selected from a group of interferons that all bind to receptor type II. Examples of class II interferons include γ-interferons.

Antisense agents include, for example, ISIS-14803.

Specific examples of inhibitors of HCV NS3 protease, include BILN-2061 (Boehringer Ingelheim) SCH-6 and SCH-503034/Boceprevir(Schering-Plough), VX-950/telaprevir(Vertex) and ITMN-B (InterMune), GS 9132 (Gilead), TMC-435350(Tibotec/Medivir), ITMN-191 (InterMune), MK-7009 (Merck).

Inhibitor internal ribosome entry site (IRES) include ISIS-14803 (ISIS Pharmaceuticals) and those compounds described in WO 2006019831 (PTC therapeutics).

In one embodiment, the additional agent is interferon α, ribavirin, silybum marianum, interleukine-12, amantadine, ribozyme, thymosin, N-acetyl cysteine or cyclosporin.

In one embodiment, the additional agent is interferon α1A, interferon α1B, interferon α2A, or interferon α2B.

Interferon is available in pegylated and non pegylated forms. Pegylated interferons include PEGASYS™ and Peg-Intron™.

The recommended dose of PEGASYS™ monotherapy for chronic hepatitis C is 180 mg (1.0 mL vial or 0.5 mL prefilled syringe) once weekly for 48 weeks by subcutaneous administration in the abdomen or thigh.

The recommended dose of PEGASYS™ when used in combination with ribavirin for chronic hepatitis C is 180 mg (1.0 mL vial or 0.5 mL prefilled syringe) once weekly.

The daily dose of Ribavirin is 800 mg to 1200 mg administered orally in two divided doses. The dose should be individualized to the patient depending on baseline disease characteristics (e.g., genotype), response to therapy, and tolerability of the regimen.

The recommended dose of PEG-Intron™ regimen is 1.0 mg/kg/week subcutaneously for one year. The dose should be administered on the same day of the week.

When administered in combination with ribavirin, the recommended dose of PEG-Intron is 1.5 micrograms/kg/week.

In one embodiment, viral serine protease inhibitor is a flaviviridae serine protease inhibitor.

In one embodiment, viral polymerase inhibitor is a flaviviridae polymerase inhibitor.

In one embodiment, viral helicase inhibitor is a flaviviridae helicase inhibitor.

In further embodiments:
viral serine protease inhibitor is HCV serine protease inhibitor;
viral polymerase inhibitor is HCV polymerase inhibitor;
viral helicase inhibitor is HCV helicase inhibitor.

In one embodiment, the present invention provides a method for treating or preventing a Flaviviridae viral infection in a host comprising administering to the host a therapeutically effective amount of at least one compound according to formula I.

In one embodiment, the viral infection is chosen from Flavivirus infections.

In one embodiment, the Flavivirus infection is Hepatitis C virus (HCV), bovine viral diarrhea virus (BVDV), hog cholera virus, dengue fever virus, Japanese encephalitis virus or yellow fever virus.

In one embodiment, the Flaviviridea viral infection is hepatitis C viral infection (HCV).

In one embodiment, the present invention provides a method for treating or preventing a Flaviviridae viral infection in a host comprising administering to the host a therapeutically effective amount of at least one compound according to the invention described herein, and further comprising administering at least one additional agent chosen from viral serine protease inhibitors, viral polymerase inhibitors, viral helicase inhibitors, immunomudulating agents, antioxidant agents, antibacterial agents, therapeutic vaccines, hepatoprotectant agents, antisense agents, inhibitors of HCV NS2/3 protease and inhibitors of internal ribosome entry site (IRES).

In one embodiment, there is provided a method for inhibiting or reducing the activity of viral polymerase in a host comprising administering a therapeutically effective amount of a compound according to the invention described herein.

In one embodiment, there is provided a method for inhibiting or reducing the activity of viral polymerase in a host comprising administering a therapeutically effective amount of a compound according to the invention described herein and further comprising administering one or more viral polymerase inhibitors.

In one embodiment, viral polymerase is a Flaviviridae viral polymerase.

In one embodiment, viral polymerase is a RNA-dependant RNA-polymerase.

In one embodiment, viral polymerase is HCV polymerase.

The combinations referred to above may conveniently be presented for use in the form of a pharmaceutical formulation and thus pharmaceutical formulations comprising a combination as defined above together with a pharmaceutically acceptable carrier therefore comprise a further aspect of the invention.

The individual components for use in the method of the present invention or combinations of the present invention may be administered either sequentially or simultaneously in separate or combined pharmaceutical formulations.

In one embodiment, the present invention provides the use of a compound according to the invention described herein for treating or preventing Flaviviridae viral infection in a host.

In one embodiment, the present invention provides the use of a compound according to the invention described herein for the manufacture of a medicament for treating or preventing a viral Flaviviridae infection in a host.

In one embodiment, the present invention provides the use of a compound according to the invention described herein for inhibiting or reducing the activity of viral polymerase in a host.

It will be appreciated by those skilled in the art that the compounds in accordance with the present invention can exists as stereoisomers (for example, optical (+ and −), geometrical (cis and trans) and conformational isomers (axial and equatorial). All such stereoisomers are included in the scope of the present invention.

It will be appreciated by those skilled in the art that the compounds in accordance with the present invention can contain a chiral center. The compounds of formula may thus exist in the form of two different optical isomers (i.e. (+) or (−) enantiomers). All such enantiomers and mixtures thereof including racemic mixtures are included within the scope of the invention. The single optical isomer or enantiomer can be obtained by method well known in the art, such as chiral HPLC, enzymatic resolution and chiral auxiliary.

In one embodiment, the compounds of the present invention are provided in the form of a single enantiomer at least 95%, at least 97% and at least 99% free of the corresponding enantiomer.

In a further embodiment the compound of the present invention are in the form of the (+) enantiomer at least 95% free of the corresponding (−) enantiomer.

In a further embodiment the compound of the present invention are in the form of the (+) enantiomer at least 97% free of the corresponding (−) enantiomer.

In a further embodiment the compound of the present invention are in the form of the (+) enantiomer at least 99% free of the corresponding (−) enantiomer.

In a further embodiment, the compounds of the present invention are in the form of the (−) enantiomer at least 95% free of the corresponding (+) enantiomer.

In a further embodiment the compound of the present invention are in the form of the (−) enantiomer at least 97% free of the corresponding (+) enantiomer.

In a further embodiment the compound of the present invention are in the form of the (−) enantiomer at least 99% free of the corresponding (+) enantiomer.

There is also provided pharmaceutically acceptable salts of the compounds of the present invention. By the term pharmaceutically acceptable salts of compounds are meant those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toleune-p-sulphonic, tartaric, acetic, trifluoroacetic, citric, methane sulphonic, formic, benzoic, malonic, naphthalene-2-sulphonic and benzenesulphonic acids. Other acids such as oxalic, while not themselves pharmaceutically acceptable, may be useful as intermediates in obtaining the compounds of the invention and their pharmaceutically acceptable acid addition salts.

Salts derived from amino acids are also included (e.g. L-arginine, L-Lysine).

Salts derived from appropriate bases include alkali metals (e.g. sodium, lithium, potassium), alkaline earth metals (e.g. calcium, magnesium), ammonium, $NR_4+$ (where R is $C_{1-4}$ alkyl) salts, choline and tromethamine.

A reference hereinafter to a compound according to the invention includes that compound and its pharmaceutically acceptable salts.

In one embodiment of the invention, the pharmaceutically acceptable salt is a sodium salt.

In one embodiment of the invention, the pharmaceutically acceptable salt is a lithium salt.

In one embodiment of the invention, the pharmaceutically acceptable salt is a potassium salt.

In one embodiment of the invention, the pharmaceutically acceptable salt is a tromethamine salt.

In one embodiment of the invention, the pharmaceutically acceptable salt is an L-arginine salt.

It will be appreciated by those skilled in the art that the compounds in accordance with the present invention can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

It will further be appreciated by those skilled in the art that the compounds in accordance with the present invention can exist in different solvate forms, for example hydrates. Solvates of the compounds of the invention may also form when solvent molecules are incorporated into the crystalline lattice structure of the compound molecule during the crystallization process.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

The term "alkyl" represents a linear, branched or cyclic hydrocarbon moiety. The terms "alkenyl" and "alkynyl" represent a linear, branched or cyclic hydrocarbon moiety which has one or more double bonds or triple bonds in the chain. Examples of alkyl, alkenyl, and alkynyl groups include but are not limited to methyl, ethyl, propyl, isopropyl, butyl, isobutyl, sec-butyl, tert-butyl, pentyl, isopentyl, neopentyl, tert-pentyl, hexyl, isohexyl, neohexyl, allyl, vinyl, acetylenyl, ethylenyl, propenyl, isopropenyl, butenyl, isobutenyl, hexenyl, butadienyl, pentenyl, pentadienyl, hexenyl, hexadienyl, hexatrienyl, heptenyl, heptadienyl, heptatrienyl, octenyl, octadienyl, octatrienyl, octatetraenyl, propynyl, butynyl, pentynyl, hexynyl, cyclopropyl, cyclobutyl, cyclohexenyl, cyclohexdienyl and cyclohexyl. Where indicated the "alkyl," "alkenyl," and "alkynyl" can be optionally substituted such as in the case of haloalkyls in which one or more hydrogen atom is replaced by a halogen, e.g., an alkylhalide. Examples of haloalkyls include but are not limited to trifluoromethyl, difluoromethyl, fluoromethyl, trichloromethyl, dichloromethyl, chloromethyl, trifluoroethyl, difluoroethyl, fluoroethyl, trichloroethyl, dichloroethyl, chloroethyl, chlorofluoromethyl, chlorodifluoromethyl, dichlorofluoroethyl. Aside from halogens, where indicated, the alkyl, alkenyl or alkynyl groups can also be optionally substituted by, for example, oxo, —$NR_dR_e$, —$CONR_dR_e$, =NO—$R_e$, $NR_dCOR_e$, carboxy, —$C(=NR_d)NR_eR_f$, azido, cyano, $C_{1-6}$ alkyloxy, $C_{2-6}$ alkenyloxy, $C_{2-6}$ alkynyloxy, —$N(R_d)C(=NR_e)$—$NR_fR_g$, hydroxyl, nitro, nitroso, —$N(R_h)CONR_iR_j$, $S(O)_{0-2}R_a$, $C(O)R_a$, $C(O)OR_a$, $NR_aC(O)R_b$, $SO_2NR_aR_b$, $NR_aSO_2R_b$, $NR_aSO_2NR_bR_c$, $CR_aN=OR_b$, and/or $NR_aCOOR_b$, wherein $R_a$-$R_j$ are each independently H, $C_{1-4}$ alkyl, $C_{2-4}$ alkenyl or $C_{2-4}$ alkynyl.

The terms "cycloalkyl", and "cycloalkenyl" represent a cyclic hydrocarbon alkyl or alkenyl, respectively, and are meant to include monocyclic (e.g., cyclohexyl), spiro (e.g., spiro[2.3]hexanyl), fused (e.g., bicyclo[4.4.0]decanyl), and bridged (e.g., bicyclo[2.2.1]heptanyl) hydrocarbon moieties.

The terms "alkoxy," "alkenyloxy," and "alkynyloxy" represent an alkyl, alkenyl or alkynyl moiety, respectively, which is covalently bonded to the adjacent atom through an oxygen atom. Like the alkyl, alkenyl and alkynyl groups, where indicated the alkoxy, alkenyloxy and alkynyloxy groups can also be optionally substituted. Examples include but are not limited to methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy, trifluoromethoxy and neohexyloxy. The alkoxy, alkenyloxy, and alkynyloxy groups can be optionally substituted by, for example, halogens, oxo, —$NR_dR_e$, —$CONR_dR_e$, —$NR_dCOR_e$, carboxy, —$C(=NR_d)NR_eR_f$, azido, cyano, —$N(R_d)C(=NR_e)NR_fR_g$, hydroxyl, nitro, nitroso, $C_{1-6}$ alkyl, $C_{2-6}$ alkenyl, $C_{2-6}$ alkynyl, —$N(R_h)CONR_iR_j$, $S(O)_{0-2}R_a$, $C(O)R_a$, $C(O)OR_a$, =NO—$R_e$, $NR_aC(O)R_b$, $SO_2NR_aR_b$, $NR_aSO_2R_b$, $NR_aSO_2NR_bR_c$, $CR_aN=OR_b$, and/or $NR_aCOOR_b$, wherein $R_a$-$R_j$ are each independently H, $C_{1-4}$ alkyl, $C_{2-4}$ alkenyl or $C_{2-4}$ alkynyl.

The term "aryl" represents a carbocyclic moiety containing at least one benzenoid-type ring (i.e., may be monocyclic or polycyclic), and which where indicated may be optionally substituted with one or more substituents. Examples include but are not limited to phenyl, tolyl, dimethylphenyl, aminophenyl, anilinyl, naphthyl, anthryl, phenanthryl or biphenyl. The aryl groups can be optionally substituted by, for example, halogens, —$NR_dR_e$, —$CONR_dR_e$, —$NR_dCOR_e$, carboxy, —$C(=NR_d)NR_eR_f$, azido, cyano, —$N(R_d)C(=NR_e)NR_fR_g$, hydroxyl, nitro, nitroso, —$N(R_h)CONR_iR_j$, $C_{1-6}$ alkyl, $C_{2-6}$ alkenyl, $C_{2-6}$ alkynyl, $C_{1-6}$ alkyloxy, $C_{2-6}$ alkenyloxy, $C_{2-6}$ alkynyloxy, $S(O)_{0-2}R_a$, optionally substituted 5-12 member heteroaryl, optionally substituted 6-18 member heteroaralkyl, optionally substituted 3-12 member heterocycle, optionally substituted 4-18 member heterocycle-alkyl, $C(O)R_a$, $C(O)OR_a$, $NR_aC(O)R_b$, $SO_2NR_aR_b$, $NR_aSO_2R_b$, $NR_aSO_2NR_bR_c$, $CR_aN=OR_b$, and/or $NR_aCOOR_b$, wherein $R_a$-$R_j$ are each independently H, $C_{1-4}$ alkyl, $C_{2-4}$ alkenyl or $C_{2-4}$ alkynyl.

The term "aralkyl" represents an aryl group attached to the adjacent atom by an alkyl, alkenyl or alkynyl. Like the aryl groups, where indicated the aralkyl groups can also be optionally substituted. Examples include but are not limited to benzyl, benzhydryl, trityl, phenethyl, 3-phenylpropyl, 2-phenylpropyl, 4-phenylbutyl and naphthylmethyl. Where indicated, the aralkyl groups can be optionally substituted by, for example, halogens, —$NR_dR_e$, —$CONR_dR_e$, —$NR_dCOR_e$, carboxy, —$C(=NR_d)NR_eR_f$, azido, cyano, —$N(R_d)C(=NR_e)NR_fR_g$, hydroxyl, nitro, nitroso, —$N(R_h)CONR_iR_j$, $C_{1-6}$ alkyl, $C_{2-6}$ alkenyl, $C_{2-6}$ alkynyl, $C_{1-6}$ alkyloxy, $C_{2-6}$ alkenyloxy, $C_{2-6}$ alkynyloxy, $S(O)_{0-2}R_a$, optionally substituted 5-12 member heteroaryl, optionally substituted 6-18 member heteroaralkyl, optionally substituted 3-12 member heterocycle, optionally substituted 4-18 member heterocycle-alkyl, C(O)R$_a$, C(O)OR$_a$, NR$_a$C(O)R$_b$, SO$_2$NR$_a$R$_b$, NR$_a$SO$_2$R$_b$, NR$_a$SO$_2$NR$_b$R$_c$, CR$_a$N=OR$_b$, and/or NR$_a$COOR$_b$, wherein R$_a$-R$_j$ are each independently H, C$_{1-4}$ alkyl, C$_{2-4}$ alkenyl or C$_{2-4}$ alkynyl.

The term "heterocycle" represents an optionally substituted, non aromatic, saturated or partially saturated wherein said cyclic moiety is interrupted by at least one heteroatom selected from oxygen (O), sulfur (S) or nitrogen (N). Heterocycles may be monocyclic or polycyclic rings. Examples include but are not limited to azetidinyl, dioxolanyl, morpholinyl, morpholino, oxetanyl, piperazinyl, piperidyl, piperidino, cyclopentapyrazolyl, cyclopentaoxazinyl, cyclopentafuranyl. Where indicated, the heterocyclic groups can be optionally substituted by, for example, halogens, oxo, —NR$_d$R$_e$, —CONR$_d$R$_e$, =NO—R$_e$, —NR$_d$COR$_e$, carboxy, —C(=NR$_d$)NR$_e$R$_f$, azido, cyano, —N(R$_d$)C(=NR$_e$)NR$_f$R$_g$, hydroxyl, nitro, nitroso, —N(R$_h$)CONR$_i$R$_j$, C$_{1-6}$ alkyl, C$_{2-6}$ alkenyl, C$_{2-6}$ alkynyl, C$_{7-12}$ aralkyl, C$_{6-12}$ aryl, C$_{1-6}$ alkyloxy, C$_{2-6}$ alkenyloxy, C$_{2-6}$ alkynyloxy, S(O)$_{0-2}$R$_a$, C$_{6-10}$ aryl, C$_{6-10}$ aryloxy, C$_{7-10}$ arylalkyl, C$_{6-10}$ aryl-C$_{1-10}$ alkyloxy, C(O)R$_a$, C(O)OR$_a$, NR$_a$C(O)R$_b$, SO$_2$NR$_a$R$_b$, NR$_a$SO$_2$R$_b$, NR$_a$SO$_2$NR$_b$R$_c$, CR$_a$N=OR$_b$, and/or NR$_a$COOR$_b$, wherein R$_a$-R$_j$ are each independently H, C$_{1-4}$ alkyl, C$_{2-4}$ alkenyl or C$_{2-4}$ alkynyl.

The term "heterocycle-alkyl" represents an optionally substituted heterocycle group attached to the adjacent atom by an alkyl, alkenyl or alkynyl group. It is understood that in a 5-18 member heterocycle-alkyl moiety, the 5-18 member represent the atoms that are present in both the heterocycle moiety and the alkyl, alkenyl or alkynyl group. For example, the following groups are encompassed by a 7 member heterocycle-alkyl (* represents the attachment point):

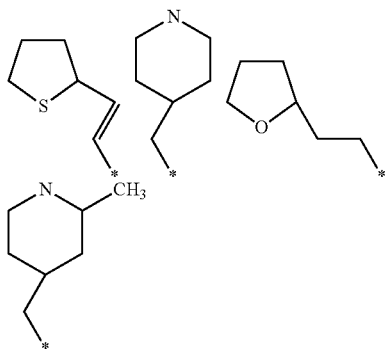

Where indicated the heterocycle-alkyl groups can be optionally substituted by, for example, halogens, oxo, —NR$_d$R$_e$, —CONR$_d$R$_e$, —NR$_d$COR$_e$, carboxy, —C(=NR$_d$)NR$_e$R$_f$, azido, cyano, —N(R$_d$)C(=NR$_e$)NR$_f$R$_g$, hydroxyl, nitro, nitroso, —N(R$_h$)CONR$_i$R$_j$, C$_{1-6}$ alkyl, C$_{2-6}$ alkenyl, C$_{2-6}$ alkynyl, C$_{1-6}$ alkyloxy, C$_{2-6}$ alkenyloxy, C$_{2-6}$ alkynyloxy, S(O)$_{0-2}$R$_a$, C$_{6-10}$ aryl, C$_{6-10}$ aryloxy, C$_{7-10}$ arylalkyl, C$_{6-10}$ aryl-C$_{1-10}$ alkyloxy, C(O)R$_a$, C(O)OR$_a$, NR$_a$C(O)R$_b$, =NO—R$_e$, SO$_2$NR$_a$R$_b$, NR$_a$SO$_2$R$_b$, NR$_a$SO$_2$NR$_b$R$_c$, CR$_a$N=OR$_b$, and/or NR$_a$COOR$_b$, wherein R$_a$-R$_j$ are each independently H, C$_{1-4}$ alkyl, C$_{2-4}$ alkenyl or C$_{2-4}$ alkynyl.

The term "heteroaryl" represents an optionally substituted aromatic cyclic moiety wherein said cyclic moiety is interrupted by at least one heteroatom selected from oxygen (O), sulfur (S) or nitrogen (N). Heteroaryls may be monocyclic or polycyclic rings. Examples include but are not limited to azepinyl, aziridinyl, azetyl, diazepinyl, dithiadiazinyl, dioxazepinyl, dithiazolyl, furanyl, isooxazolyl, isothiazolyl, imidazolyl, oxadiazolyl, oxiranyl, oxazinyl, oxazolyl, pyrazinyl, pyridazinyl, pyrimidinyl, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl, furoisoxazolyl, imidazothiazolyl, thienoisothiazolyl, thienothiazolyl, imidazopyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, benzoxazinyl, benzothiazinyl, quinazolinyl, naphthyridinyl, quinolinyl, isoquinolinyl, benzopyranyl, pyridopyridazinyl and pyridopyrimidinyl. Where indicated the heteroaryl groups can be optionally substituted by, for example, halogens, —NR$_d$R$_e$, —CONR$_d$R$_e$, —NR$_d$COR$_e$, carboxy, —C(=NR$_d$)NR$_e$R$_f$, azido, cyano, —N(R$_d$)C(=NR$_e$)NR$_f$R$_g$, hydroxyl, nitro, nitroso, —N(R$_h$)CONR$_i$R$_j$, C$_{1-6}$ alkyl, C$_{2-6}$ alkenyl, C$_{2-6}$ alkynyl, C$_{1-6}$ alkyloxy, C$_{2-6}$ alkenyloxy, C$_{2-6}$ alkynyloxy, S(O)$_{0-2}$R$_a$, C$_{6-10}$ aryl, C$_{6-10}$ aryloxy, C$_{7-10}$ arylalkyl, C$_{6-10}$ aryl-C$_{1-10}$ alkyloxy, C(O)R$_a$, C(O)OR$_a$, NR$_a$C(O)R$_b$, SO$_2$NR$_a$R$_b$, NR$_a$SO$_2$R$_b$, NR$_a$SO$_2$NR$_b$R$_c$, CR$_a$N=OR$_b$, and/or NR$_a$COOR$_b$, wherein R$_a$-R$_j$ are each independently H, C$_{1-4}$ alkyl, C$_{2-4}$ alkenyl or C$_{2-4}$ alkynyl.

The term "heteroaralkyl" represents an optionally substituted heteroaryl group attached to the adjacent atom by an alkyl, alkenyl or alkynyl group. Where indicated the heteroaralkyl groups can be optionally substituted by, for example, halogens, —NR$_d$R$_e$, —CONR$_d$R$_e$, —NR$_d$COR$_e$, carboxy, —C(=NR$_d$)NR$_e$R$_f$, azido, cyano, —N(R$_d$)C(=NR$_e$)NR$_f$R$_g$, hydroxyl, nitro, nitroso, —N(R$_h$)CONR$_i$R$_j$, C$_{1-6}$ alkyl, C$_{2-6}$ alkenyl, C$_{2-6}$ alkynyl, C$_{1-6}$ alkyloxy, C$_{2-6}$ alkenyloxy, C$_{2-6}$ alkynyloxy, S(O)$_{0-2}$R$_a$, C$_{6-10}$ aryl, C$_{6-10}$ aryloxy, C$_{7-10}$ arylalkyl, C$_{6-10}$ aryl-C$_{1-10}$ alkyloxy, C(O)R$_a$, C(O)OR$_a$, NR$_a$C(O)R$_b$, SO$_2$NR$_a$R$_b$, NR$_a$SO$_2$R$_b$, NR$_a$SO$_2$NR$_b$R$_c$, CR$_a$N=OR$_b$, and/or NR$_a$COOR$_b$, wherein R$_a$-R$_j$ are each independently H, C$_{1-4}$ alkyl, C$_{2-4}$ alkenyl or C$_{2-4}$ alkynyl. It is understood that in a 6-18 member heteroaralkyl moiety, the 6-18 member represents the atoms that are present in both the heterocycle moiety and the alkyl, alkenyl or alkynyl groups. For example, the following groups are encompassed by a 7 member heteroaralkyl (* represents the attachment point):

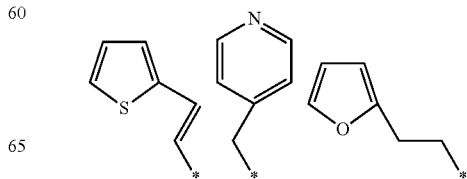

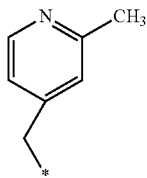

"Halogen atom" is specifically a fluorine atom, chlorine atom, bromine atom or iodine atom.

The term "amidino" represents —C(=NR$_d$)NR$_e$R$_f$ wherein R$_d$, R$_e$ and R$_f$ are each independently selected from H, C$_{1-10}$ alkyl, C$_{2-10}$ alkenyl, C$_{2-10}$ alkynyl, C$_{6-12}$ aryl and C$_{7-12}$ aralkyl, or R$_e$ and R$_f$ are taken together with the nitrogen to which they are attached to form an optionally substituted 4 to 10 member heterocycle or an optionally substituted 5-12 member heteroaryl.

The term "guanidino" represents —N(R$_d$)C(=NR$_e$)NR$_f$R$_g$ wherein R$_d$, R$_e$, R$_f$ and R$_g$ are each independently selected from H, C$_{1-10}$ alkyl, C$_{2-10}$ alkenyl, C$_{2-10}$ alkynyl, C$_{6-12}$ aryl and C$_{7-12}$ aralkyl, or R$_f$ and R$_g$ are taken together with the nitrogen to which they are attached to form an optionally substituted 4 to 10 member heterocycle or an optionally substituted 5-12 member heteroaryl.

The term "amido" represents —CONR$_d$R$_e$ and —NR$_d$COR$_e$, wherein R$_d$ and R$_e$ are each independently selected from H, C$_{1-10}$ alkyl, C$_{2-10}$ alkenyl, C$_{2-10}$ alkynyl, C$_{6-12}$ aryl and C$_{7-12}$ aralkyl, or R$_d$ and R$_e$ are taken together with the nitrogen to which they are attached (or the nitrogen atom and CO group in the case of —NR$_d$COR$_e$) to form an optionally substituted 4 to 10 member heterocycle or an optionally substituted 5-12 member heteroaryl.

The term "amino" represents a derivative of ammonia obtained by substituting one or more hydrogen atom and includes —NR$_d$R$_e$, wherein R$_d$ and R$_e$ are each independently selected from H, C$_{1-10}$ alkyl, C$_{2-10}$ alkenyl, C$_{2-10}$ alkynyl, C$_{6-12}$ aryl and C$_{7-12}$ aralkyl, or R$_d$ and R$_e$ are taken together with the nitrogen to which they are attached to form an optionally substituted 4 to 10 member heterocycle or an optionally substituted 5-12 member heteroaryl.

The term "sulfonamido" represents SO$_2$NR$_d$R$_e$, and —NR$_d$SO$_2$R$_e$, wherein R$_d$ and R$_e$ are each independently selected from H, C$_{1-10}$ alkyl, C$_{2-10}$ alkenyl, C$_{2-10}$ alkynyl, C$_{6-12}$ aryl and C$_{7-12}$ aralkyl, or R$_d$ and R$_e$ are taken together with the nitrogen to which they are attached to form an optionally substituted 4 to 10 member heterocycle or an optionally substituted 5-12 member heteroaryl.

When there is a sulfur atom present, the sulfur atom can be at different oxidation levels, i.e., S, SO, or SO$_2$. All such oxidation levels are within the scope of the present invention.

The term "independently" means that a substituent can be the same or a different definition for each item.

The terms "host" or "patient" means a human, male or female, for example, a child, an adolescent, or an adult.

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.1 to about 750 mg/kg of body weight per day, for example, in the range of 0.5 to 60 mg/kg/day, or, for example, in the range of 1 to 20 mg/kg/day.

The desired dose may conveniently be presented in a single dose or as divided dose administered at appropriate intervals, for example as two, three, four or more doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 μM, about 2 to 50 μM, about 3 to about 30 μM. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

When the compounds of the present invention or a pharmaceutically acceptable salts thereof is used in combination with a second therapeutic agent active against the same virus the dose of each compound may be either the same as or differ from that when the compound is used alone. Appropriate doses will be readily appreciated by those skilled in the art.

While it is possible that, for use in therapy, a compound of the invention may be administered as the raw chemical it is preferable to present the active ingredient as a pharmaceutical composition. The invention thus further provides a pharmaceutical composition comprising compounds of the present invention or a pharmaceutically acceptable derivative thereof together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Pharmaceutical compositions include those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical compositions suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

For topical administration to the epidermis, the compounds according to the invention may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Compositions suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical compositions suitable for rectal administration wherein the carrier is a solid are for example presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Compositions suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one more dispersing agents, solubilizing agents or suspending agents. Liquid sprays are conveniently delivered from pressurized packs.

For administration by inhalation the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

A compound of formula (I) may be prepared by reacting a compound of formula (II):

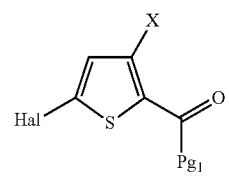

(II)

with a compound of the formula:

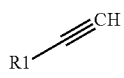

under conventional Sonogashira coupling conditions;
wherein;
X is as defined above, for example, $-NR_6-CO-R_5$,
$R_1$, $R_6$ and $R_5$ are as defined herein, $Pg_1$ is OH or a carboxyl protecting group, Hal is Cl, Br, or I (e.g., Br),
In a further embodiment, $Pg_1$ is methoxy or tert-butoxy.
In a further embodiment, $Pg_1$ is methoxy.

The Sonogashira coupling reaction is a well established method for producing acetylene containing compounds. Conditions for such coupling are well known in the art and can be found for example in the examples of the present application in Yamaguchi et al (Synlett 1999, No. 5, 549-550) or in Tykwinski et al, Angew. Chem. Int. Ed. 2003, 42, 1566-1568.

The present invention also includes intermediates that can be useful in the synthesis of the compounds of formula (I). Certain intermediates are represented by formula W

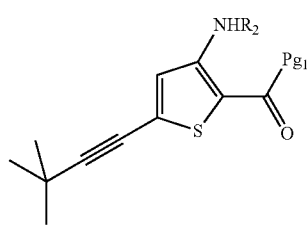

W wherein;
$R_2$, H or amino protecting group (e.g. Boc (tert-butoxycarbonyl), Cbz (benzyloxycarbonyl)) and
$Pg_1$ is OH or a carboxyl protecting group
In a further embodiment, $Pg_1$ is methoxy or tert-butoxy.
In a further embodiment, $Pg_1$ is methoxy.
In a further embodiment, R2 is H.
In a further embodiment, R2 is Boc.

Specific intermediates include but are not limited to compounds listed in Table A:

TABLE A

| Structure | Name | # |
|---|---|---|
| | 3-[(1,4-dioxa-spiro[4.5]dec-8-yl)-(trans-4-methyl-cyclo-hexanecarbonyl)-amino]-5-iodo-thiophene-2-carboxylic acid methyl ester | 3a |
| 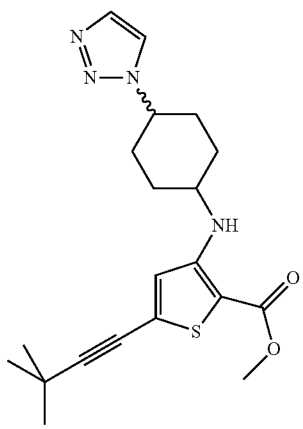 | 5-(3,3-dimethyl-but-1-ynyl)-3-(4-[1,2,3]triazol-1-yl-cyclohexylamino)-thiophene-2-carboxylic acid methyl ester | 4a |
| 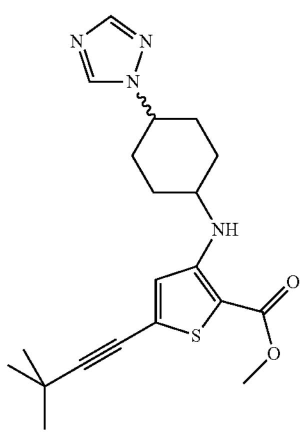 | 5-(3,3-dimethyl-but-1-ynyl)-3-(4-[1,2,4]triazol-1-yl-cyclohexylamino)-thiophene-2-carboxylic acid methyl ester | 5a |
| 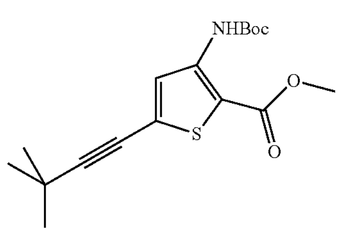 | 5-(3,3-dimethyl-but-1-ynyl)-3-(tert-butoxycarbonyl)amino-thiophene-2-carboxylic acid methyl ester | 9a |

TABLE A-continued

| Structure | Name | # |
|---|---|---|
| (structure) | 5-(3,3-dimethyl-but-1-ynyl)-3-amino-thiophene-2-carboxylic acid methyl ester | 9b |
| (structure) | 3-[(trans-4-hydroxy-cyclohexyl)-(trans-4-methyl-cyclohexanecarbonyl)-amino]-5-iodo-thiophene-2-carboxylic acid methyl ester | 10a |
| (structure) | 3-[(trans-4-Hydroxy-cyclohexyl)-(trans-4-methyl-cyclohexanecarbonyl)-amino]-5-trimethyl-silanylethynyl-thiophene-2-carboxylic acid methyl ester | 10b |

According to a further aspect of this invention there is providing a process for the preparation of compounds of formula I wherein X is

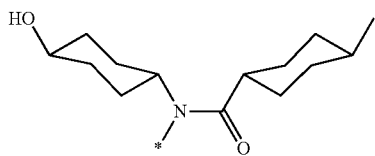

comprising using an intermediate of formula 3a or 10a or 10b.

According to a further aspect of this invention there is providing a process for the preparation of compounds of formula I wherein X is

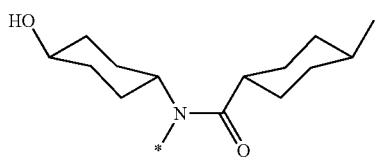

comprising using an intermediate of formula 3a or 10a or 10b.

According to a further aspect of this invention there is providing a process for the preparation of compounds of formula I wherein R1 is 3,3-dimethyl-but-1-ynyl comprising using an intermediate of formula 9a or 9b.

According to a further aspect of this invention there is providing a process for the preparation of compounds of formula I wherein R1 is 3,3-dimethyl-but-1-ynyl and R6 is 4-[1,2,3]triazol-1-yl-cyclohexyl comprising using an intermediate of formula 4a.

According to a further aspect of this invention there is providing a process for the preparation of compounds of formula I wherein R1 is 3,3-dimethyl-but-1-ynyl and R6 is 4-[1,2,4]triazol-1-yl-cyclohexyl comprising using an intermediate of formula 5a.

The following general schemes and examples are provided to illustrate various embodiments of the present invention and shall not be considered as limiting in scope. It will be appreciated by those of skill in the art that other compounds of the present invention can be obtained by substituting the generically or specifically described reactants and/or operating conditions used in the following examples. Synthesis methods to obtain thiophene compounds are also described in patent applications U.S. Pat. No. 6,881,741, U.S. Ser. No. 10/730,272 filed Dec. 9, 2003, U.S. Ser. No. 11/042,442 filed Jan. 26, 2005, U.S. Ser. No. 11/433,749 filed May 15, 2006, WO02/100851, US 2004-0116509, WO2004/052885, US 2005-0009804, WO2004/052879 and US 2004-0192707. Thiophene alkinyl compounds are also disclosed in WO 2006/072347 and WO 2006/072348.

In the foregoing and in the following examples, all temperatures are set forth uncorrected in degrees Celsius; and, unless otherwise indicated, all parts and percentages are by weight.

The following abbreviations may be used as follows:
Boc tert-butoxycarbonyl
DCC 1,3-dicyclohexylcarbodiimide
DCE 1,2-dichloroethane
DCM dichloromethane
DIPEA N,N-diisopropylethylamine DMF N,N-dimethylformamide
EToAc Ethyl acetate
Hal halogen
LAH lithium aluminium hydride
MeOH Methanol
TFA trifluoroacetic acid
THF tetrahydrofuran
LDA lithium diisopropylamide
TLC thin layer chromatography
RBO round bottom flask Purifications by HPLC were all performed using reverse phase C18 column packed with 5 μm particles. Column diameter was 19 mm and length was 100 mm. Eluent was an appropriate gradient of acetonitrile and water with a 3 mM HCl concentration.

EXAMPLE 1

Preparation of 5-(3,3-Dimethyl-but-1-ynyl)-3-[(trans-4-hydroxy-cyclohexyl)-(trans-4-methyl-cyclohexanecarbonyl)-amino]-thiophene-2-carboxylic acid

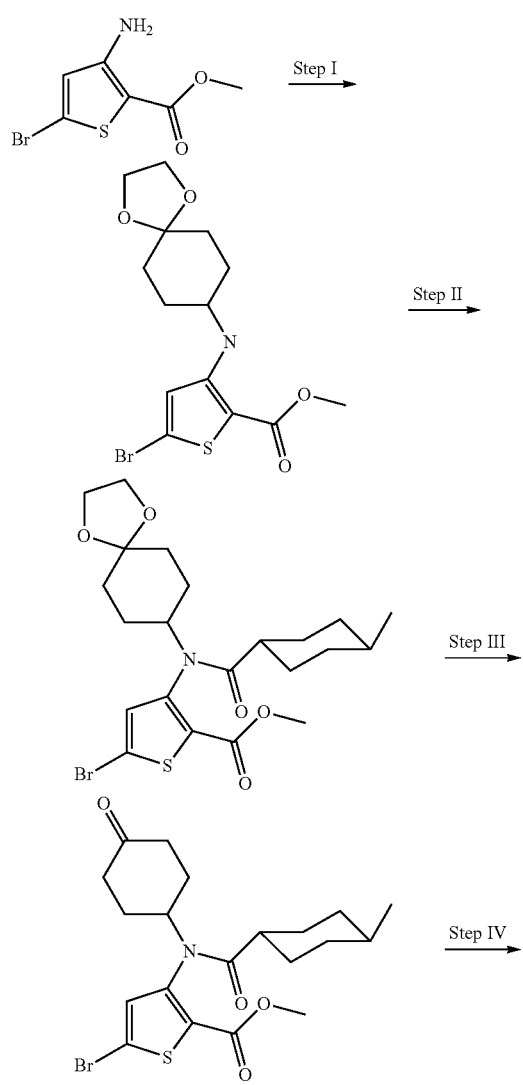

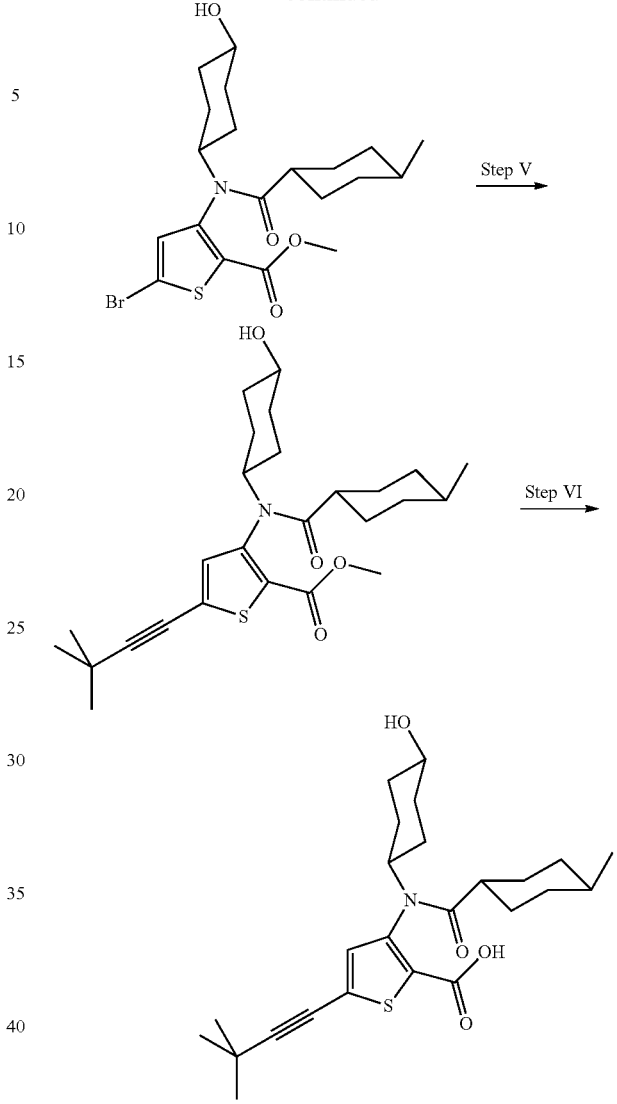

Step I

A suspension of 3-amino-5-bromo-thiophene-2-carboxylic acid methyl ester (17.0 g, 72.0 mmol) in dry THF (21 mL) is treated with 1,4-cyclohexanedione monoethylene ketal (11.3 mg, 72.0 mmol), followed by dibutyltin dichloride (1.098 g, 3.6 mmol). After 5 min, phenyl silane (9.74 mL, 79.2 mmol) is added and the reaction mixture is stirred overnight at room temperature. After concentration, the residue is dissolved in EtOAc washed with NaHCO₃ then brine. The organic layer is separated, dried on Na₂SO₄, filtered and concentrated. The crude material is diluted in hexane (500 mL). After filtration, the mother liquor is evaporated to dryness to give 5-bromo-3-(1,4-dioxa-spiro[4.5]dec-8-ylamino)-thiophene-2-carboxylic acid methyl ester (24.79 g, 92% yield).

Ref: WO2004/052885

Step II

Preparation of trans-4-methylcyclohexyl carboxylic acid chloride

Oxalyl chloride (2M in DCM, 117 mL) is added drop wise to a suspension of trans-4-methylcyclohexyl carboxylic acid (16.6 g, 117 mmol) in DCM (33 mL) and DMF (0.1 mL), and the reaction mixture is stirred 3 h at room temperature. DCM is removed under reduced pressure and the residue is co-evaporated with DCM. The residue is dissolved in toluene to make a 1M solution.

Preparation of the Target Compound:

The 1M solution of trans-4-methylcyclohexyl carboxylic acid chloride is added to a solution of 5-bromo-3-(1,4-dioxa-spiro[4.5]dec-8-ylamino)-thiophene-2-carboxylic acid methyl ester (24.79 g, 65 mmol) in toluene (25 mL) followed by pyridine (5.78 mL, 71.5 mmol). The resulting mixture is then stirred for 16 h at reflux. The reaction mixture is diluted with toluene (60 mL) and cooled down to 5° C. After the addition of pyridine (12 mL) and MeOH (5.6 mL), the mixture is stirred 2 h at 5° C. The white suspension is filtered off and the toluene is added to the mother liquor. The organic phase is washed with 10% citric acid, aq. Sat NaHCO$_3$, dried (Na$_2$SO$_4$) and concentrated. The residue is triturated in boiling hexane (1500 mL). The reaction mixture is allowed to cool down to room temperature. The reaction flask is immersed into ice bath, and stirred for 30 min; white solid is filtered off, and washed with cold hexane (225 mL). The solid is purified by silica gel column chromatography using 20% EtOAc:hexane as eluent to furnish the final compound 5-bromo-3-[(1,4-dioxa-spiro[4.5]dec-8-yl)-(trans-4-methyl-cyclohexanecarbonyl)-amino]-thiophene-2-carboxylic acid methyl ester (10.5 g, 32%).

Step III

5-Bromo-3-[(1,4-dioxa-spiro[4.5]dec-8-yl)-(trans-4-methylcyclohexane-carbonyl)-amino]-thiophene-2-carboxylic acid methyl ester (8.6 g, 17 mmol) is dissolved in tetrahydrofuran (100 mL) and treated with 3N HCl solution (50 mL). The reaction is stirred at 40° C. for 3 h. The reaction mixture is evaporated under reduced pressure. The residue is dissolved in EtOAc and washed with aq. sat. NaHCO$_3$ solution. The organic layer is separated, dried on Na$_2$SO$_4$, filtered and concentrated to give 5-bromo-3-[(trans-4-methyl-cyclohexanecarbonyl)-(4-oxo-cyclohexyl)-amino]-hiophene-2-carboxylic acid methyl ester as a solid (7.4 g, 95%).

Step IV

To a cold (0° C.) solution of 5-bromo-3-[(trans-4-methyl-cyclohexanecarbonyl)-(4-oxo-cyclohexyl)-amino]-thiophene-2-carboxylic acid methyl ester (5.9 g, 12.9 mmol) in 50 mL of MeOH under a N$_2$ atmosphere, NaBH$_4$ (250 mg, 6.4 mmol) is added portion wise (approx. 30 min). After the addition is completed and checked for reaction completion by TLC (hexane:EtOAc 1:1), 10 mL of HCl 2% is added and stirred for 15 min. The reaction mixture is concentrated under vacuum to dryness. The reaction mixture is recuperated with water (25 mL) and extracted with EtOAC. The organic phases are combined and dried over MgSO$_4$ and concentrated to dryness. The residue is purified by silica gel column chromatography using EtOAc:hexane (1:1) as eluent to obtain 5-bromo-3-[(trans-4-hydroxy-cyclohexyl)-(trans-4-methyl-cyclohexane-carbonyl)-amino]-thiophene-2-carboxylic acid methyl ester (4.5 g, 77% yield) as a solid.

Step V

To a solution of compounds 5-bromo-3-[(trans-4-hydroxy-cyclohexyl)-(trans-4-methyl-cyclohexanecarbonyl)-amino]-thiophene-2-carboxylic acid methyl ester (500 mg, 1.09 mmol) and 3,3-Dimethyl-but-1-yne (385 mg, 4.69 mmol) in DMF (0.5 mL), triethylamine (1.06 mL) and tris(dibenzylideneacetone)dipalladium (0) (70 mg, 0.08 mmol) are added and the reaction mixture is stirred under reflux conditions for 16 h under a N$_2$ atmosphere. DMF and triethylamine are removed under reduced pressure and the residue is partitioned between water and ethyl acetate. The organic layer is separated, dried (Na$_2$SO$_4$), concentrated and the residue is purified by column chromatography using ethyl acetate and hexane (1:2) as eluent to obtain 5-(3,3-dimethyl-but-1-ynyl)-3-[(trans-4-hydroxy-cyclohexyl)-(trans-4-methyl-cyclohexanecarbonyl)-amino]-thiophene-2-carboxylic acid methyl ester as a solid, 330 mg (66%).

Step VI 5-(3,3-Dimethyl-but-1-ynyl)-3-[(trans-4-hydroxy-cyclohexyl)-(trans-4-methyl-cyclohexanecarbonyl)-amino]-thiophene-2-carboxylic acid methyl ester (0.10 g, 0.22 mmol) is dissolved in a 3:2:1 mixture of THF:methanol:H$_2$O (5.0 mL) and treated with a 1N solution of LiOH.H$_2$O (0.65 mL, 0.65 mmol). After 2 h of stifling at 60° C., the reaction mixture is concentrated under reduced pressure on a rotary evaporator. The mixture is partitioned between ethyl acetate and water. The water layer is acidified using 0.1 N HCl. The EtOAc layer is separated and dried over Na$_2$SO$_4$. Filtration and removal of the solvent under reduced pressure on a rotary evaporator followed by purification by column chromatography using methanol and dichloromethane (1:9) as eluent to obtain 5-(3,3-dimethyl-but-1-ynyl)-3-[(trans-4-hydroxy-cyclohexyl)-(trans-4-methyl-cyclohexanecarbonyl)-amino]-thiophene-2-carboxylic acid as a solid, 30 mg (30%). ESI$^-$ (M−H): 444.3.

EXAMPLE 2

Preparation of 5-(3,3-Dimethyl-but-1-ynyl)-3-[(trans-4-methoxy-cyclohexyl)-(trans-4-methyl-cyclohexanecarbonyl)-amino]-thiophene-2-carboxylic acid

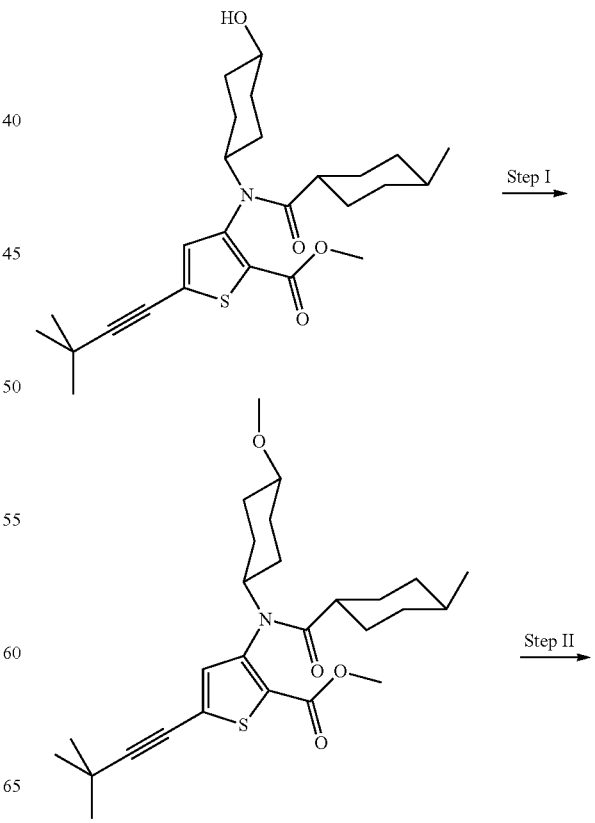

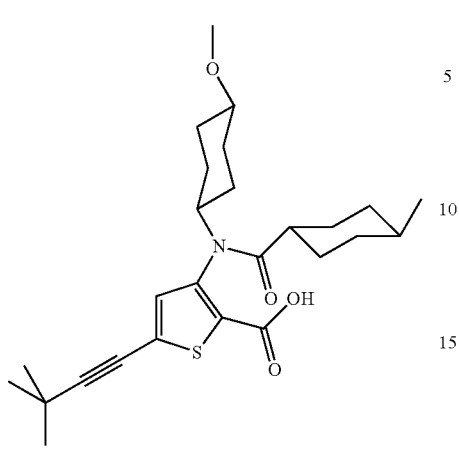

Step I

To a solution of 5-(3,3-dimethyl-but-1-ynyl)-3-[(trans-4-hydroxy-cyclohexyl)-(trans-4-methyl-cyclohexanecarbonyl)-amino]-thiophene-2-carboxylic acid methyl ester (0.200 g, 0.435 mmol) in dry DMF (2.0 mL) is added iodomethane (0.136 mL, 2.18 mmol), the mixture is cooled to 0° C., and NaH (60% suspension in oil, 35 mg, 0.87 mmol) is added in portions over 5 min. The mixture is stirred at 0° C. for 1 h 40 min, and it is quenched by addition of water and acidified with 2N HCl. The mixture is diluted with ethyl acetate and washed with brine. The organic layer is separated, dried over Na$_2$SO$_4$, concentrated under reduced pressure. The residue is purified by column chromatography on silica gel eluting with 0→50% ethyl acetate in hexane to give 5-(3,3-dimethyl-but-1-ynyl)-3-[(trans-4-methoxy-cyclohexyl)-(trans-4-methyl-cyclohexanecarbonyl)-amino]-thiophene-2-carboxylic acid methyl ester (65 mg, 32%).

Step II 5-(3,3-Dimethyl-but-1-ynyl)-3-[(trans-4-methoxy-cyclohexyl)-(trans-4-methyl-cyclohexanecarbonyl)-amino]-thiophene-2-carboxylic acid methyl ester from step I is hydrolysed as previously described (Scheme 1, step VI) to give 5-(3,3-dimethyl-but-1-ynyl)-3-[(trans-4-methoxy-cyclohexyl)-(trans-4-methyl-cyclohexanecarbonyl)-amino]-thiophene-2-carboxylic acid as a solid (65 mg, 32%). ESI⁻ (M−H): 458.3.

EXAMPLE 3

5-(3,3-Dimethyl-but-1-ynyl)-3-[(trans-4-hydroxy-cyclohexyl)-(trans-4-methyl-cyclohexanecarbonyl)-amino]-thiophene-2-carboxylic acid

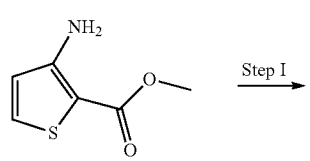 Step I→

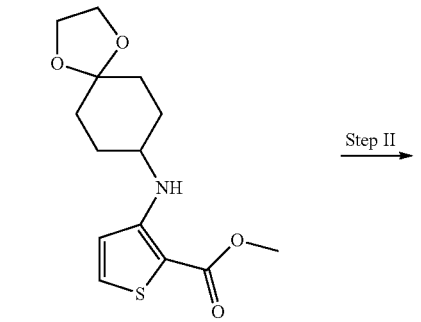 Step II→

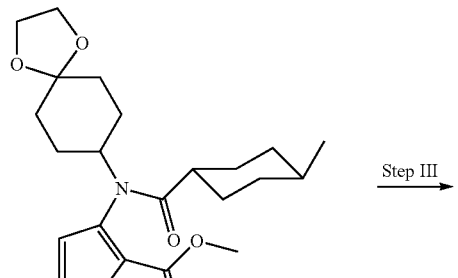 Step III→

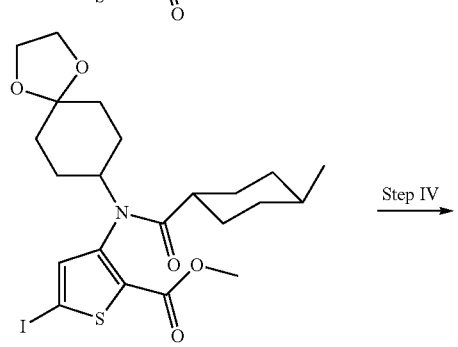 Step IV→

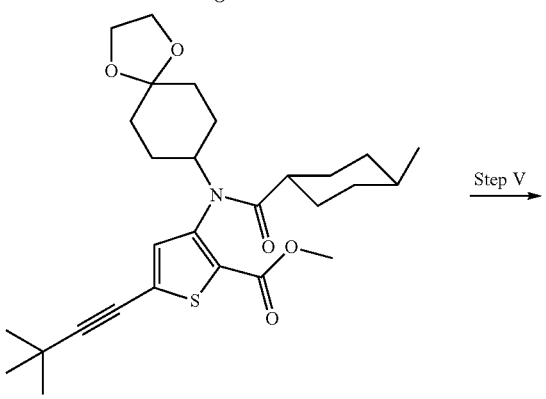 Step V→

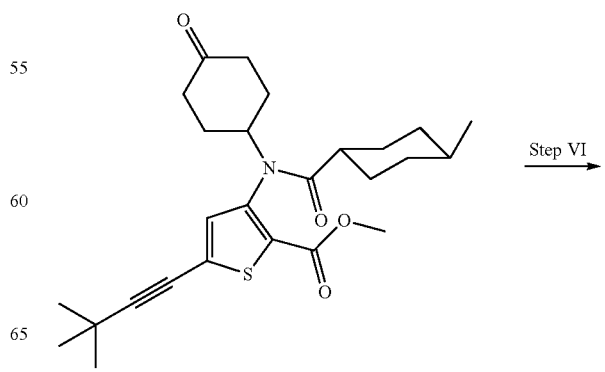 Step VI→

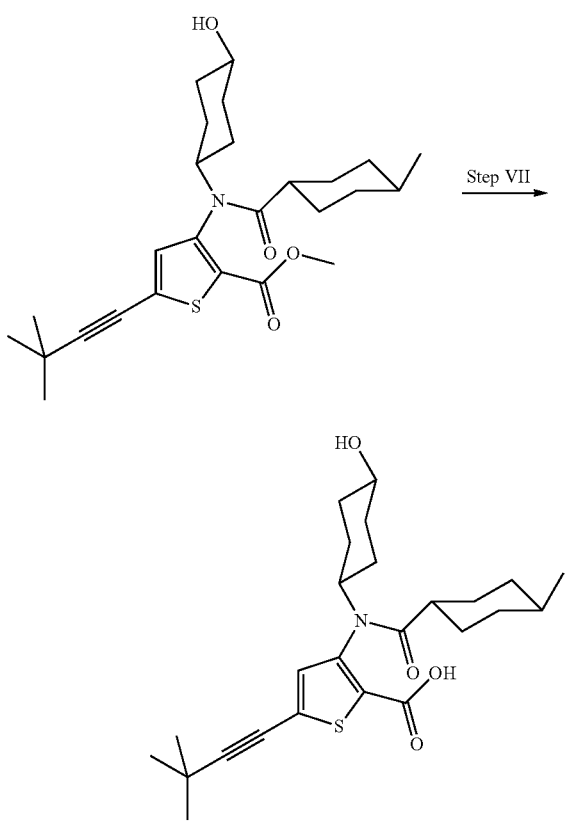

Step I

A suspension of 3-amino-thiophene-2-carboxylic acid methyl ester (5.0 g, 31.85 mmol) in dry THF (9 mL) is treated with 1,4-cyclohexanedione monoethylene ketal (5.0 g, 32.05 mmol), followed by dibutyltin dichloride (482 mg, 1.59 mmol). After 5 min, phenyl silane (4.3 mL, 34.96 mmol) is added and the reaction mixture is stirred overnight at room temperature. After concentration, the residue is dissolved in EtOAc and washed with NaHCO$_3$ followed by brine. The organic layer is separated, dried (Na$_2$SO$_4$), filtered and concentrated. The residue is purified by column chromatography using 30% ethyl acetate in hexane as eluent to give 3-(1,4-dioxa-spiro[4.5]dec-8-ylamino)-thiophene-2-carboxylic acid methyl ester (4.5 g, 47% yield).

Alternative Procedure:

3-Amino-thiophene-2-carboxylic acid methyl ester (1 eq.) is dissolved in dichloromethane followed by 1,4-cyclohexanedione monoethylene acetal (2 eq.) to obtain a slightly yellow solution. This solution is added to the suspension of NaBH(OAc)$_3$ (2.2 eq.) in dichloromethane. Acetic acid (2.4 eq.) is added dropwise over a period of 15 min. The resulting suspension is stirred at 20–25° C. under N$_2$ for 24 h. The reaction is quenched by adding water and stirred for 1 h. Dichloromethane layer is separated, treated with water again and stirred for another 1 h. The dichloromethane layer is separated and added to a saturated NaHCO$_3$ solution, stirred at 20–25° C. for 20 min. Some of the white residual solids are filtered and then the organic layer is separated, dried (Na$_2$SO$_4$) and evaporated. Methanol is added to the residue and evaporated to dryness. The residue is taken in of methanol and stirred for 2 h at 0° C. The suspension is vacuum-filtered and the resulting filtered cake is washed with cold methanol. The white solid is dried under vacuum at 35→40° C. for approximately 20 h to afford the title compound.

Step II

Preparation of trans-4-methylcyclohexyl carboxylic acid chloride

Oxalyl chloride (2M in dichloromethane, 17 mL) is added dropwise to a suspension of trans-4-methylcyclohexyl carboxylic acid (2.3 g, 16.2 mmol) in dichloromethane (5 mL) and DMF (0.1 mL). The reaction mixture is stirred for 3 h at room temperature. The volatiles are removed under reduced pressure to obtain the crude acid chloride which is used directly for the next reaction.

B-trans-4-Methylcyclohexyl carboxylic acid chloride is added to a solution of 3-(1,4-dioxa-spiro[4.5]dec-8-ylamino)-thiophene-2-carboxylic acid methyl ester (2.4 g, 8.08 mmol) in toluene (18 mL) followed by pyridine (0.7 mL). The resulting mixture is then stirred for 16 h at reflux. The reaction mixture is diluted with toluene (7 mL) and cooled to 5° C. After the addition of pyridine (1.5 mL) and MeOH (0.8 mL), the mixture is stirred 2 h at 5° C. The white solid is filtered and washed with toluene. The filtrate is washed with 10% citric acid, aq. NaHCO$_3$, dried (Na$_2$SO$_4$) and concentrated. The solid is purified by silica gel column chromatography using 20% EtOAc:hexane as eluent to obtain 3-[(1,4-dioxa-spiro[4.5]dec-8-yl)-(trans-4-methyl-cyclohexanecarbonyl)-amino]-thiophene-2-carboxylic acid methyl ester (2.3 g, 68%).

Alternative Procedure:

To a solution of trans-4-methylcyclohexyl carboxylic acid (1.8 eq.) in toluene under nitrogen is added anhydrous DMF. The reaction mixture is stirred and thionyl chloride (2.16 eq.) is added over 3-5 min. The mixture is then stirred for 3 h at rt. When the reaction is completed, toluene is added to the reaction mixture. The solution is then evaporated under reduced nitrogen pressure to half of its volume. The solution is dissolved in toluene to obtain a 1N acid chloride solution.

3-(1,4-Dioxa-spiro[4.5]dec-8-ylamino)-thiophene-2-carboxylic acid methyl ester (1 eq.) and pyridine (2 eq.) are added to the acid chloride (1N) solution. The reaction mixture is stirred at reflux for 15 h. Once the reaction is completed, the reaction mixture is cooled to room temperature, and then methanol and toluene are added to it. The reaction mixture is stirred for 1 h at rt and a saturated aqueous solution of NaHCO$_3$ is added. The organic layer is separated, dried (Na$_2$SO$_4$) and evaporated to about 4 volumes of solvent. To the solution are added 4 volumes of heptane while stirring. The reaction flask is immersed into an ice bath and stirred for 120 min; a beige solid is filtered off and washed with cold heptane, then dried over night in the vacuum oven to obtain the title compound.

Step III n-BuLi (2 eq.) is added dropwise for 10 min to a cold (−40° C.) solution of diisopropylamine (1 eq.) in dry THF. The reaction mixture is stirred at the same temperature for 30 min. Then a solution of 3-[(1,4-dioxa-spiro[4.5]dec-8-yl)-(trans-4-methyl-cyclohexane-carbonyl)-amino]-thiophene-2-carboxylic acid methyl ester (1 eq.) in THF is added dropwise (35 min) keeping the internal temperature around −40° C. The reaction mixture is stirred for 30 min and a solution of iodine (2 eq.) in THF is added dropwise, stirred for 30 min at the same temperature before being added a sat. solution of NH$_4$Cl. The reaction mixture is diluted with ethyl acetate and water. The organic layer is separated and washed with 5% sodium thiosulfate solution. The organic layer is separated, dried (Na₂SO₄) and evaporated to a suspension and then added heptane. The suspension is stirred at 0° C. for 30 min, filtered and washed with heptane to obtain 3-[(1,4-dioxa-spiro[4.5]dec-8-yl)-(trans-4-methyl-cyclo-hexanecarbonyl)-amino]-5-iodo-thiophene-2-carboxylic acid methyl ester.

MS found (electrospray): (M+H): 548.21

Step IV

To a 25 mL RBF under nitrogen, 3-[(1,4-dioxa-spiro[4.5]dec-8-yl)-(trans-4-methyl-cyclohexanecarbonyl)-amino]-5-iodo-thiophene-2-carboxylic acid methyl ester (1 eq.), copper iodide (0.025 eq.) and tris(dibenzylideneacetone)dipalladium (0) (0.01 eq.) are taken. DMF, triethylamine (2.5 eq.) and 3,3-dimethyl-but-1-yne (2 eq.) are added and the reaction mixture is stirred at 40° C. for 2 h under a N₂ atmosphere. The reaction mixture is filtered on celite and washed with ethyl acetate. The solution is diluted with water and extracted 2 times with ethyl acetate. The organic phases are combined and washed 3 times with water. The organic layer is separated, dried (Na₂SO₄), evaporated to about 2 mL and then 8 mL of heptane is added. It is evaporated to 2-4 mL and cooled in an ice bath. The formed white solid is filtered, washed with heptane and dried in oven to obtain 5-(3,3-dimethyl-but-1-ynyl)-3-[(1,4-dioxa-spiro[4.5]dec-8-yl)-(trans-4-methyl-cyclohexanecarbonyl)-amino]-thiophene-2-carboxylic acid methyl ester.

Step V 5-(3,3-Dimethyl-but-1-ynyl)-3-[(1,4-dioxa-spiro[4.5]dec-8-yl)-(trans-4-methyl-cyclohexanecarbonyl)-amino]-thiophene-2-carboxylic acid methyl ester (1 eq.) is dissolved in tetrahydrofuran and treated with 3.6 N HCl solution. The reaction is stirred at 40° C. for 5 h. Water is then added and the reaction mixture is cooled to room temperature. The reaction mixture is extracted with ethyl acetate (2×50 mL). The combined extracts are washed with 25 mL of aqueous saturated NaHCO₃ and 2×50 mL of water. The organic layer is concentrated to a thick oil and 50 mL of heptane is added to the mixture to precipitate the desired compound which is filtered to give of 5-(3,3-dimethyl-but-1-ynyl)-3-[(trans-4-methyl-cyclohexanecarbonyl)-(4-oxo-cyclohexyl)-amino]-thiophene-2-carboxylic acid methyl ester.

Step VI 5-(3,3-Dimethyl-but-1-ynyl)-3-[(trans-4-methyl-cyclohexanecarbonyl)-(4-oxo-cyclohexyl)-amino]-thiophene-2-carboxylic acid methyl ester (1 eq.) is dissolved in THF. Water is added to the reaction mixture and cooled to −25° C. NaBH₄ (0.5 eq.) is added portion wise maintaining the temperature below −20° C. The mixture is stirred for 2 h at −25° C., 2N HCl is then added and the solution is warmed to room temperature. The phases are separated and the aqueous layer is washed with EtOAC. The organic phases are combined and washed with brine and dried over Na₂SO₄ and concentrated to dryness to give 5-(3,3-dimethyl-but-1-ynyl)-3-[(4-hydroxy-cyclohexyl)-(trans-4-methyl-cyclohexanecarbonyl)-amino]-thiophene-2-carboxylic acid methyl ester as a 93:7 mixture of isomers. The crude cis/trans mixture is recrystallized in methanol to obtain >99% the trans isomer.

Step VII

The same procedure as reported earlier (example 1, step VI) is followed to obtain 5-(3,3-dimethyl-but-1-ynyl)-3-[(trans-4-hydroxy-cyclohexyl)-(trans-4-methyl-cyclohexanecarbonyl)-amino]-thiophene-2-carboxylic acid.

MS found (electrospray): (M−H): 444.3

EXAMPLE 4

5-(3,3-Dimethyl-but-1-ynyl)-3-[(trans-4-methyl-cyclohexanecarbonyl)-(cis-4-[1,2,3]triazol-1-yl-cyclohexyl)-amino]-thiophene-2-carboxylic acid and 5-(3,3-Dimethyl-but-1-ynyl)-3-[(trans-4-methyl-cyclohexane-carbonyl)-(trans-4-[1,2,3]triazol-1-yl-cyclohexyl)-amino]-thiophene-2-carboxylic Acid

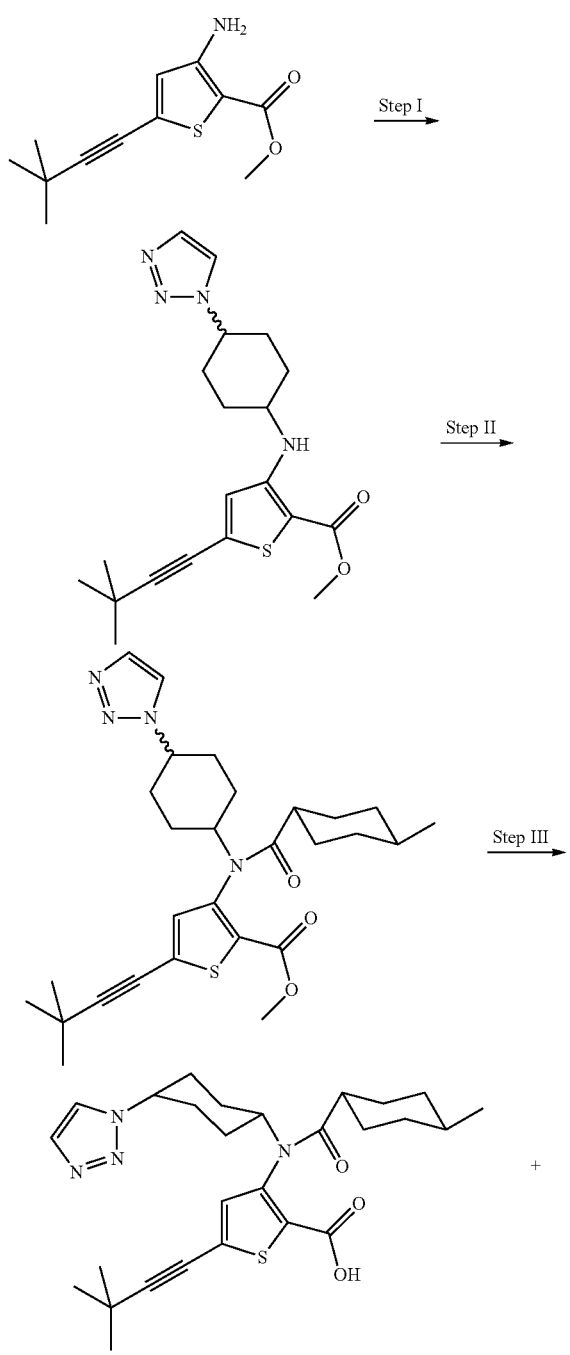

-continued

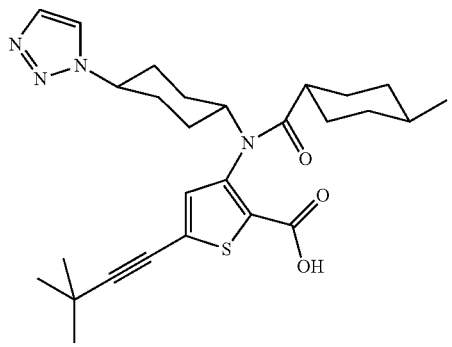

Step I

To a solution of 3-amino-5-(3,3-dimethyl-but-1-ynyl)-thiophene-2-carboxylic acid methyl ester (example 9)(0.387 g, 1.6 mmol) and 4-[1,2,3]triazol-1-yl-cyclohexanone (0.27 g, 1.6 mmol) in dry THF is added dibutyltin dichloride (0.024 g, 0.080 mmol) followed by phenylsilane (0.276 ml, 2.2 mmol). The mixture is stirred overnight at room temperature. Solvent is evaporated under reduced pressure, and the residue is diluted with ethyl acetate. The organic layer is washed with water and brine, dried with sodium sulfate, filtered and concentrated under reduced pressure. The residue is purified by column chromatography on silica gel using gradient 50-100% ethyl acetate in hexane to afford 5-(3,3-dimethyl-but-1-ynyl)-3-(4-[1,2,3]triazol-1-yl-cyclohexylamino)-thiophene-2-carboxylic acid methyl ester.

Step II

To a solution of 5-(3,3-dimethyl-but-1-ynyl)-3-(4-[1,2,3]triazol-1-yl-cyclohexylamino)-thiophene-2-carboxylic acid methyl ester (0.20 g, 0.50 mmol) in toluene (1 ml) is added a solution of trans-4-methylcyclohexyl carboxylic acid chloride 1 M (1.0 ml, 1.0 mmol) and pyridine (0.046 ml, 0.58 mmol). The mixture is stirred overnight at 105° C. and diluted with ethyl acetate. The organic layer is washed with NaHCO$_3$ sat (2×) and brine. The organic layer is dried with sodium sulfate, filtered and concentrated under reduce pressure. The residue is purified by silica gel column chromatography (20% ethyl acetate/hexane to 100% ethyl acetate followed by 10% MeOH/ethyl acetate) to give 5-(3,3-dimethyl-but-1-ynyl)-3-[(trans-4-methyl-cyclohexanecarbonyl)-(4-[1,2,3]triazol-1-yl-cyclohexyl)-amino]-thiophene-2-carboxylic acid methyl ester.

Step III 5-(3,3-Dimethyl-but-1-ynyl)-3-[(trans-4-methyl-cyclohexanecarbonyl)-(4-[1,2,3]triazol-1-yl-cyclohexyl)-amino]-thiophene-2-carboxylic acid methyl ester (0.13 g, 0.25 mmol) is hydrolyzed with lithium hydroxide as previously described (example 1, step V1) to give after HPLC purification the pure isomer 5-(3,3-dimethyl-but-1-ynyl)-3-[(trans-4-methyl-cyclohexanecarbonyl)-(cis-4-[1,2,3]triazol-1-yl-cyclohexyl)-amino]-thiophene-2-carboxylic acid and 5-(3,3-dimethyl-but-1-ynyl)-3-[(trans-4-methyl-cyclohexanecarbonyl)-(trans-4-[1,2,3]triazol-1-yl-cyclohexyl)-amino]-thiophene-2-carboxylic acid.

MS found (electrospray): (M+H): 497.4

EXAMPLE 5

5-(3,3-Dimethyl-but-1-ynyl)-3-[(trans-4-methyl-cyclohexanecarbonyl)-(cis-4-[1,2,4]triazol-1-yl-cyclohexyl)-amino]-thiophene-2-carboxylic acid and 5-(3,3-Dimethyl-but-1-ynyl)-3-[(trans-4-methyl-cyclohexane-carbonyl)-(trans-4-[1,2,4]triazol-1-yl-cyclohexyl)-amino]-thiophene-2-carboxylic acid

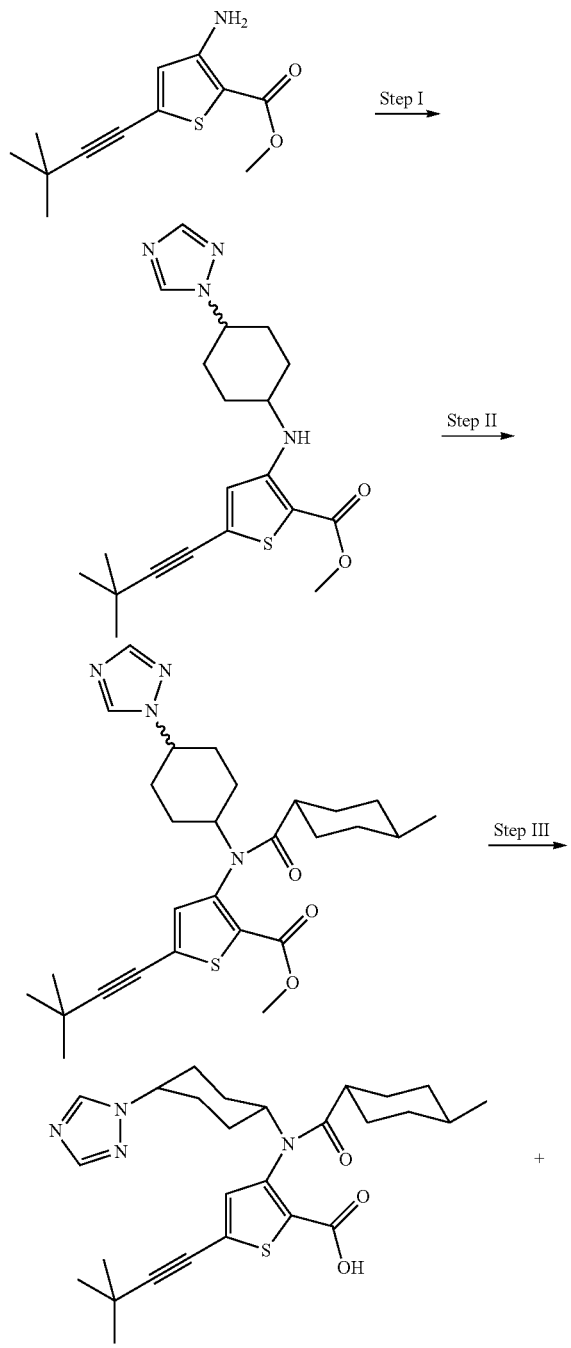

-continued

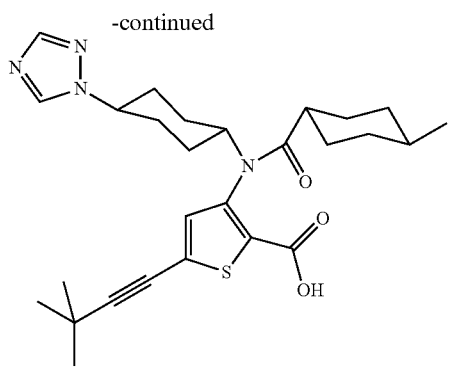

Step I

Reductive amination of 3-amino-5-(3,3-dimethyl-but-1-ynyl)-thiophene-2-carboxylic acid methyl ester (0.237 g, 1.0 mmol) and 4-[1,2,4]triazol-1-yl-cyclohexanone (0.170 g, 1.0 mmol) is performed under the same conditions previously described using dibutyltin dichloride and phenylsilane to give 5-(3,3-dimethyl-but-1-ynyl)-3-(4-[1,2,4]triazol-1-yl-cyclohexylamino)-thiophene-2-carboxylic acid methyl ester.

Step II 5-(3,3-Dimethyl-but-1-ynyl)-3-(4-[1,2,4]triazol-1-yl-cyclohexylamino)-thiophene-2-carboxylic acid methyl ester (0.27 g, 0.70 mmol) is acylated with trans-4-methylcyclohexyl carboxylic acid chloride as previously described to give 5-(3,3-dimethyl-but-1-ynyl)-3-[(trans-4-methyl-cyclohexanecarbonyl)-(4-[1,2,4]triazol-1-yl-cyclohexyl)-amino]-thiophene-2-carboxylic acid methyl ester.

Step III 5-(3,3-Dimethyl-but-1-ynyl)-3-[(trans-4-methyl-cyclohexanecarbonyl)-(4-[1,2,4]triazol-1-yl-cyclohexyl)-amino]-thiophene-2-carboxylic acid methyl ester (0.244 g, 0.48 mmol) is hydrolysed with lithium hydroxide as previously described (example 1, step VI) to give after HPLC purification the pure isomer 5-(3,3-Dimethyl-but-1-ynyl)-3-[(trans-4-methyl-cyclohexanecarbonyl)-(cis-4-[1,2,4]triazol-1-yl-cyclohexyl)-amino]-thiophene-2-carboxylic acid and (3,3-Dimethyl-but-1-ynyl)-3-[(trans-4-methyl-cyclohexanecarbonyl)-(trans-4-[1,2,4]triazol-1-yl-cyclohexyl)-amino]-thiophene-2-carboxylic acid.

MS found (electrospray): (M+H): 497.4

EXAMPLE 6

5-(3,3-Dimethyl-but-1-ynyl)-3-[(trans-4-methyl-cyclohexanecarbonyl)-(trans-4-[1,2,3]triazol-1-yl-cyclohexyl)-amino]-thiophene-2-carboxylic Acid

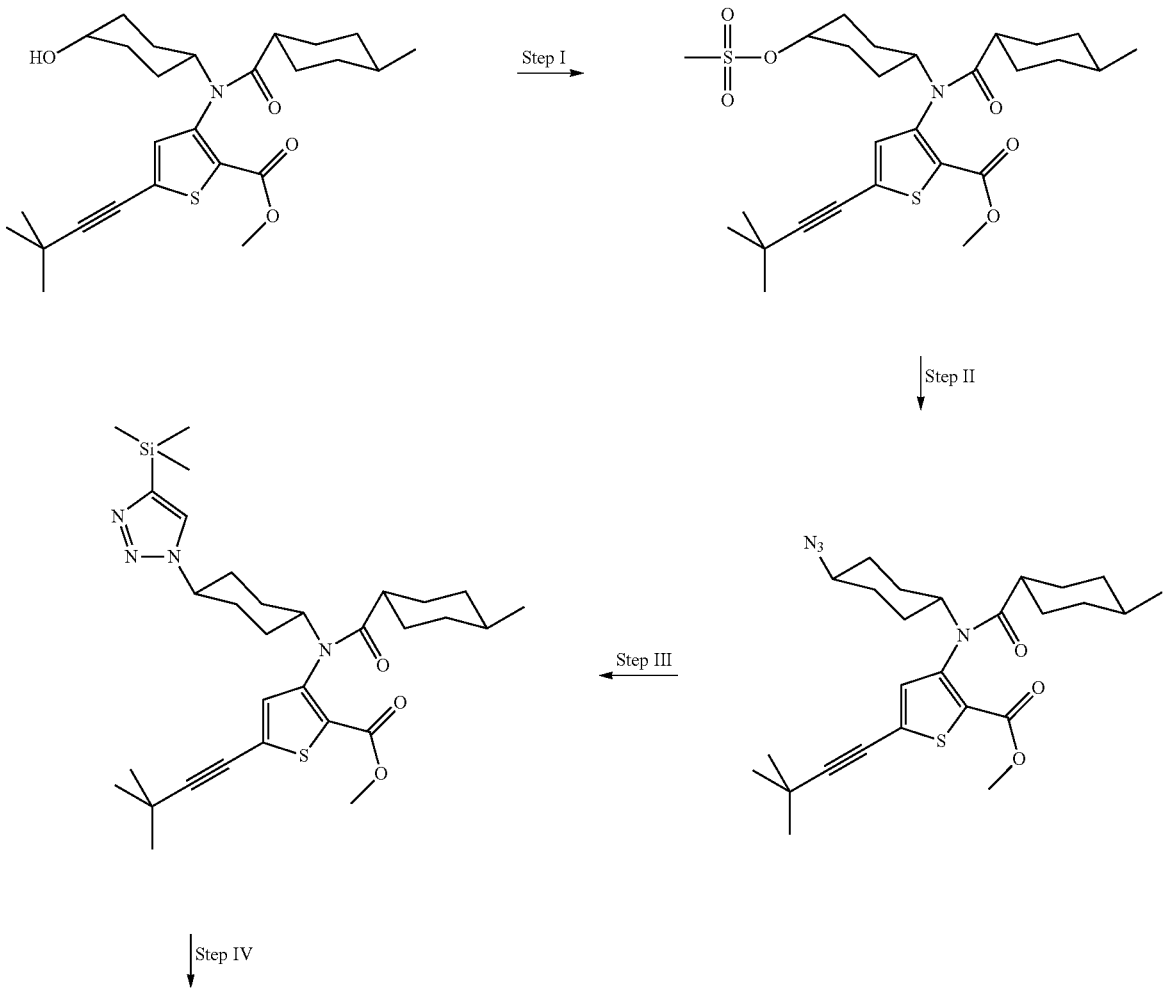

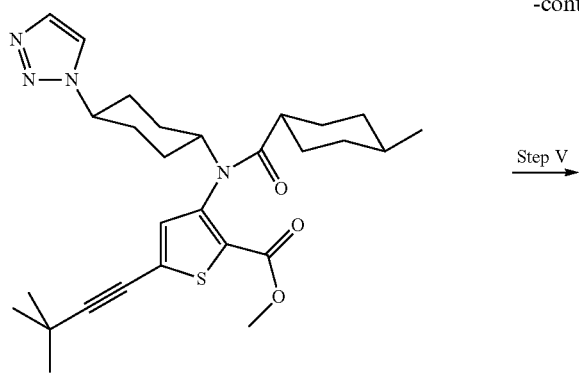

-continued

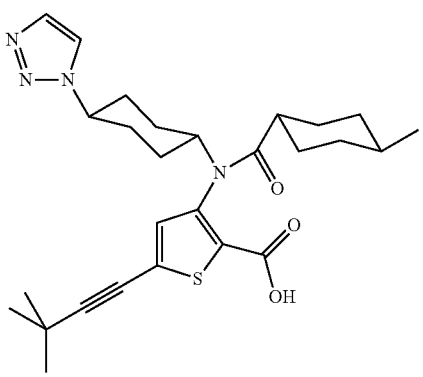

Step V

Step I

To a solution of 5-(3,3-dimethyl-but-1-ynyl)-3-[(cis-4-hydroxy-cyclohexyl)-(trans-4-methyl-cyclohexanecarbonyl)-amino]-thiophene-2-carboxylic acid methyl ester (0.92 g, 2.0 mmol) in 10 ml of $CH_2Cl_2$ is added at 0° C. methanesulfonyl chloride (0.31 mL, 4.0 mmol) followed by triethylamine (0.56 ml, 4.0 mmol). The reaction mixture is stirred at room temperature for 24 h and treated with water. The aqueous layer is extracted 2 times with $CH_2Cl_2$. The organic layer is dried with sodium sulfate, filtered and concentrated under reduced pressure to give 5-(3,3-dimethyl-but-1-ynyl)-3-[(cis-4-methanesulfonyloxy-cyclohexyl)-(trans-4-methyl-cyclohexanecarbonyl)-amino]-thiophene-2-carboxylic acid methyl ester.

Step II

To a solution of 5-(3,3-dimethyl-but-1-ynyl)-3-[(cis-4-methanesulfonyloxy-cyclohexyl)-(trans-4-methyl-cyclohexanecarbonyl)-amino]-thiophene-2-carboxylic acid methyl ester (1.16 g, 2.00 mmol) in 10 ml of DMF is added sodium azide (0.65 g, 10 mmol). The reaction mixture is stirred for 48 h at 50° C. The mixture is diluted with ethyl acetate, washed 3 times with water and 1 time with brine. The organic layer is dried with sodium sulfate, filtered and concentrated under reduce pressure to give 3-[(trans-4-azido-cyclohexyl)-(trans-4-methyl-cyclohexanecarbonyl)-amino]-5-(3,3-dimethyl-but-1-ynyl)-thiophene-2-carboxylic acid methyl ester.

Step III

A solution of 3-[(trans-4-azido-cyclohexyl)-(trans-4-methyl-cyclohexanecarbonyl)-amino]-5-(3,3-dimethyl-but-1-ynyl)-thiophene-2-carboxylic acid methyl ester (1.0 g, 2.0 mmol) in trimethylsilylacetylene (1.4 ml, 10 mmol) is treated in microwave at 120° C. for 2 h. The mixture is concentrated under reduced pressure and the residue is purified by silica gel column chromatography (5% ethyl acetate/hexane to 100% ethyl acetate) to afford 5-(3,3-dimethyl-but-1-ynyl)-3-{(trans-4-methyl-cyclohexanecarbonyl)-[trans-4-(4-trimethylsilanyl-[1,2,3]triazol-1-yl)-cyclohexyl]-amino}-thiophene-2-carboxylic acid methyl ester.

Step VI

To a solution of 5-(3,3-dimethyl-but-1-ynyl)-3-{(trans-4-methyl-cyclohexanecarbonyl)-[trans-4-(4-trimethylsilanyl-[1,2,3]triazol-1-yl)-cyclohexyl]-amino}-thiophene-2-carboxylic acid methyl ester (0.48 g, 0.82 mmol) in THF (2.0 ml) is added TBAF 1.0 M in THF (1.23 ml, 1.23 mmol). The reaction mixture is stirred for 24 h and treated with water and saturated ammonium chloride solution. The aqueous layer is extracted with ethyl acetate. The organic layer is washed with brine, dried with sodium sulfate, filtered and concentrated under reduced pressure. The residue is purified by silica gel column chromatography (50% ethyl acetate/hexane to 100% ethyl acetate) to give 5-(3,3-dimethyl-but-1-ynyl)-3-[(trans-4-methyl-cyclohexanecarbonyl)-(trans-4-[1,2,3]triazol-1-yl-cyclohexyl)-amino]-thiophene-2-carboxylic acid methyl ester.

Step V 5-(3,3-Dimethyl-but-1-ynyl)-3-[(trans-4-methyl-cyclohexanecarbonyl)-(trans-4-[1,2,3]triazol-1-yl-cyclohexyl)-amino]-thiophene-2-carboxylic acid methyl ester (0.27 g, 0.52 mmol) is hydrolysed with lithium hydroxide as previously described (example 1, step VI) to give after HPLC purification 5-(3,3-dimethyl-but-1-ynyl)-3-[(trans-4-methyl-cyclohexanecarbonyl)-(trans-4-[1,2,3]triazol-1-yl-cyclohexyl)-amino]-thiophene-2-carboxylic acid.

MS found (electrospray): (M+H): 497.4

Intermediate 2: 4-[1,2,3]triazol-1-yl-cyclohexanone

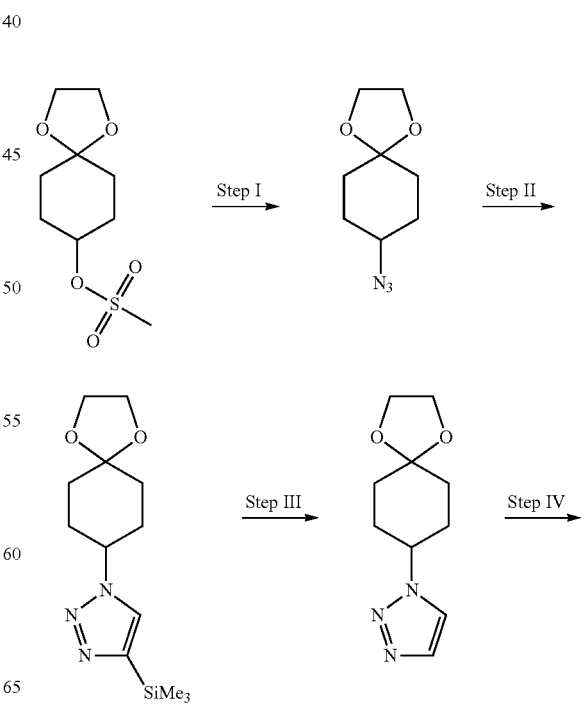

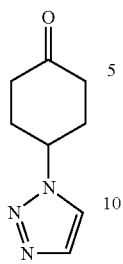

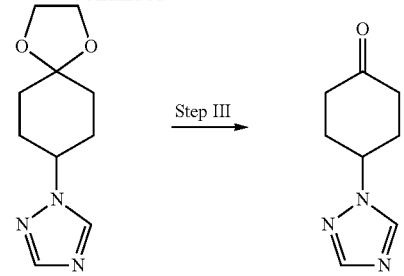

Step I

A mixture of methanesulfonic acid 1,4-dioxa-spiro[4.5]dec-8-yl ester (2.80 g, 11.9 mmol) and sodium azide (3.86 g, 59.3 mmol) in 50 mL of dry DMF is stirred for 20 h at 100° C. under nitrogen. The final mixture is cooled to room temperature diluted with brine and extracted with three portions of ether. The organic portions are combined, dried over $Na_2SO_4$ and concentrated to give 8-azido-1,4-dioxa-spiro[4.5]decane.

Step II

A mixture of 8-azido-1,4-dioxa-spiro[4.5]decane (1.00 g, 5.43 mmol) and 1-(trimethylsilyl)propyne (3.76 mL, 27.1 mmol) is submitted to microwave at 120° C. for 2 h. The mixture is concentrated under vacuum to remove the excess of 1-(trimethylsilyl)propyne and crude 1-(1,4-dioxa-spiro[4.5]dec-8-yl)-4-trimethylsilanyl-1H-[1,2,3]triazole is obtained.

Step III

A solution of 1-(1,4-dioxa-spiro[4.5]dec-8-yl)-4-trimethylsilanyl-1H-[1,2,3]-triazole (1.60 g, 5.68) in 41 mL of dry THF is treated by a 1M solution of tetrabutylammonium fluoride in THF (9.0 mL, 9.0 mmol). The resulting mixture is stirred for 48 h at room temperature under nitrogen. It is diluted with EtOAc, washed with saturated aqueous ammonium chloride, water and brine, dried over $Na_2SO_4$ and concentrated to give 1-(1,4-dioxa-spiro[4.5]dec-8-yl)-1H-[1,2,3]triazole.

Step IV 1-(1,4-Dioxa-spiro[4.5]dec-8-yl)-1H-[1,2,3]triazole (1.06 g, 5.06 mmol) is submitted to the same procedure as for intermediate 1 step III to afford 4-[1,2,3]triazol-1-yl-cyclohexanone as a white solid.

Intermediate 1: 4-[1,2,4]triazol-1-yl-cyclohexanone

Step I

Methanesulfonic acid 1,4-dioxa-spiro[4.5]dec-8-yl ester is prepared according to: Cheng, Chen Yu; Wu, Shou Chien; Hsin, Ling Wei; Tam, S. William. Coll. Med., Natl. Taiwan Univ., Taipei, Taiwan. *Journal of Medicinal Chemistry* (1992), 35(12), 2243-7.

Step II

A solution of methanesulfonic acid 1,4-dioxa-spiro[4.5]dec-8-yl ester (567 mg, 2.40 mmol) and 1,2,4-triazole (232 mg, 3.36 mmol) in dry DMF (5.00 mL) is treated with sodium hydride 60% (125 mg, 3.12 mmol) at room temperature under nitrogen. The resulting mixture is stirred at 65° C. for 72 h. It is poured in ice water (75 mL), extracted 3 portions of 75 mL of EtOAc. The organic portions are combined, dried over anhydrous $Na_2SO_4$ and concentrated. The solid is purified by silica gel column chromatography using a gradient from 100% EtOAc to 5% MeOH:EtOAc as eluent to furnish the final compound I-(1,4-dioxa-spiro[4.5]dec-8-yl)-1H-[1,2,4]triazole as a white solid.

Step III 1-(1,4-Dioxa-spiro[4.5]dec-8-yl)-1H-[1,2,4]-triazole (379 mg, 1.81 mmol) is dissolved in a 1:1 mixture of THF and 3N HCl aqueous solution (9 mL). The resulting mixture is stirred at 40° C. for 5 h. Most of the THF is removed under vacuum then the remaining mixture is neutralized using a 3N NaOH aqueous solution until a basic pH is reached. It is extracted with 3 portions of 10 mL of dichloromethane. The organic portions are combined, dried over anhydrous $Na_2SO_4$ and concentrated to afford 4-[1,2,4]-triazol-1-yl-cyclohexanone as a white waxy solid.

EXAMPLE 7

Preparation of 5-(3,3-dimethyl-but-1-ynyl)-3-[(trans-4-fluoro-cyclohexyl)-(trans-4-methyl-cyclohexanecarbonyl)-amino]-thiophene-2-carboxylic Acid

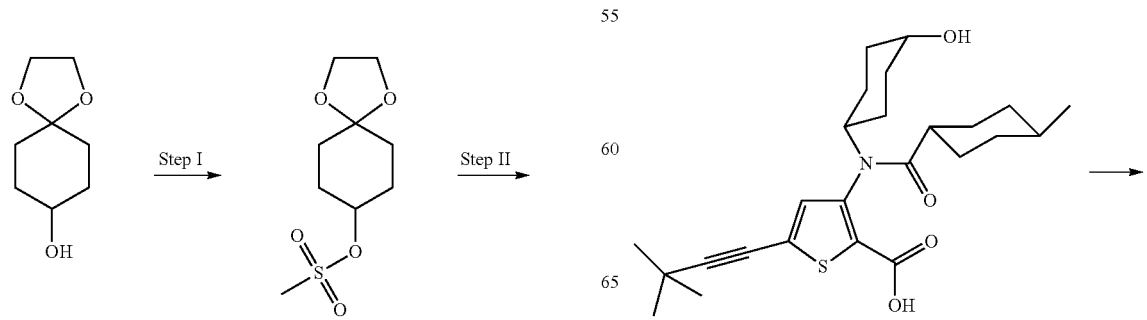

-continued

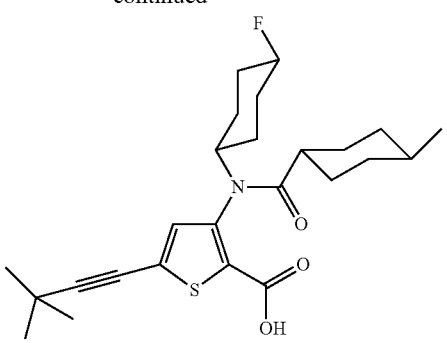

To a suspension of 5-(3,3-dimethyl-but-1-ynyl)-3-[(cis-4-hydroxy-cyclohexyl)-(trans-4-methyl-cyclohexanecarbonyl)-amino]-thiophene-2-carboxylic acid (102 mg, 0.23 mmol) in dry $CH_2Cl_2$ (2 mL) is added DAST (Diethylamino-sulphurtrifluoride) (90 µL, 0.69 mmol), and the mixture is stirred for 4 h at room temperature. Then it is diluted with $CH_2Cl_2$, water is added to the mixture, and it is vigorously stirred for 20 min. Organic fraction is separated, dried over $Na_2SO_4$, concentrated, and the residue is purified by preparative HPLC to give 5-(3,3-dimethyl-but-1-ynyl)-3-[(trans-4-fluoro-cyclohexyl)-(trans-4-methyl-cyclohexanecarbonyl)-amino]-thiophene-2-carboxylic acid.

MS found (electrospray): [M+H]: 448.30

EXAMPLE 8

Preparation of 5-(3,3-dimethyl-but-1-ynyl)-3-[(trans-4-methyl-cyclohexanecarbonyl)-(1-methyl-piperidin-4-yl)-amino]-thiophene-2-carboxylic acid hydrochloride

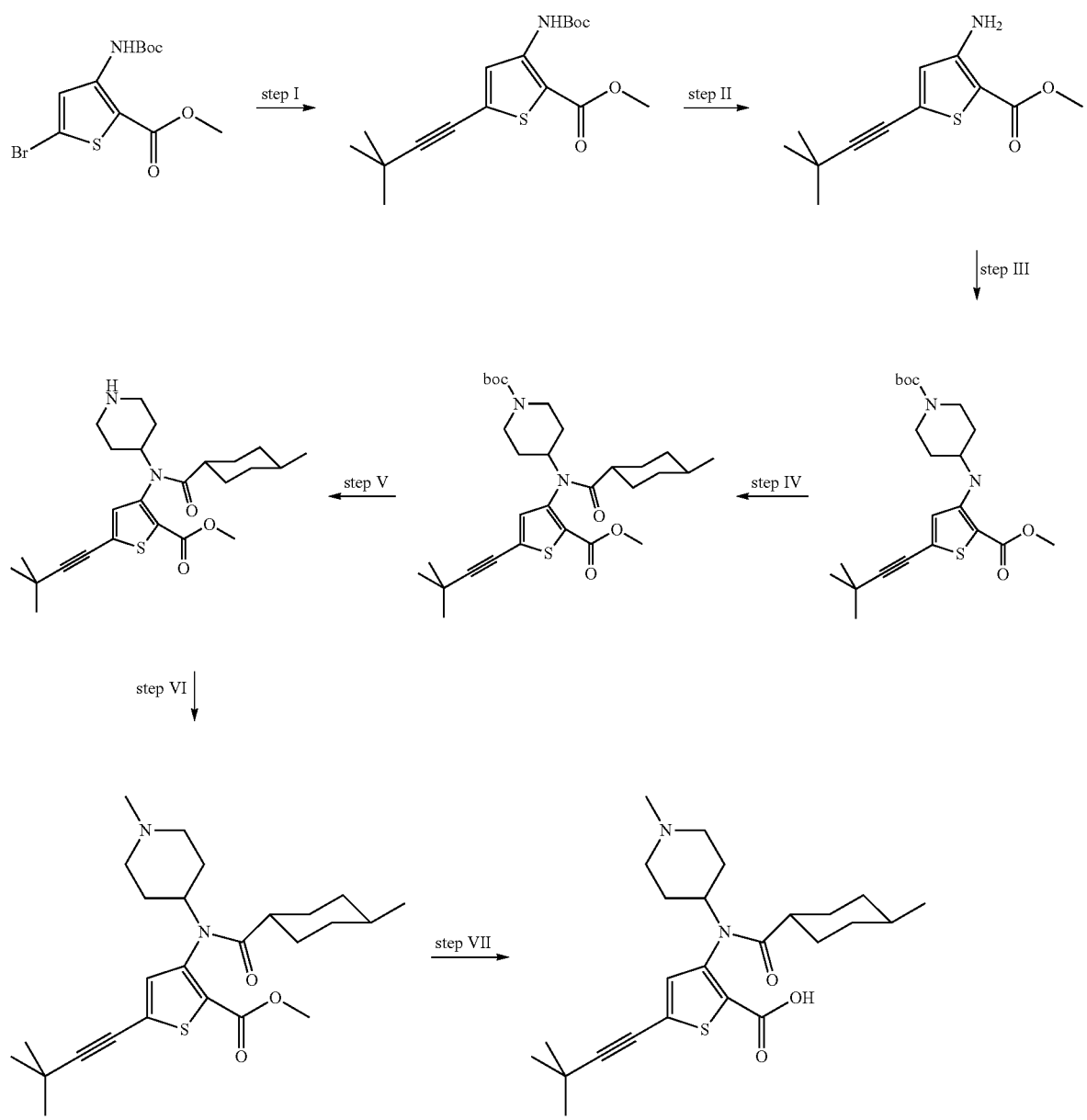

Step I

To a solution of 3-(tert-butoxycarbonyl)amino-5-bromo-thiophene-2-carboxylic acid methyl ester (4.566 g, 13.58 mmol) in dry DMF (40 mL) are added copper (I) iodide (52 mg, 0.27 mmol), $Pd_2dba_3$ (622 mg, 0.68 mmol) and triethylamine (9.46 mL, 67.9 mmol), and the mixture is deoxygenated by bubbling nitrogen through solution for 10 min. Then tert-butylacetylene (6.62 mL, 54.32 mmol) and BINAP (676 mg, 1.09 mmol) are added to the mixture, and it is heated at 60° C. overnight under nitrogen. The mixture is diluted with $CH_2Cl_2$ and filtered through celite washing with $CH_2Cl_2$. Filtrate is washed with brine, organic fraction is separated, dried over $Na_2SO_4$, concentrated, and the residue is purified by column chromatography on silica gel eluting with gradient of EtOAc in hexane to give of 5-(3,3-dimethyl-but-1-ynyl)-3-(tert-butoxycarbonyl)amino-thiophene-2-carboxylic acid methyl ester.

$^1$H NMR ($CDCl_3$), ppm: 1.27 (s, 9H), 1.51 (s, 9H), 3.84 (s, 3H), 7.87 (s, 1H), 9.24 (br.s, 1H)

MS found (electrospray): [M+H] 338.17

Step II

To a solution of 5-(3,3-dimethyl-but-1-ynyl)-3-(tert-butoxycarbonyl)amino-thiophene-2-carboxylic acid methyl ester (4.344 g, 9.58 mmol) in $CH_2Cl_2$ (30 mL) is added trifluoroacetic acid (30 mL), and the mixture is stirred at room temperature overnight. Then it is evaporated to dryness, obtained residue is redissolved in $CH_2Cl_2$ and washed with aqueous $NaHCO_3$ and brine. Organic fraction is separated, dried over $Na_2SO_4$, and concentrated to give 3.135 g of crude 5-(3,3-dimethyl-but-1-ynyl)-3-amino-thiophene-2-carboxylic acid methyl ester.

1H NMR ($CDCl_3$), ppm: 1.28 (s, 9H), 3.80 (s, 3H), 5.36 (br.s, 2H), 6.49 (s, 1H)

MS found (electrospray): [M+H] 238.11

Step III

To a solution of 5-(3,3-dimethyl-but-1-ynyl)-3-amino-thiophene-2-carboxylic acid methyl ester (1.512 g, 5.97 mmol) and N-tert-butoxycarbonyl-piperidin-4-one (1.189 g, 5.97 mmol) in 2 mL of dry THF is added dibutyltin dichloride (181 mg, 0.60 mmol), and the mixture is stirred for 10 min at room temperature under nitrogen. Then phenylsilane (810 μL, 6.57 mmol) is added, and the mixture is stirred for 24 h at room temperature. Additional 595 mg of N-tert-butoxycarbonyl-piperidin-4-one, 90 mg of dibutyltin dichloride and 405 μL of phenylsilane are added, and the mixture is stirred for another 24 h. Then the mixture is diluted with $CH_2Cl_2$, washed with brine, organic fraction is separated, dried over $Na_2SO_4$, and concentrated to give 5.142 g of crude 5-(3,3-dimethyl-but-1-ynyl)-3-(N-tert-butoxycarbonyl-piperidin-4-yl)amino-thiophene-2-carboxylic acid methyl ester.

Step IV trans-4-Methylcyclohexyl carboxylic acid chloride (23.88 mmol) and pyridine (2.89 mL, 35.82 mmol) are added to a solution of 5-(3,3-dimethyl-but-1-ynyl)-3-(N-tert-butoxycarbonyl-piperidin-4-yl)amino-thiophene-2-carboxylic acid methyl ester from step III (5.142 g) in dry toluene (50 mL). The mixture is refluxed for 24 h, then it is brought to room temperature, and additional amount of pyridine (1.0 mL) and MeOH (5 mL) are added. Then the mixture is diluted with $CH_2Cl_2$, washed with brine, organic fraction is separated, dried over $Na_2SO_4$, and concentrated to give 5.198 g of crude 5-(3,3-dimethyl-but-1-ynyl)-3-[(trans-4-methyl-cyclohexanecarbonyl)-(N-tert-butoxycarbonyl-piperidin-4-yl)amino]-thiophene-2-carboxylic acid methyl ester containing variable amounts of 5-(3,3-dimethyl-but-1-ynyl)-3-[(trans-4-methyl-cyclohexanecarbonyl)-(piperidin-4-yl)-amino]-thiophene-2-carboxylic acid methyl ester.

Step V

The product from step 1V (5.198 g) is dissolved in 30 mL of $CH_2Cl_2$ and treated with 20 mL of trifluoroacetic acid. The mixture is stirred at room temperature overnight, then it is evaporated to dryness, obtained residue is redissolved in $CH_2Cl_2$ and washed with aqueous $NaHCO_3$ and brine. Organic fraction is separated, dried over $Na_2SO_4$, and concentrated to give 5.340 g of crude 5-(3,3-dimethyl-but-1-ynyl)-3-[(trans-4-methyl-cyclohexanecarbonyl)-(piperidin-4-yl)amino]-thiophene-2-carboxylic acid methyl ester.

Step VI

To a solution of the product from step V (5.340 g) in 1,2-dichloroethane (60 mL) is added formaldehyde (1.94 mL of 37% aqueous solution, 23.88 mmol), followed by sodium triacetoxyborohydride (2.403 g, 11.34 mmol) in portions over 20 min. The mixture is stirred at room temperature overnight, then water is added to the mixture, and it is extracted with $CH_2Cl_2$. Organic fraction is washed with aqueous $NaHCO_3$ and brine, dried over $Na_2SO_4$, concentrated and purified by column chromatography on silica gel eluting with 0-10% of MeOH in $CH_2Cl_2$ to give 5-(3,3-dimethyl-but-1-ynyl)-3-[(trans-4-methyl-cyclohexanecarbonyl)-(1-methyl-piperidin-4-yl)-amino]-thiophene-2-carboxylic acid methyl ester.

Step VII

The product from Step VI (281 mg, 0.61 mmol) is hydrolysed with lithium hydroxide as previously described (example 1, step VI) to give after HPLC purification 5-(3,3-dimethyl-but-1-ynyl)-3-[(trans-4-methyl-cyclohexanecarbonyl)-(1-methyl-piperidin-4-yl)-amino]-thiophene-2-carboxylic acid hydrochloride.

MS found (electrospray): [M+H]: 445.29

EXAMPLE 9

5-(3,3-Dimethyl-but-1-ynyl)-3-[(trans-4-hydroxy-cyclohexyl)-(trans-4-methyl-cyclohexane-carbonyl)-amino]-thiophene-2-carboxylic acid

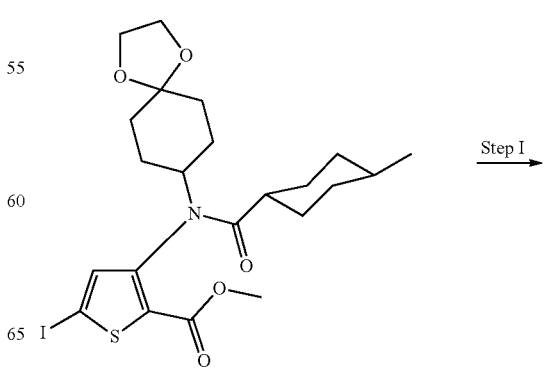

51
-continued

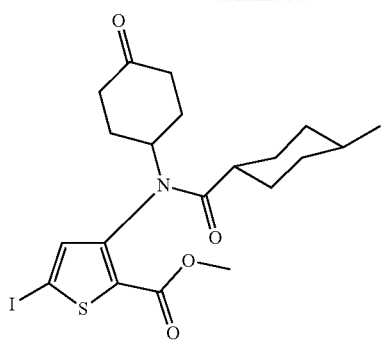

Step II

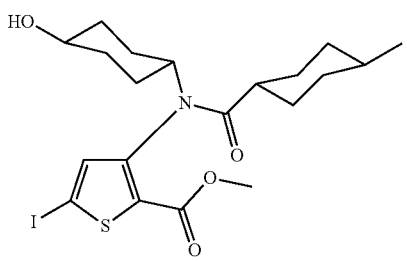

Step III

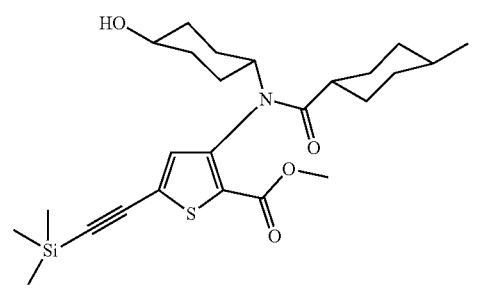

Step IV

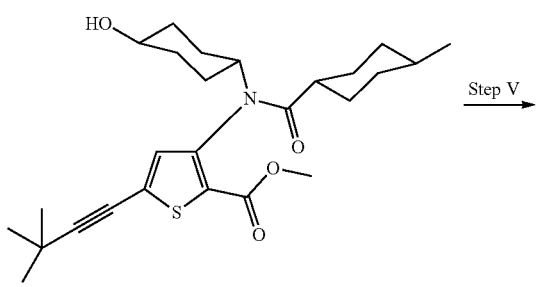

Step V

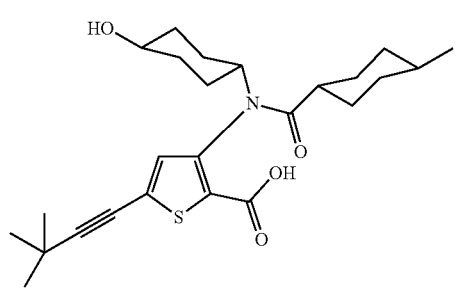

52

Step I

3-[(1,4-Dioxa-Spiro[4.5]dec-8-yl)-(trans-4-methyl-cyclohexanecarbonyl)-amino]-5-iodo-thiophene-2-carboxylic acid methyl ester (from example 3) is dissolved in tetrahydrofuran and treated with 3N HCl solution. The reaction is stirred at 40° C. for 3 h. The reaction mixture is evaporated under reduced pressure. The mixture is dissolved in EtOAc and washed with aq. sat. NaHCO$_3$ solution. The organic layer is separated, dried over Na$_2$SO$_4$, filtered and concentrated to obtain the title compound.

Step II

To a cold (0° C.) solution of 5-iodo-3-[(trans-4-methyl-cyclohexanecarbonyl)-(4-oxo-cyclohexyl)-amino]-thiophene-2-carboxylic acid methyl ester in MeOH under a N$_2$ atmosphere, NaBH$_4$ is added portion wise and is stirred. After the reaction is completed, 2% HCl is added and stirred for 15 min. The reaction mixture is concentrated under vacuum to dryness. The residue is partitioned between water and EtOAC. The organic layer is separated, dried over MgSO$_4$ and concentrated to dryness. The residue is purified by silica gel column chromatography using EtOAc:hexane as eluent to obtain the title compound.

Step III

To a solution of 3-[(trans-4-hydroxy-cyclohexyl)-(trans-4-methyl-cyclohexanecarbonyl)-amino]-5-iodo-thiophene-2-carboxylic acid methyl ester and ethynyl-trimethyl-silane in DMF, triethylamine and tris(dibenzylideneacetone)dipalladium (0) are added and the reaction mixture is stirred at 60° C. for 16 h under a N$_2$ atmosphere. DMF and triethylamine are removed under reduced pressure and the residue is partitioned between water and ethyl acetate. The organic layer is separated, dried (Na$_2$SO$_4$), concentrated and the residue is purified by column chromatography using ethyl acetate and hexane (1:2) as eluent to obtain the title compound.

Step IV

3-[(trans-4-Hydroxy-cyclohexyl)-(trans-4-methyl-cyclohexanecarbonyl)-amino]-5-trimethyl-silanylethynyl-thiophene-2-carboxylic acid methyl ester and 2-chloro-2-methylpropane are taken in dichloromethane and added freshly sublimed aluminium chloride at −78° C. The reaction mixture is stirred at the same temperature for 6 h. The reaction mixture is poured into water, diluted with dichloromethane. The organic layer is separated, dried (Na$_2$SO$_4$) and concentrated. The residue is purified by column chromatography using ethyl acetate and hexane to obtain the title compound.

Ref.: J. Chem. Soc., Chem. Commun., 1982, 959-960.

Step V 5-(3,3-Dimethyl-but-1-ynyl)-3-[(trans-4-hydroxy-cyclohexyl)-(trans-4-methyl-cyclohexane-carbonyl)-amino]-thiophene-2-carboxylic acid methyl ester is dissolved in a 3:2:1 mixture of THF:methanol:H$_2$O and treated with a 1N solution of LiOH.H$_2$O. After 2 h of stirring at 60° C., the reaction mixture is concentrated under reduced pressure on a rotary evaporator. The mixture is partitioned between ethyl acetate and water. The water layer is acidified using 0.1 N HCl. The EtOAc layer is separated and dried over Na$_2$SO$_4$. The solvent is removed and the residue is purified by column chromatography using methanol and dichloromethane (1:9) as eluent to obtain the title compound.

TABLE 1

| | List of compounds in accordance with the present invention | | |
|---|---|---|---|
| | Structure | Chemical Name | Mass* |
| 1 | | 5-(3,3-DIMETHYL-BUT-1-YNYL)-3-[(TRANS-4-HYDROXY-CYCLOHEXYL)-(TRANS-4-METHYL-CYCLOHEXANECARBONYL)-AMINO]-THIOPHENE-2-CARBOXYLIC ACID | (M − H): 444.3 |
| 2 | | 5-(3,3-DIMETHYL-BUT-1-YNYL)-3-[(TRANS-4-METHOXY-CYCLOHEXYL)-(TRANS-4-METHYL-CYCLOHEXANECARBONYL)-AMINO]-THIOPHENE-2-CARBOXYLIC ACID | (M − H): 458.3. |
| 3 | | 5-(3,3-DIMETHYL-BUT-1-YNYL)-3-[(TRANS-4-METHYL-CYCLOHEXANECARBONYL)-(CIS-4-[1,2,4]TRIAZOL-1-YL-CYCLOHEXYL)-AMINO]-THIOPHENE-2-CARBOXYLIC ACID | (M + H): 497.4 |

TABLE 1-continued

List of compounds in accordance with the present invention

| | Structure | Chemical Name | Mass* |
|---|---|---|---|
| 4 | 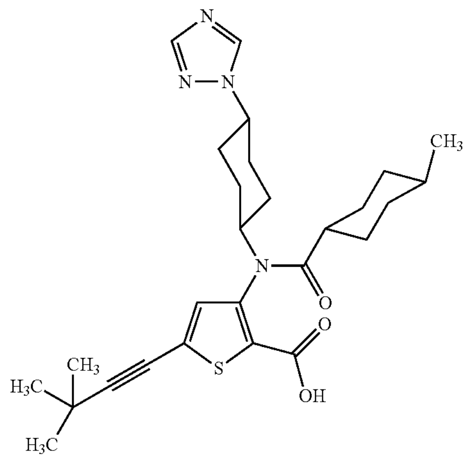 | 5-(3,3-DIMETHYL-BUT-1-YNYL)-3-[(TRANS-4-METHYL-CYCLOHEXANECARBONYL)-(TRANS-4-[1,2,4]TRIAZOL-1-YL-CYCLOHEXYL)-AMINO]-THIOPHENE-2-CARBOXYLIC ACID | (M + H): 497.4 |
| 5 | 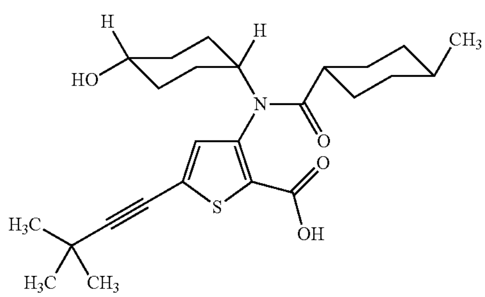 | 5-(3,3-DIMETHYL-BUT-1-YNYL)-3-[(CIS-4-HYDROXY-CYCLOHEXYL)-(TRANS-4-METHYL-CYCLOHEXANECARBONYL)-AMINO]-THIOPHENE-2-CARBOXYLIC ACID | (M − H): 444.52 |
| 6 | 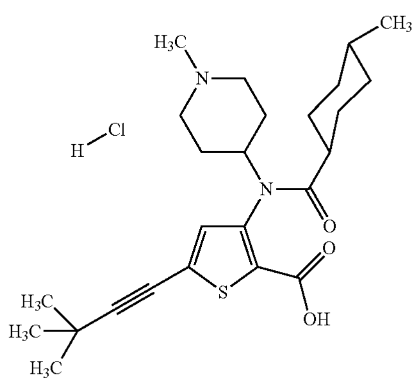 | 5-(3,3-DIMETHYL-BUT-1-YNYL)-3-[(TRANS-4-METHYL-CYCLOHEXANECARBONYL)-(1-METHYL-PIPERIDIN-4-YL)-AMINO]-THIOPHENE-2-CARBOXYLIC ACID; HYDROCHLORIDE | (M + H): 445.29 |
| 7 | 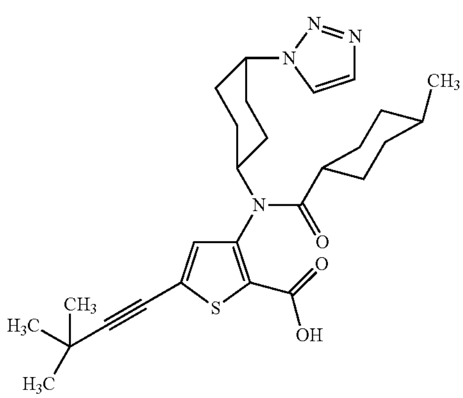 | 5-(3,3-DIMETHYL-BUT-1-YNYL)-3-[(TRANS-4-METHYL-CYCLOHEXANECARBONYL)-(4-CIS-[1,2,3]TRIAZOL-1-YL-CYCLOHEXYL)-AMINO]-THIOPHENE-2-CARBOXYLIC ACID | (M + H): 497.4 |

TABLE 1-continued

List of compounds in accordance with the present invention

| | Structure | Chemical Name | Mass* |
|---|---|---|---|
| 8 | (structure) | 5-(3,3-DIMETHYL-BUT-1-YNYL)-3-[(TRANS-4-METHYL-CYCLOHEXANECARBONYL)-(TRANS-4-[1,2,3]TRIAZOL-1-YL-CYCLOHEXYL)-AMINO]-THIOPHENE-2-CARBOXYLIC ACID | (M + H): 497.4 |
| 9 | (structure) | 5-(3,3-DIMETHYL-BUT-1-YNYL)-3-[(TRANS-4-FLUORO-CYCLOHEXYL)-(TRANS-4-METHYL-CYCLOHEXANECARBONYL)-AMINO]-THIOPHENE-2-CARBOXYLIC ACID | (M + H): 448.30 |

*mass spectral analyses are recorded using electrospray mass spectrometry.

EXAMPLE 10

Evaluation of Compounds in The HCV RNA-Dependent RNA Polymerase Assay

The following references are all incorporated by reference:
1. Behrens, S., Tomei, L., De Francesco, R. (1996) *EMBO* 15, 12-22
2. Harlow, E, and Lane, D. (1988) *Antibodies: A Laboratory Manual.* Cold Spring Harbord Laboratory. Cold Spring Harbord. N.Y.
3. Lohmann, V., Körner, F., Herian, U., and Bartenschlager, R. (1997) *J. Virol.* 71, 8416-8428
4. Tomei, L., Failla, C., Santolini, E., De Francesco, R., and La Monica, N. (1993) *J Virol* 67, 4017-4026

Compounds are evaluated using an in vitro polymerase assay containing purified recombinant HCV RNA-dependent RNA polymerase (NS5B protein). HCV NS5B is expressed in insect cells using a recombinant baculovirus as vector. The experimental procedures used for the cloning, expression and purification of the HCV NS5B protein are described below. Follows, are details of the RNA-dependent RNA polymerase assays for testing the compounds.

1. Expression of the HCV NS5B Protein in Insect Cells:

The cDNA encoding the entire NS5B protein of HCV-Bk strain, genotype 1b, was amplified by PCR using the primers NS5Nhe5' (5'-GCTAGCGCTAGCTCAATGTCCTACA-CATGG-3' (SEQ ID NO: 1)) and XhoNS53' (5'-CTC-GAGCTCGAGCGTCCATCGGTTGGGGAG-3' (SEQ ID NO: 2)) and the plasmid pCD 3.8-9.4 as template (Tomei et al, 1993). NS5Nhe5' and XhoNS53' contain two NheI and XhoI sites (underlined sequences), respectively, at their 5' end. The amplified DNA fragment was cloned in the bacterial expression plasmid pET-21b (Novagen) between the restriction sites NheI and XhoI, to generate the plasmid pET/NS5B. This plasmid was later used as template to PCR-amplify the NS5B coding region, using the primers NS5B-H9 (5'-ATA-CATATGGCTAGCATGTCAATGTCCTACACATGG-3' (SEQ ID NO: 3)) and NS5B-R4 (5'-GGATCCGGATC-CCGTTCATCGGTTGGGGAG-3' (SEQ ID NO: 4)). NS5B-H9 spans a region of 15 nucleotides in the plasmid pET-21b followed by the translation initiation codon (ATG) and 8 nucleotides corresponding to the 5' end of the NS5B coding region (nt. 7590-7607 in the HCV sequence with the accession number M58335). NS5B-R4 contains two BamHI sites (underlined) followed by 18 nucleotides corresponding to the region around the stop codon in the HCV genome (nt. 9365-9347). The amplified sequence, of 1.8 kb, was digested with NheI and BamHI and ligated to a predigested pBlueBacII plasmid (Invitrogen). The resulting recombinant plasmid was designated pBac/NS5B. Sf9 cells were co-transfected with 3 μg of pBac/NS5B, together with 1 μg of linearized baculovirus DNA (Invitrogen), as described in the manufacturer's protocol. Following two rounds of plaque purification, an NS5B-recombinant baculovirus, BacNS5B, was isolated. The presence of the recombinant NS5B protein was determined by western blot analysis (Harlow and Lane, 1988) of BacNS5B-infected Sf9 cells, using a rabbit polyclonal antiserum (anti-NS5B) raised against a His-tagged version of the NS5B protein expressed in *E. coli*. Infections of Sf9 cells with this plaque purified virus were performed in one-liter spinner flasks at a cell density of $1.2 \times 10^6$ cells/ml and a multiplicity of infection of 5.

2. Preparation of a Soluble Recombinant NS5B Protein:

Sf9 cells were infected as described above. Sixty hours post-infection, cells were harvested then washed twice with phosphate buffer saline (PBS). Total proteins were solubilized as described in Lohmann et al. (1997) with some modifications. In brief, proteins were extracted in three steps, S1, S2, S3, using lysis buffers (LB) I, LB II and LB III (Lohmann et al, 1997). The composition of LBII was modified to contain 0.1% triton X-100 and 150 mM NaCl to reduce the amount of solubilized NS5B protein at this step. In addition, sonication of cell extracts was avoided throughout the protocol to preserve the integrity of the protein structure.

3. Purification of Recombinant NS5B using Fast Protein Liquid Chromatography (FPLC):

Soluble NS5B protein in the S3 fraction was diluted to lower the NaCl concentration to 300 mM, then it incubated batchwise with DEAE sepharose beads (Amersham-Pharmacia) for 2 hrs at 4° C., as described by Behrens et al. (1996). Unbound material was cleared by centrifugation for 15 min at 4° C., at 25 000 rpm using a SW41 rotor (Beckman). The supernatant was further diluted to lower the NaCl concentration to 200 mM and subsequently loaded, with a flow rate of 1 ml/min, on a 5 ml HiTrap® heparin column (Amersham-Pharmacia) connected to an FPLC® system (Amersham-Pharmacia). Bound proteins were eluted in 1 ml fractions, using a continuous NaCl gradient of 0.2 to 1 M, over a 25 ml volume. NS5B-containing fractions were identified by sodium dodecyl sulfate polyacrylamide gel electrophoresis (SDS-PAGE), followed by western blotting using the anti-NS5B antiserum at a dilution of 1:2000. Positive fractions were pooled and the elution buffer was exchanged against a 50 mM $NaPO_4$ pH 7.0, 20% glycerol, 0.5% triton X-100 and 10 mM DTT, using a PD-10 column (Amersham-Pharmacia). The sample was then loaded onto a 1 ml HiTrap® SP column (Amersham-Pharmacia), with a flow rate of 0.1 ml/min. Bound proteins were eluted using a continuous 0 to 1 M NaCl gradient over a 15 ml volume. Eluted fractions were analyzed by SDS-PAGE and western blotting. Alternatively, proteins were visualized, following SDS-PAGE, by silver staining using the Silver Stain Plus kit (BioRad) as described by the manufacturer. Positive fractions were tested for RdRp activity (see below) and the most active ones were pooled, and stored as a 40% glycerol solution at –70° C.

In vitro HCV RdRp Flashplate Scintillation Proximity Assay (STREP-FLASH ASSAY) used to Evaluate Analogues:

This assay consists on measuring the incorporation of [$^3$H] radiolabelled UTP in a polyrA/biotinylated-oligo dT template-primer, captured on the surface of streptavidin-coated scintillant-embeded microtiter Flashplates™ (NEN Life Science Products inc, MA, USA, SMP 103A). In brief, a 400 ng/µl polyrA solution (Amersham Pharmacia Biotech) was mixed volume-to-volume with 5' biotin-oligo $dT_{15}$ at 20 µmol/µl. The template and primers were denatured at 95 C for 5 minutes then incubated at 37 C for 10 minutes. Annealed template-primers were subsequently diluted in a Tris-HCl containing buffer and allowed to bind to streptavidin-coated flashplates overnight. Unbound material was discarded; compounds were added in a 10 µl solution followed by a 10 µl of a solution containing 50 mM $MgCl_2$, 100 mM Tris-HCl pH 7.5, 250 mM NaCl and 5 mM DTT. The enzymatic reaction was initiated upon addition of a 30 µl solution containing the enzyme and substrate to obtain the following concentrations: 25 µM UTP, 1 µCi [$^3$H] UTP and 100 nM recombinant HCV NS5B. RdRp reactions were allowed to proceed for 2 hrs at room temperature after which wells were washed three times with a 250 µL of 0.15 M NaCl solution, air dried at 37 C, and counted using a liquid scintillation counter (Wallac Microbeta Trilex, Perkin-Elmer, MA, USA).

EXAMPLE 11

Cell-Based Luciferase Reporter HCV RNA Replication Assay Cell Culture

The compounds of the present invention are HCV polymerase inhibitors. Surprisingly, it has been found that the compounds according to the present invention and having a specific substitution pattern, exhibit an improved therapeutic index relative to other thiophene analogues.

Replicon cell lines Huh-7, 5.2 and ET which are derived from the Huh-7 hepatocarcinoma cell line were maintained in culture as generally described in Krieger, N; Lohmann, V; Bartenschlager, R. Enhancement of hepatitis C virus RNA replication by cell culture-adaptive mutations. *J. Virol.* 2001, 75, 4614-4624. The Huh-7, 5.2 cells contain the highly cell culture-adapted replicon $I_{389}$luc-ubi-neo/NS3-3'/5.1 construct that carries, in addition to the neomycin gene, an integrated copy to the firefly luciferase gene (Krieger, N; Lohmann, V; Bartenschlager, R. Enhancement of hepatitis C virus RNA replication by cell culture-adaptive mutations. *J. Virol.* 2001, 75, 4614-4624). This cell line allows measurement of HCV RNA replication and translation by measuring luciferase activity. It has been previously shown that the luciferase activity tightly follows the replicon RNA level in these cells (Krieger, N; Lohmann, V; Bartenschlager, R. Enhancement of hepatitis C virus RNA replication by cell culture-adaptive mutations. *J. Virol.* 2001, 75, 4614-4624). The Huh-7, ET cell line has the same features as those mentioned for Huh-7, 5.2 cell line, except that ET cells are more robust and contain an adaptative mutation in the HCV NS4B gene instead of NS5A. Both cell lines were maintained in cultures at a sub-confluent level (<85%) as the level of replicon RNA is highest in actively proliferating cells. The culture media used for cell passaging consist of DMEM (Gibco BRL Laboratories, Mississauga, ON, Canada) supplemented with 10% foetal bovine serum with 1% penicilin/streptomycin, 1% glutamine, 1% sodium pyruvate, 1% non-essential amino acids, and 350 ug/ml of G418 final concentration. Cells were incubated at 37° C., in an atmosphere of 5% $CO_2$ and passaged twice a week to maintain sub-confluence.

Approximately 3000 viable Huh-7, 5.2 or ET cells (100 µl) were plated per well in a white opaque 96-well microtiter plate. The cell culture media used for the assay was the same as described above except that it contains no G418 and no phenol red. After an incubation period of 3-4 hours at 37° C. in a 5% $CO_2$ incubator, compounds (100 µl) were added at various concentrations. Cells were then further incubated for 4 days at 37° C. in a 5% $CO_2$ incubator. Thereafter, the culture media was removed and cells were lysed by the addition of 95 µL of the luciferase buffer (luciferin substrate in buffered detergent). Cell lysates were incubated at room temperature and protected from direct light for at least 10 minutes. Plates were read for luciferase counts using a luminometer (Wallac MicroB eta Trilux, Perkin Elmer™, MA, USA).

The 50% inhibitory concentrations ($IC_{50}$s) for inhibitory effect were determined from dose response curves using eleven concentrations per compound in duplicate. Curves were fitted to data points using nonlinear regression analysis, and $IC_{50}$s were interpolated from the resulting curve using GraphPad Prism software, version 2.0 (GraphPad Software Inc., San Diego, Calif., USA).

EXAMPLE 12

Evaluation of Compounds in 21 Amino acid C-Terminal Truncated HCV NS5B genotype 1b strain BK enzyme Assay The following references are all incorporated by reference:
Tomei, L., Failla, C., Santolini, E., De Francesco, R., and La Monica, N. (1993) J Virol 67, 4017-4026
Lesburg, C. A. et al. Crystal structure of the RNA-dependent RNA polymerasefrom hepatitis C virus reveals a fully encircled active site. Nat. Struct. Biol. 6, 937-943 (1999).
Ferrari, E. et al. Characterization of soluble hepatitis C virus RNA-dependent RNA polymerase expressed in *Escherichia coli*. J. Virol. 73, 1649-1654 (1999).

Compounds are evaluated using an in vitro polymerase assay containing purified recombinant HCV RNA-dependent RNA polymerase (NS5B protein) expressed in bacterial cells. The experimental procedures used for the cloning, expression and purification of the HCV NS5B protein are described below. Follows, are details of the RNA-dependent RNA polymerase assays for testing the compounds.

4. Expression of the HCV NS5B Protein in Insect Cells:
Expression and Purification of HCV NS5B Protein A recombinant soluble form representing a 21 amino acid C-terminal truncated HCV NS5B genotype 1b strain BK enzyme (Tomei et al, 1993) containing an N-terminal hexahistidine tag (SEQ ID NO: 5) was cloned and expressed in *Escherichia coli* BL21 (DE3). The truncated enzyme was purified as described in Lesburg et al. (1999) and Ferrari et al. (1999) with minor modifications. Briefly, soluble bacterial lysates were loaded onto a HiTrap nickel chelating affinity column (GE Healthcare, Baie d'Urfe, QC, Canada). The bound enzyme was eluted using an imidazole gradient. Imidazole was then removed from the buffer of the pooled active fractions using PD-10 desalting columns (GE Healthcare, Baie d'Urfe, QC, Canada). Further purification was achieved by running the protein preparation through a cation exchange HiTrap SP sepharose column (GE Healthcare, Baie d'Urfe, QC, Canada) using a NaCl gradient for elution. Thereafter, buffer was changed to 10 mM Tris pH 7.5, 10% glycerol, 5 mM DTT, 600 mM NaCl using a PD-10 column. Positive fractions were tested for RNA-dependent polymerase activity and the most active fractions were pooled and stored at −70° C.

In Vitro NS5B Assay

Measurement of the inhibitory effect of compounds on HCV NS5B polymerization activity was performed by evaluating the amount of radiolabeled UTP incorporated by the enzyme in a newly synthesized RNA using a homopolymeric RNA template/primer. Briefly, a 15-mer 5' biotinylated DNA oligonucleotide (oligo dT) primer annealed to a homopolymeric poly rA RNA template is captured on the surface of streptavidin-coated bead (GE Healthcare, Baie d'Urfe, QC, Canada). Essentially, compounds were tested at a variety of concentrations (0.005 to 200 µM) in a final volume of 50 µL reaction mixture consisting of 20 mM Tris-HCl pH 7.5, 5 mM $MgCl_2$, 1 mM DTT, 50 mM NaCl, 50 nM purified NS5B enzyme, 250 ng of polyrA/oligodT15 (Invitrogen, Burlington, Ontario, Canada), 15-µM of nonradioactive UTP, and 1 µCi of [$^3$H]UTP (3000 Ci/mmol; GE Healthcare., Baie d'Urfe, QC, Canada). The polymerization activity of the HCV NS5B enzyme is quantified by measuring the incorporation of radiolabeled [3H]UTP substrate onto the growing primer 3' end and detection is achieved by counting the signal using a liquid scintillation counter (Wallac MicroBeta Trilux, Perkin Elmer™, MA, USA).

[3H]Thymidine Incorporation Assay

A total of 1,000-2,000 cells/well are seeded in 96-well cluster dishes in a volume of 150 µl of DMEM (Life Technologies, Inc., Gaithersburg, Md.) supplemented with 10% FBS (HyClone Laboratories, Inc., Logan, Utah) and 2 mM glutamine (Life Technologies, Inc.). Penicillin and streptomycin (Life Technologies, Inc.) are added to 500 U/mL and 50 µg/mL final concentrations, respectively. After an incubation of 18 h at 37° C. in an atmosphere of 5% CO2, the medium is removed and replaced with compounds diluted in culture medium. Six serial two-fold dilutions of drugs are tested in triplicate. After further 72-h incubation, a volume of 50 µL of a 10 µCi/mL solution of [3H] methyl thymidine (Amersham Life Science, Inc., Arlington Heights, Ill.; 2 Ci/mmol) in culture medium is added and the plates are incubated for a further a 18 h at 37° C. Cells are then washed with phosphate-buffered saline (PBS), trypsinized for 2 min, and collected onto a fiberglass filter using a Tomtec cell harvester (Tomtec, Orange, Conn.). Filters are dried at 37° C. for 1 h and placed into a bag with 4.5 mL of liquid scintillation cocktail (Wallac Oy, Turku, Finland). The accumulation of [3H] methyl thymidine, representing viable replicating cells, is measured using a liquid scintillation counter (1450-Microbeta; Wallac Oy). Ref. SOP: 265-162-03. For this experiment, the cell lines used are; Huh-7 ET (cells derived from the Huh-7 cell line (hepatocellular carcinoma, human) and containing a HCV sub-genomic replicon), Molt-4 (peripheral blood, acute lymphoblastic leukemia, human), DU-145 (prostate carcinoma, metastasis to brain, human), Hep-G2 (hepatocellular carcinoma, human), and SH-SY5Y (neuroblastoma, human) cells.

Data Analysis

The 50% cytotoxic concentrations (CC50s) for cell toxicity are determined from dose response curves using six to eight concentrations per compound in triplicate. Curves are fitted to data points using non-linear regression analysis, and IC50 values are interpolated from the resulting curve using GraphPad Prism software, version 2.0 (GraphPad Software Inc., San Diego, Calif., USA).

TI: Ratio of CC50/IC50 in HCV replicon cells (Huh-7 ET cells) from example 12. When the compounds are tested more than once, the average of the TI is provided.

Table 2 lists the therapeutic indexes (Tis) of selected compounds representative of the invention relative to other thiophene HCV poylymerase inhibitors.

TABLE 2

| Compound | TI |
|---|---|
| 1 | ++++++ |
| 2 | +++ |
| 3 | ++++++ |
| 4 | ++++ |
| 5 | ++++++ |
| 6 | ++++++ |
| 7 | +++++ |
| 8 | ++++++ |
| 9 | ++++++ |

TABLE 2-continued
| | |
|---|---|
| A | ++ |
| B | ++ |
| C | + |
| D | ++++ |
| E | +++ |
| F | ++ |
| G | +++ |
| H | + |
| I | ++ |
TI
+: <100
++: 100-1000
+++: 1000-2000
++++: 2000-4000
+++++: 4000-6000
++++++: >6000
A
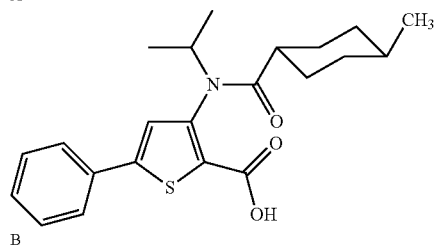
B
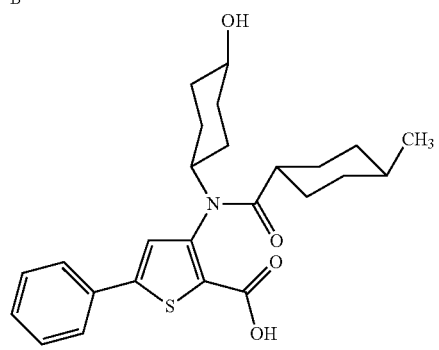
C
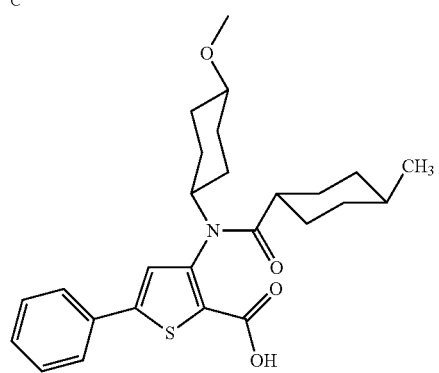
D
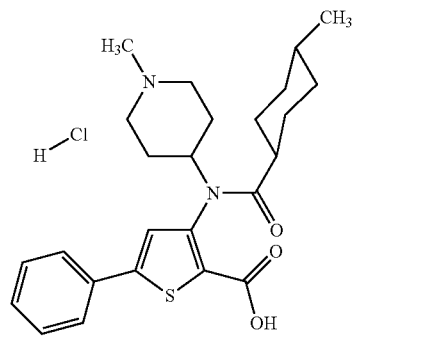
TABLE 2-continued
E
F
G
H TABLE 2-continued

I

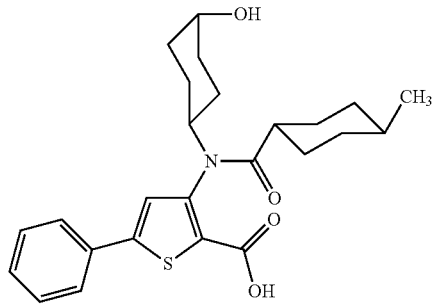

Compounds A to I can be synthesized as described in U.S. Pat. No. 6,881,741, WO02/100851, WO2004/052885, or WO 2006/072347.

EXAMPLE 13

Stability in Human and Rat Microsomes and Induction in Cultured Human Hepatocytes Certain compounds according to the present invention and having a specific substitution pattern, exhibit an improved microsome stability and/or Induction in human hepatocytes relative to other thiophene analogues. For example, compounds 1 and 2 showed better microsome stability profile and induction profile relative to compound E.

Stability in Human and Rat Microsomes

Each compound is incubated in hepatic microsomes (1.6 mg/mL) at 37° under oxidative and glucuronidation conditions (1.5 mM NADPH and 1.5 mM UDPGA in phosphate buffer, pH=7.4). Incubations containing no NADPH and no UDPGA are used as controls. The compounds are incubated at 50 uM for 0 and 60 minutes. The reaction is stopped by the addition of an equal volume of acetonitrile. The mixture is centrifuged and the supernatant is analyzed by HPLC/UV or MS/MS. The percentage parent remaining corresponds to the area of the parent compound in the 60-minute incubation versus the area of the parent compound in a 0-minute incubation ×100.

Induction in Cultured Human Hepatocytes

The induction is performed in cryopreserved or fresh cultured-human hepatocytes. The cells are cultured on collagen for 48 hours. Following this period, the cells are dosed with freshly spiked incubation media containing the test compound or the positive control inducer, rifampicin. Final concentrations of the test compounds in the incubations are 1, 10 and 100 mM while the positive control is tested at 10 mM. Negative controls (NC) consisted of incubating the cells with 0.1% DMSO final content. The cell treatment is pursued for a total of 48 hours with fresh incubation media spiked with test compound or control inducer replaced daily. At the end of the induction period, the media containing the inducer is removed and cells are washed twice with 200 uL Krebs-Henseleit buffer containing 12 mM HEPES, pH 7.4 (KH buffer). The induction of CYP3A4 is then measured by activity using testosterone as substrate and by mRNA levels. For CYP3A4 activity, fresh KH buffer, spiked with the 200 mM testosterone is added and the cells are incubated for 30 minutes at 37° C. At the end of the incubation period, the media is removed and analyzed by HPLC/MS for 6-beta-hydroxy testosterone determination. The maximal induction (100% induction) is determined with the 10 mM Rifampicin treatment. The potential for test compounds to cause CYP3A Induction is described as a percentage of maximal induction obtained with the classic inducer. For mRNA level determination, hepatocytes are harvested and total RNA is prepared using Qiagen RNeasy Purification Kit (Mississauga, ON) according to manufacturer's instructions. The cDNAs of the hepatocytes are synthesized from total RNA using M-MLV Reverse Transcriptase (Invitrogen, Carlbad, Calif.) with universal primer (Roche Diagnostic, Germany). Analysis of specific mRNA expression in total RNA samples is performed by quantitative real time PCR using Applied Biosystem's ABI Prism 7700 Sequence Detection System. Primers used for CYP3A4 are 5'-TCA GCC TGG TGC TCC TCT ATC TAT-3' (SEQ ID NO: 6) as forward primer and 5'-AAG CCC TTA TGG TAG GAC AAA ATA TTT-3' (SEQ ID NO: 7) as reverse primer. The probe used was 5'-/56-FAM/TCC AGG GCC CAC ACC TCT GCC T/36-TAMSp/-3' (SEQ ID NO: 8). The data are normalized to Ribosomal 18S mRNA (VIC) with real time detection. Data analysis and statistical tests are performed using Microsoft© Excel. Results can be reported as fold change gene expression compared to control group according to the following formula:

$$\Delta Ct = Ct\,FAM - Ct\,VIC$$

$$\Delta\Delta Ct = \Delta Ct\text{Drug Candidate} - \Delta Ct\text{Control}$$

Fold Induction: $2^{-\Delta\Delta Ct}$

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A compound selected from:
   5-(3,3-DIMETHYL-BUT-1-YNYL)-3-[(TRANS-4-METHOXY-CYCLOHEXYL)-(TRANS-4-METHYL-CYCLOHEXANECARBONYL)-AMINO]-THIOPHENE-2-CARBOXYLIC ACID;
   5-(3,3-DIMETHYL-BUT-1-YNYL)-3-[(TRANS-4-METHYL -CYCLOHEXANECARBONYL)-(CIS-4-[1,2,4]TRIAZOL-1-YL-CYCLOHEXYL) -AMINO]-THIOPHENE-2-CARBOXYLIC ACID;
   5-(3,3-DIMETHYL-BUT-1-YNYL)-3-[(TRANS-4-METHYL -CYCLOHEXANECARBONYL)-(TRANS-4-[1,2,4]TRIAZOL-1-YL-CYCLOHEXYL)-AMINO]-THIOPHENE-2-CARBOXYLIC ACID;
   5-(3,3-DIMETHYL-BUT-1-YNYL)-3-[(CIS-4-HYDROXY-CYCLOHEXYL)-(TRANS-4-METHYL-CYCLOHEXANECARBONYL)-AMINO]-THIOPHENE-2-CARBOXYLIC ACID;
   5-(3,3-DIMETHYL-BUT-1-YNYL)-3-[(TRANS-4-METHYL -CYCLOHEXANECARBONYL)-(1-METHYL-PIPERIDIN-4-YL)-AMINO]-THIOPHENE-2-CARBOXYLIC ACID; HYDROCHLORIDE;
   5-(3,3-DIMETHYL-BUT-1-YNYL)-3-](TRANS-4-METHYL -CYCLOHEXANECARBONYL)-(4-CIS-[1,2,3]TRIAZOL-1-YL-CYCLOHEXYL)-AMINO]-THIOPHENE-2-CARBOXYLIC ACID;
   5-(3,3-DIMETHYL-BUT-1-YNYL)-3-[(TRANS-4-METHYL -CYCLOHEXANECARBONYL)-(TRANS-4-[1,2,3]TRIAZOL-1-YL-CYCLOHEXYL) -AMINO]-THIOPHENE-2-CARBOXYLIC ACID;
   5-(3,3-DIMETHYL-BUT-1-YNYL)-3-[(TRANS-4-FLUORO-CYCLOHEXYL)-(TRANS-4-METHYL-CYCLOHEXANECARBONYL)-AMINO]-THIOPHENE-2-CARBOXYLIC ACID; and
   pharmaceutically acceptable salts thereof.

2. A compound of claim 1, wherein the compound is 5-(3,3-DIMETHYL-BUT-1-YNYL)-3-[(TRANS-4-METHOXY-CYCLOHEXYL)-(TRANS-4-METHYL-CYCLOHEXANECARBONYL)-AMINO]-THIOPHENE-2-CARBOXYLIC ACID.

3. A compound of claim 1, wherein the compound is 5-(3,3-DIMETHYL-BUT-1-YNYL)-3-](TRANS-4-METHYL -CYCLOHEXANECARBONYL)-(CIS-4-[1,2,4]TRIAZOL-1-YL-CYCLOHEXYL) -AMINO]-THIOPHENE-2-CARBOXYLIC ACID.

4. A compound of claim 1, wherein the compound is 5-(3,3-DIMETHYL-BUT-1-YNYL)-3-[(TRANS-4-METHYL -CYCLOHEXANECARBONYL)-(TRANS-4-[1,2,4]TRIAZOL-1-YL-CYCLOHEXYL) -AMINO]-THIOPHENE-2-CARBOXYLIC ACID.

5. A compound of claim 1, wherein the compound is 5-(3,3-DIMETHYL-BUT-1-YNYL)-3-](CIS-4-HYDROXY-CYCLOHEXYL)-(TRANS-4-METHYL-CYCLOHEXANECARBONYL)-AMINO]-THIOPHENE-2-CARBOXYLIC ACID.

6. A compound of claim 1, wherein the compound is 5-(3,3-DIMETHYL-BUT-1-YNYL)-3-[(TRANS-4-METHYL -CYCLOHEXANECARBONYL)-(1-METHYL-PIPERIDIN-4-YL)-AMIN]-THIOPHENE-2-CARBOXYLIC ACID; HYDROCHLORIDE.

7. A compound of claim 1, wherein the compound is 5-(3,3-DIMETHYL-BUT-1-YNYL)-3-[(TRANS-4-METHYL -CYCLOHEXANECARBONYL)-(4-CIS-[1,2,3]TRIAZOL-1-YL-CYCLOHEXYL) -AMINO]-THIOPHENE-2-CARBOXYLIC ACID.

8. A compound of claim 1, wherein the compound is 5-(3,3-DIMETHYL-BUT-1-YNYL)-3-[(TRANS-4-METHYL -CYCLOHEXANECARBONYL)-(TRANS-4-[1,2,3]TRIAZOL-1-YL-CYCLOHEXYL) -AMINO]-THIOPHENE-2-CARBOXYLIC ACID.

9. A compound of claim 1, wherein the compound is 5-(3,3-DIMETHYL-BUT-1-YNYL)-3-[(TRANS-4-FLUORO-CYCLOHEXYL)-(TRANS-4-METHYL-CYCLOHEXANECARBONYL)-AMINO]-THIOPHENE-2-CARBOXYLIC ACID.

10. A compound selected from:
    3-[(1,4-dioxa-spiro[4.5]dec-8-yl)-(trans-4-methyl-cyclohexanecarbonyl)-amino]-5-iodo-thiophene-2-carboxylic acid methyl ester;
    5-(3,3-dimethyl-but-1-ynyl)-3-(4-[1,2,3]triazol-1-yl-cyclohexylamino) -thiophene-2-carboxylic acid methyl ester;
    5-(3,3-dimethyl-but-1-ynyl)-3-(4-[1,2,4]triazol-1-yl-cyclohexylamino) -thiophene-2-carboxylic acid methyl ester;
    5-(3,3-dimethyl-but-1-ynyl)-3-(tert-butoxycarbonyl) amino-thiophene-2-carboxylic acid methyl ester;
    5-(3,3-dimethyl-but-1-ynyl)-3-amino-thiophene-2-carboxylic acid methyl ester;
    3-[(trans-4-hydroxy-cyclohexyl)-(trans-4-methyl-cyclohexanecarbonyl) -amino]-5-iodo-thiophene-2-carboxylic acid methyl ester; or
    3-[(trans-4-Hydroxy-cyclohexyl)-(trans-4-methyl-cyclohexanecarbonyl) -amino]-5-trimethyl-silanylethynyl-thiophene-2-carboxylic acid methyl ester.

11. A compound selected from:
    5-bromo-3-(1,4-dioxa-spiro[4.5]dec-8-ylamino)-thiophene-2-carboxylic acid methyl ester;
    5-bromo-3-[(1,4-dioxa-spiro[4.5]dec-8-yl)-(trans-4-methyl -cyclohexanecarbonyl)-amino]-thiophene-2-carboxylic acid methyl ester;
    5-(3,3-dimethyl-but-1-ynyl)-3-[(trans-4-hydroxy-cyclohexyl)-(trans-4-methyl-cyclohexanecarbonyl)-amino]-thiophene-2-carboxylic acid methyl ester;

3-(1,4-dioxa-spiro[4.5]dec-8-ylamino)-thiophene-2-carboxylic acid methyl ester;

3-[(1,4-dioxa-spiro[4.5]dec-8-yl)-(trans-4-methyl-cyclohexanecarbonyl)-amino]-thiophene-2-carboxylic acid methyl ester;

5-(3,3-dimethyl-but-1-ynyl)-3-[(1,4-dioxa-spiro[4.5]dec-8-yl)-(trans-4-methyl-cyclohexanecarbonyl)-amino]-thiophene-2-carboxylic acid methyl ester;

5-(3,3-dimethyl-but-1-ynyl)-3-[(trans-4-methyl-cyclohexanecarbonyl)-(4-oxo-cyclohexyl)-amino]-thiophene-2-carboxylic acid methyl ester;

5-(3,3-dimethyl-but-1-ynyl)-3-[(4-hydroxy-cyclohexyl)-(trans-4-methyl-cyclohexanecarbonyl)-amino]-thiophene-2-carboxylic acid methyl ester; and 5-(3,3-Dimethyl-but-1-ynyl)-3-[(trans-4-hydroxy-cyclohexyl)-(trans-4-methyl-cyclohexane-carbonyl)-amino]-thiophene-2-carboxylic acid methyl ester.

\* \* \* \* \*